United States Patent [19]

Higashi et al.

[11] Patent Number: 5,366,811

[45] Date of Patent: Nov. 22, 1994

[54] ORGANIC ELECTROLUMINESCENCE DEVICE

[75] Inventors: Hisahiro Higashi; Chishio Hosokawa; Hiroshi Tokailin, all of Sodegaura, Japan

[73] Assignee: Idemitsu Kosan Co., Ltd., Tokyo, Japan

[21] Appl. No.: 856,028

[22] PCT Filed: Sep. 17, 1991

[86] PCT No.: PCT/JP91/01228

§ 371 Date: May 4, 1992

§ 102(e) Date: May 4, 1992

[87] PCT Pub. No.: WO92/05131

PCT Pub. Date: Apr. 2, 1992

[30] Foreign Application Priority Data

Sep. 20, 1990 [JP] Japan ................... 2-248749
Oct. 19, 1990 [JP] Japan ................... 2-279304

[51] Int. Cl.$^5$ ................................. B32B 9/00
[52] U.S. Cl. ........................ 428/457; 313/504; 428/917; 252/301.16; 252/301.35; 585/24; 585/25; 585/27
[58] Field of Search ............... 252/301.16, 301.21, 252/301.34, 301.35; 428/690, 917, 1, 411.1, 457; 313/304–306; 585/406, 407, 422, 427, g351254, 25, 26, 27

[56] References Cited

U.S. PATENT DOCUMENTS

| | | | |
|---|---|---|---|
| 3,810,879 | 5/1974 | Hay | 528/25 |
| 4,232,042 | 11/1980 | Campbell et al. | 424/308 |
| 5,069,975 | 12/1991 | Nakada | 428/917 |
| 5,121,029 | 6/1992 | Hosokawa et al. | 313/504 |
| 5,126,214 | 6/1992 | Takailin et al. | 428/690 |
| 5,130,603 | 7/1992 | Tokailin et al. | 252/504 |

FOREIGN PATENT DOCUMENTS

| | | | |
|---|---|---|---|
| 168802 | 1/1986 | European Pat. Off. | 528/25 |
| 0390551 | 10/1990 | European Pat. Off. | |
| 52-46057 | 4/1977 | Japan . | |
| 2-285356 | 11/1990 | Japan . | |
| 2-292371 | 12/1990 | Japan . | |
| 3-230584 | 10/1991 | Japan . | |
| 855004 | 11/1960 | United Kingdom | 528/25 |

OTHER PUBLICATIONS

Nishimura et al., J. Am. Chem. Soc., 1983, 105, pp. 4758–4767.
Bohlmann et al., Chem Ber. 108, 2809–2817. (1975).
Streitwieser & Heathcock "Intro to Organic Chemistry" 1985, MacMillian Publishing pp. 780–782.
Moore, "Luminescent Organic Pigments" in *Pigment Handbook* vol. 1, Wiley and Sons, 1989.
Chemische Berichte, vol. 108, No. 8, (1975), F. Bohlmann et al. "Uber den Einfluß von Eu (fod)$_3$ als Verschiebungsreagenz auf die H–NMR-Spektren von Zimtsäurederivaten, II", pp. 2809–2817.
Chemische Berichte, vol. 122, No. 12, (1989), D. Hellwinkel et al., "Phenylvinylog erweiterte Triphenylmethylium–Systeme", pp. 2351–2359.
Journal of the American Chemical Society, vol. 105, No. 14 (1983), J. Nishimura et al., "Cationic Cyclocodimerization". 1. Novel Synthesis of the [3,3] Paracyclophane.

*Primary Examiner*—Patrick J. Ryan
*Assistant Examiner*—Patrick Jewik
*Attorney, Agent, or Firm*—Frishauf, Holtz, Goodman & Woodward

[57] ABSTRACT

An electroluminescence device (organic EL device) which comprises a pair of electrodes with an emitting layer therebetween. The emitting layer contains a dimerized styryl compound of the formula $$\underset{G-C=C-D-Q-D'-C=C-G'}{\overset{F\ \ E\ \ \ \ \ \ \ \ \ \ \ \ E'\ F'}{|\ \ |\ \ \ \ \ \ \ \ \ \ \ \ \ \ |\ \ |}}$$

wherein D and D' are each an arylene group or a divalent aromatic heterocyclic group, E, E', F, F' G and G' are each a hydrogen, an aryl group, an alkyl group, an aralkyl group, an alkoxyl group or a monovalent aromatic heterocyclic group and Q is a divalent group which breaks the conjugation. The dimerized styryl compound has a desirable light emitting efficiency which serves to increase the molecular weight to improve the thin film property. The organic EL device of the present invention is useful in preparing display devices.

28 Claims, No Drawings

ORGANIC ELECTROLUMINESCENCE DEVICE

DESCRIPTION

1. Technical Field

The present invention relates to an organic electroluminescence device. More particularly, it relates to a styryl compound obtained by combining fluorescent compounds with a divalent group to break the conjugated system, an efficient process for production thereof, and an organic electroluminescence device using the styryl compound as a light emitting material.

2. Background Art

Recently, since an electroluminescence device (hereinafter referred to as EL device) has features in distinguishing itself easily because of its self-emission and having a high impact resistance because it is a completely solid device, the uses of said device as a luminescent device for various display apparatus have attracted attention.

Said EL devices include an inorganic EL device comprising an inorganic compound as a light emitting material, and an organic EL device comprising an organic compound as a light emitting material. Among them, an organic EL device permits greatly reduced voltage to be applied, and, therefore, investigations have actively been undertaken to put it to practical use.

The above organic EL device basically comprises anode/light emitting layer/cathode, and those which are provided with a hole-injecting and -transporting layer and an electron-injecting and -transporting layer in addition to the above, for example, the structure as anode/hole-injecting and -transporting layer/light emitting layer/cathode, anode/light emitting layer/electron-injecting and -transporting layer/cathode, and anode/hole-injecting and -transporting layer/light emitting layer/electron-injecting and -transporting layer/cathode have been known. Said hole-injecting and -transporting layer has a function of transporting holes injected from the anode to the light emitting layer, and the electron-injecting and -transporting layer has a function of transporting electrons injected from the cathode to the light emitting layer. It has been known that by sandwiching said hole-injecting and -transporting layer between the light emitting layer and the anode, more holes are injected into the light emitting layer at lower voltage, and further, when the hole-injecting layer transports no electrons, electrons injected into the light emitting layer from the cathode or the electron-injecting and -transporting layer are accumulated in the light emitting layer near the interface of the hole-injecting layer and the light emitting layer, thereby light-emitting efficiency increases (Appl. Phys. Lett., Vol. 51, p.913 (1987)).

As to the conventional organic EL device, a device cannot be prepared favorably or its light emitting efficiency is undesirably decreased because the thin film property of the light emitting material is poor. Even if the light emitting material itself has EL performance, it is not favorably processed to a device because it becomes turbid in the course of being formed into a device. That is because the EL device looks milky turbid since the crystal particle diameter of the light emitting layer is close to the wavelength of visible light. Since the film thickness of the light emitting layer is as small as several 10 mm, in the light emitting layer of which crystal particle diameter is large, pinholes probably will occur, resulting in an incomplete device. Moreover, when the device is formed and allowed to stand at room temperature in the air or in an inert atmosphere or in an atmosphere of an inert gas, it crystallizes gradually and deterioration of a device is easy to occur due to pinholes. Further, after a device is formed, when a electric current is passed through the device, crystallization of the light emitting layer, melting, enlargement of pinholes, peeling of the layer and so on proceed due to the generation of the Joule heat of the device, and the device is deteriorated.

For the above reasons, none of conventional organic EL devices shows a light emission with a high brightness and a high efficiency under present conditions.

For example, it is reported that an EL emission of approximately 80 cd/m$^2$ was obtained using a distyrylbenzene compound known as a laser pigment in a monolayer as a light emitting material (European Patent No. 0,319,881). However, a light emission with a high brightness and a high efficiency has not been obtained because of the poor thin film property of the light emitting material (crystalline thin film).

It has also been reported that in the amorphous film such as an EL device comprising anode/hole-injecting layer/tetraphenylbutadiene/cathode (Appl. Phys. Lett., Vol. 56, p. 799 (1990)), a thin film free from pinholes cannot be formed and light emitting efficiency is poor.

As described above, the thin film property of the light emitting material is of significance. There are three factors as shown below in good thin film property.

(1) Thin Film Forming Ability

When the compound is formed into film by a known method such as the vapor deposition method, the spin-coating method, the casting method and the LB method, the thickness of the formed thin film can be controlled in the range of 5μm to 5 nm, a milky turbidity (crystallization) is not observed visually during the formation of thin film, a uniform microcrystalline or amorphous thin film can be formed without pinholes and without peeling-off observed clearly through the scanning electron microscope (SEM) directly after formation of thin film, and a thin film plane can be formed without the influence of the electrode and the like accumulated on the light emitting layer. The above facts are the indications of the thin film forming ability. The quantification can be obtained from the deviation of the film thickness of the light emitting layer observed by the SEM sectional view from the average film thickness as shown below.

| Rank | Deviation of film thickness of light emitting layer (Percentage to average film thickness) | Device | Thin film forming property |
| --- | --- | --- | --- |
| A) | ±50% | not producible | X |
| B) | ±30% | producible | Δ |
| C) | ±5% | good device | ◎ |

(2) Thin Film Maintaining Ability

The indications of the thin film maintaining ability are that, after the formation of thin film by the method described in (1), in the air or in an atmosphere of an inert gas (e.g., N$_2$ and At), deterioration of thin film plane due to precipitation of crystal, enlargement of pinholes and peeling-off proceed very slowly compared with the passage of time, and the microcrystalline or amorphous thin film can be maintained for a long time.

The quantification can be obtained through visual or SEM view observation as shown below.

| Rank | Precipitation of Crystal | Thin Film Maintaining Property |
|---|---|---|
| A) | directly after formation of device | X |
| B) | several days later | Δ |
| C) | more than six months later | ⊚ |

(3) Heat Resistant Thin Film Performance

The indications of heat resistant thin film performance is that, after the formation of a device, when an electric current is passed through the device, crystallization of the light emitting layer, melting, enlargement of pinholes, peeling-off of the layer and so on due to the generation of the Joule heat of the device proceed slowly and the device is not deteriorated. This factor can be evaluated quantitatively by measuring the glass transition temperature (Tg) of the light emitting material. In connection with (2), it is fundamentally necessary that Tg should be more than room temperature. When Tg is low, the rate of diffusion of molecules is increased, resulting in crystallization of the light emitting layer and the induction of disorder in the accumulated interface.

| Rank | Tg | Heat Resistant Thin Film Property |
|---|---|---|
| A) | under room temperature | X |
| B) | about room temperature | Δ |
| C) | over 50° C. | ⊚ |

The above three points are of importance. In order to satisfy these three conditions, it is first considered that the light emitting material may have high molecular weight. However, the material with mere high molecular weight (for example, polymer) causes lengthening of the wavelength of an EL emission or lowering of EL emission ability due to impurities contaminating during synthesis of a polymer.

In the case of a polymer, a distribution of molecular weight exists and there is a possibility that reproducible light emission may not be obtained.

DISCLOSURE OF THE INVENTION

Under the circumstances, the present inventors have found that when compounds suitable to an EL device with good light-emitting efficiency or wavelength are found, it is effective to combine these compounds with each other with a divalent group breaking the conjugated system to increase molecular weight (dimerization) as a means to improve a thin film property without decreasing the abilities of the compounds.

The present invention has been accomplished on the basis of such knowledge.

The present invention provides an organic electroluminescence device, which is characterized by using, as a light emitting material, a dimerized styryl compound represented by the general formula (a):

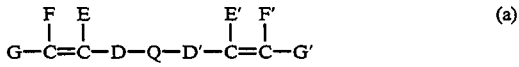

wherein D and D' are each a substituted or unsubstituted arylene group having 6 to 20 carbon atoms or a divalent aromatic heterocyclic group having 3 to 20 carbon atoms, and may be the same or different from each other. E, E', F, F', G and G' are each a hydrogen atom, a substituted or unsubstituted aryl group having 6 to 20 carbon atoms, a cyclohexyl group, an alkyl group having 1 to 10 carbon atoms, an aralkyl group having 7 to 20 carbon atoms, alkoxyl group having 1 to 10 carbon atoms, or a substituted or unsubstituted monovalent aromatic heterocyclic group having 3 to 20 carbon atoms, and may be the same or different from one another, excluding that F and G, and F' and G' are both hydrogen atoms.

The substituents described above are an alkyl group having 1 to 6 carbon atoms, an alkoxyl group having 1 to 6 carbon atoms, an acyl group having 1 to 6 carbon atoms, an aralkyl group having 7 to 8 carbon atoms, an aryloxy group having 6 to 20 carbon atoms, an alkoxycarbonyl group having 2 to 7 carbon atoms, an aryloxycarbonyl group having 7 to carbon atoms, an acyloxy group having 1 to 6 carbon atoms, an acylamino group having 1 to 6 carbon atoms, various halogen atoms, a carboxyl group, an amino-carbonyl group, a hydroxyl group, a cyano group, a nitro group, and an amino group (both mono-substituents and poly-substituents will do). Moreover, the mono-substituents may be an alkyl group, an aryloxy group, an amino group, or a phenyl group with or without a substituent. The poly-substituents may be an alkyl group, an alkoxyl group, an aryloxy group, an amino group, or a phenyl group with or without a substituent. E and D, or E' and D' may combine with each other to form a saturated or unsaturated five-membered or six-membered ring. E and G, or F' and G' may combine with each other to form a saturated or unsaturated five-membered or six-membered ring. Q is a divalent group breaking the conjugation.

The present invention also provides an organic electroluminescence device, which is characterized by using, as a light emitting material, a dimerized styryl compound represented by the general formula (b):

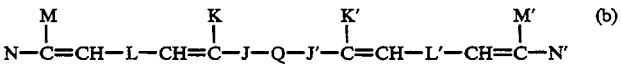

(wherein J, J', L and L' are each a substituted or unsubstituted arylene group having 6 to 20 carbon atoms or a divalent aromatic heterocyclic group having 3 to 20 carbon atoms, may be the same or different from one another. K, K', M, M', N and N' are each a hydrogen atom, a substituted or unsubstituted aryl group having 6 to 20 carbon atoms, a cyclohexyl group, an alkyl group having 1 to 10 carbon atoms, an aralkyl group having 7 to 20 carbon atoms, an alkoxyl group having 1 to 10 carbon atoms, or a substituted or unsubstituted monovalent aromatic heterocyclic group having 3 to 20 carbon atoms, and may be the same or different from one another, excluding that M and N, and M' and N' are both hydrogen atoms. The substituents are the same as defined above. The mono-substituent may be an alkyl group, an aryloxy group, an amino group, or a phenyl group with or without a substituent. The poly-substituent may be an alkyl group, an alkoxy group, an aryloxy group, an amino group, or a phenyl group with or without a substituent. K and J, or K' and J' may combine with each other to form a saturated or unsaturated five-membered or six-membered ring. M and N, or M' and N' may combine with each other to form a saturated or unsaturated five-membered or six-membered ring. Q is as defined above).

Moreover, the present invention provides a dimerized styryl compound represented by the above general formula (a) or (b).

THE MOST PREFERRED EMBODIMENT TO CARRY OUT THE INVENTION

In the compound represented by the general formula (a) of the present invention, E, F, G, E', F' and G' are each an aryl group (e.g., a phenyl group, a naphthyl group, an anthryl group, a biphenyl group, a terphenyl group, a pyrenyl group, a perylenyl group), a monovalent group comprising a cyclohexyl group, an alkyl group having 1 to 10 carbon atoms such as a methyl group, an ethyl group, an isopropyl group and a t-butyl group, an aralkyl group having 7 to 20 carbon atoms such as a benzyl group and a phenethyl group, an alkoxyl group having 1 to 10 carbon atoms such as a methoxyl group, an ethoxyl group, a propoxyl group and a butoxyl group, or a monovalent aromatic heterocyclic group having 3 to 20 carbon atoms and a hetero atom such as N, O and S, for example, a furyl group, a thienyl group, a pyrrolyl group, a quinolyl group, a carbazolyl group and an N-alkylcarbazolyl group. These aromatic heterocyclic groups may have or need not have substituents. Said substituents include, for example, an alkyl group having 1 to 6 carbon atoms such as a methyl group, an ethyl group, an isopropyl group, a t-butyl group and an n-pentyl group; an alkoxyl group having 1 to 6 carbon atoms such as a methoxyl group, an ethoxyl group, a propoxyl group and a butoxyl group; an acyl group having 1 to 6 carbon atoms such as a formyl group, an acetyl group, a propionyl group and a butylyl group; an aralkyl group having 7 to 8 carbon atoms such as a benzyl group and a phenethyl group, an aryloxy group such as a phenoxy group and tolyloxy group; an alkoxycarbonyl group having 2 to 7 carbon atoms such as a methoxycarbonyl group, an ethoxycarbonyl group, a propoxycarbonyl group and a butoxycarbonyl group; an aryloxycarbonyl group havimg 7 to 21 carbon atoms such as a phenoxycarbonyl group, a tolyloxycarbonyl group and a xylyloxycarbonyl group; an acyloxy group having 1 to 6 carbon atoms such as an acetyloxy group, a propionyloxy group and a butylyloxy group; an acylamino group having 1 to 6 carbon atoms such as an acetylamino group, a propionylamino group and a butylamino group; various halogen atoms; an aminocarbonyl group such as a carboxyl group, an anilinocarbonyl group, a carbamoyl group and a dimethylaminocarbonyl group; a triazole group with or without a substituent such as a hydroxyl group, a methyl group, an ethyl group, a phenyl group and a tolyl group; a monovalent group comprising pyrazoline with or without a substituent such as a methyl group, an ethyl group, a phenyl group and a tolyl group; a tolyl group, a xylyl group, a phenyl group; and further an amino group represented by the general formula:

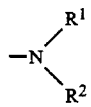

(wherein $R^1$ and $R^2$ are each a hydrogen atom, an aldehyde group, an alkyl group, an acyl group such as a formyl group, an acetyl group and a propionyl group, a phenyl group, or a substituted phenyl group such as a tolyl group and a xylyl group, and may be the same or different from each other. They may combine with each other to form a substituted or unsubstituted saturated five-membered ring or a substituted or unsubstituted saturated six-membered ring. They may combine with substituents on E, F, and G, or E', F' and G' to form a substituted or unsubstituted saturated five-membered ring or a substituted or unsubstituted saturated six-membered ring).

E, F and G, or E', F' and G' in the above general formula (a) may be the same or different from one another, or the substituents thereon may combine with one another to form a ring structure, excluding that F and G, and F' and G' are both hydrogen atoms.

D and D' in the above general formula (a) are each a substituted or unsubstituted arylene group having 6 to 20 carbon atoms such as a phenylene group, a biphenylene group, a naphthylene group, a terphenylene group, an anthracenediyl group, a pyrenediyl group and a perylemediyl group, or a divalent aromatic heterocyclic group having 3 to 20 carbon atoms such as a thienylene group, a pyrrolylene group, a pyridylene group, a quinolylene group, a carbazolylene group and an N-alkylcarbazolylene group. These arylene group and aromatic heterocyclic group may have or need not have substituents. Examples of said substituents are the same as in the above E, F and G, or E', F' and G'. The substituents on said D and D' may combine with each other to form a saturated five-membered ring with or without a substituent or a saturated six-membered ring with or without a substituent.

D and D' in the above general formula (a) may be the same or different from each other.

The above Q is a divalent group to break the conjugated system. The conjugation is attributed to the delocalization of $\pi$-electron, and includes a conjugated double bond or a conjugation due to an unpaired electron or a lone pair of electrons. Specific examples are a divalent group which results from removing each one hydrogen atom from a straight chain alkane, such as

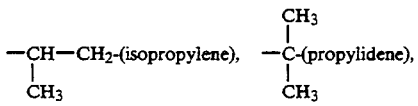

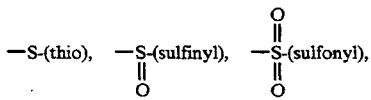

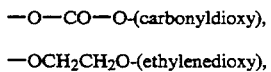

-continued

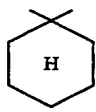 (cyclohexylidene), —NHCO-(amine),

—CO—CO-(oxalyl), —COCH₂CO-(malonyl),

—CO(CH₂)₂CO-(succinyl), —CO(CH₃)₃CO-(glutaryl),

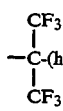

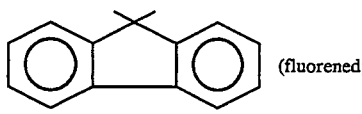 (fluorenedyl),

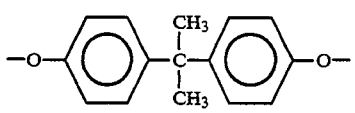

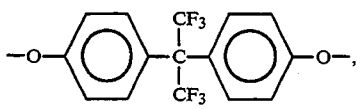

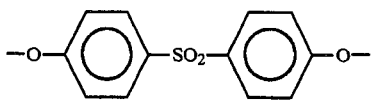

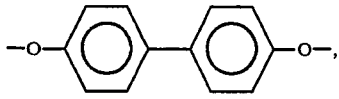

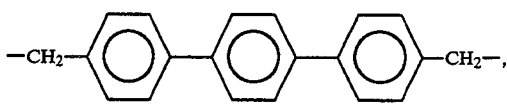

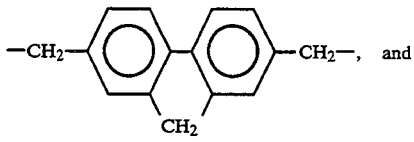

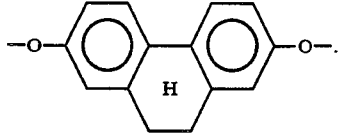

In the compound represented by the general formula (b), K, M and N, and K', M' and N' are each a hydrogen atom, a substituted or unsubstituted aryl group having 6 to 20 carbon atoms (e.g., a phenyl group, a naphthyl group, an anthryl group, a biphenyl group, a terphenyl group, a pyrenyl group and a perylenyl group), a cyclohexyl group, an alkyl group having 1 to 10 carbon atoms such as a methyl group, an ethyl group, an isopropyl group and a t-butyl group; an aralkyl group having 7 to 20 carbon atoms such as a benzyl group and a phenethyl group; an alkoxyl group having 1 to 10 carbon atoms such as a methoxyl group, an ethoxyl group, a propoxyl group and a butoxyl group; or a monovalent aromatic heterocyclic group having a hetero atom and 3 to 20 carbon atoms (e.g., a furyl group, a thienyl group, a pyrrolyl group, a pyridyl group, a quinolyl group, a carbazolyl group and an N-alkylcarbazolyl group). These cyclohexyl group and monovalent aromatic heterocyclic group may have or need not have substituents. Said substituents include, for example, an alkyl group having 1 to 6 carbon atoms such as a methyl group, an ethyl group, an isopropyl group, t-butyl group and an n-pentyl group; an alkoxyl group having 1 to 6 carbon atoms such as a methoxyl group, an ethoxyl group, a propoxyl group and a butoxyl group; an acyl group having 1 to 6 carbon atoms such as a formyl group, an acetyl group, a propionyl group and a butylyl group; an aralkyl group having 7 to 8 carbon atoms such as a benzyl group and a phenethyl group; an aryloxy group such as a phenoxyl group and a tolyloxy group; an alkoxycarbonyl group having 2 to 7 carbon atoms such as a methoxycarbonyl group, an ethoxycarbonyl group, a propoxycarbonyl group and a butoxycarbonyl group; an aryloxycarbonyl group having 7 to 21 carbon atoms such as a phenoxycarbonyl group, a tolyloxycarbonyl group and a xylyloxycarbonyl group; an acyloxy group having 1 to 6 carbon atoms such as an acetyloxy group, a propionyloxy group and a butylyloxy group; an acylamino group having 1 to 6 carbon atoms such as an acetylamino group, a propionylamino group and a butylylamino group; a halogen atom; a carboxyl group; an aminocarbonyl group such as an anilinocarbonyl group, a carbamoyl group and a dimethylaminocarbonyl group; a triazole group with or without a substituent such as a hydroxyl group, a methyl group, an ethyl group, a phenyl group and a tolyl group; a monovalent group comprising pyrazolyl with or without a substituent such as a methyl group, an ethyl group, a phenyl group and a tolyl group; a xylyl group; a phenyl group; and further an amino group represented by the general formula:

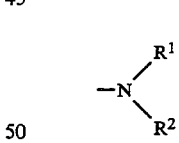

(wherein R¹ and R² are the same as defined above. They may combine with the groups substituted by K, M and N, or K', M' and N' to form a substituted or unsubstituted saturated five-membered ring or a substituted or unsubstituted saturated six-membered ring).

K, M, and N, or K', M' and N' in the above general formula (b) may be the same or different from one another, or the substituents thereon may combine with one another to form a ring structure, excluding that M and N, and M' and N' are both hydrogen atoms.

J and J', and L and L' in the above general formula (b) are each a substituted or unsubstituted arylene group having 6 to 20 carbon atoms (e.g., a phenylene group, a biphenylene group and a naphthylene group), or divalent aromatic heterocyclic group such as a thienylene group, a pyrrolylene group, a pyridylene group, a quinolylene group and a carbazolylene group. These arylene group and aromatic heterocyclic group may have or need not have substituents. Examples of said substituents are the same as those of the above K, M and N, or K', M' and N'. The substituents of J and J', and L and L' may combine with each other to form a saturated five-membered ring with or without a substituent.

J and J', and L and L' in the above general formula (b) may be the same or different from each other. Q is a divalent group to break a conjugated system. Specific examples are the same as defined above.

Specific examples of the compounds represented by the above general formulas (a) and (b) are compounds (1) to (77) as shown below.

(1) 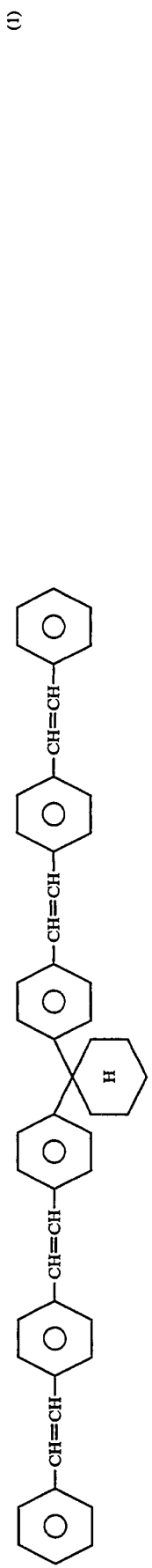
(2) 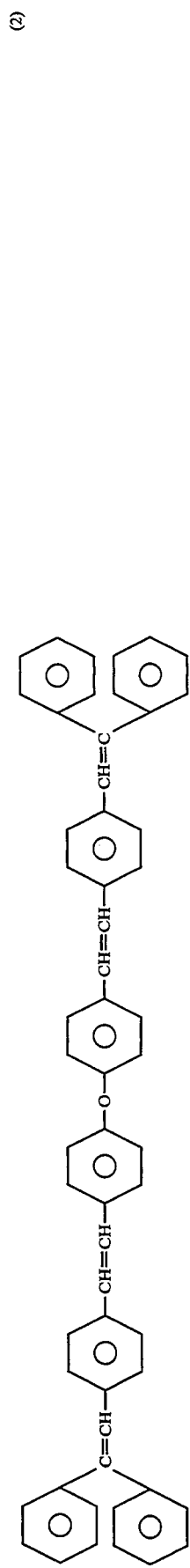
(3) 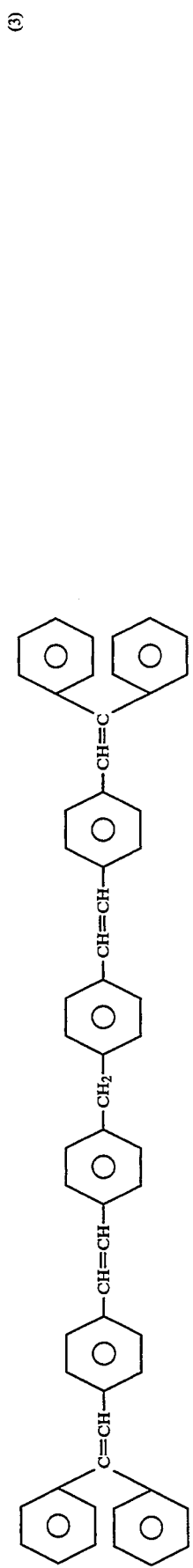
(4) 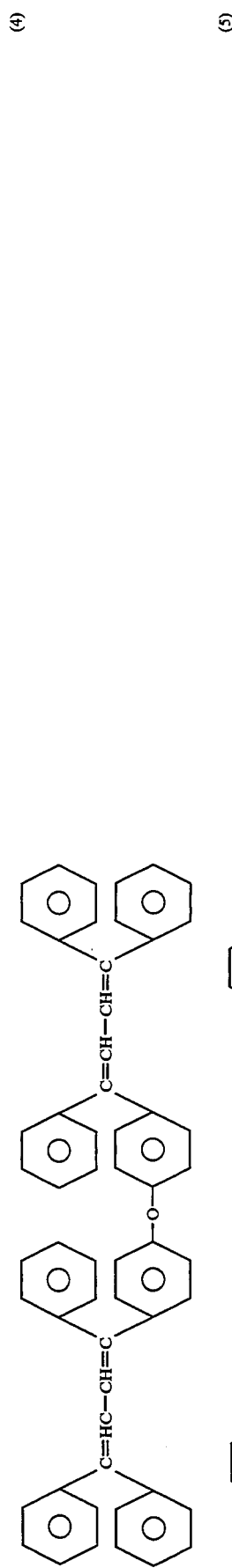
(5) 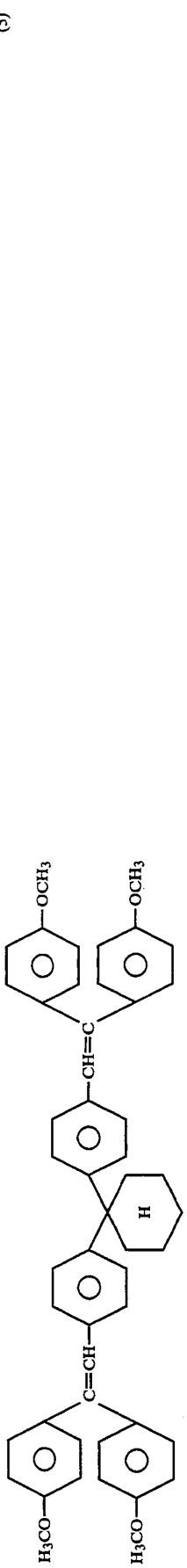

(6) 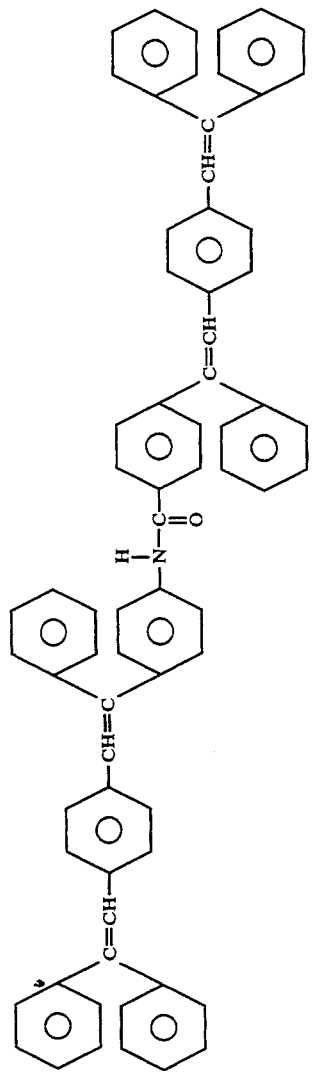
(7) 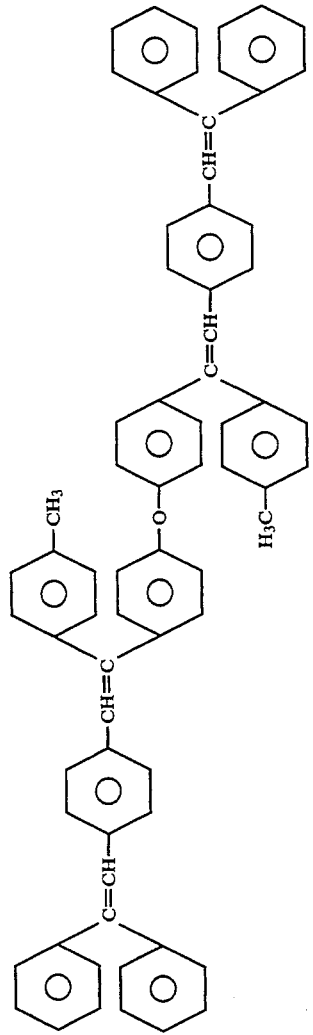
(8) 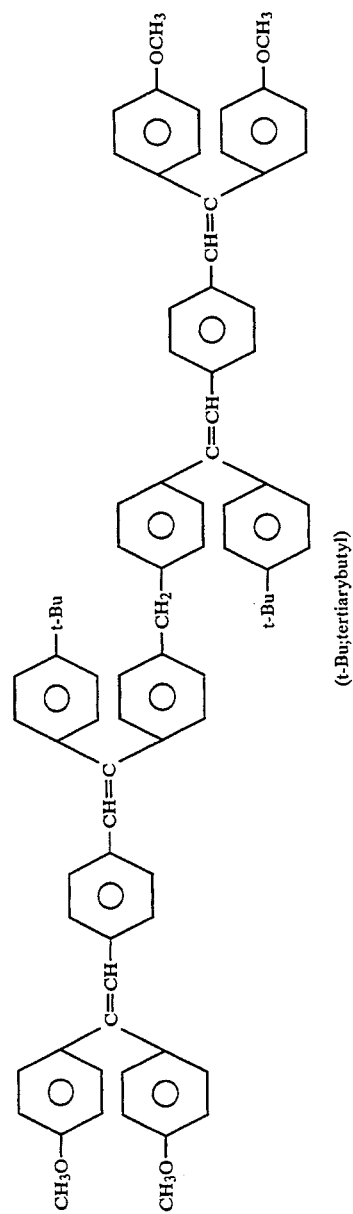

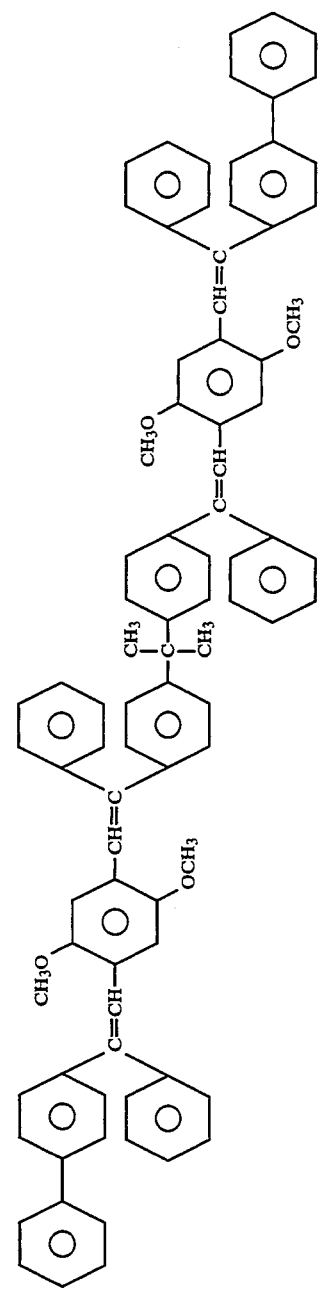

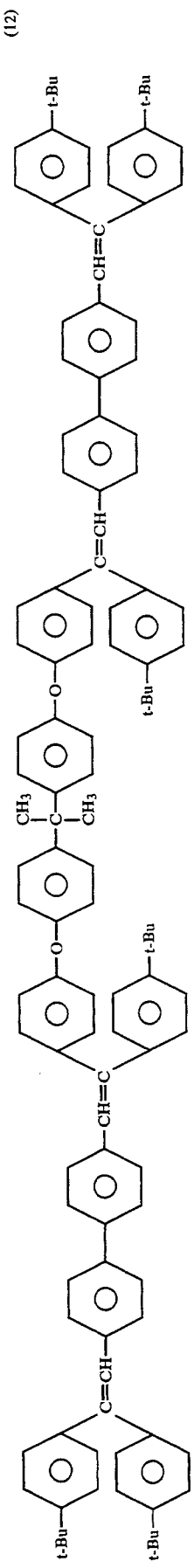
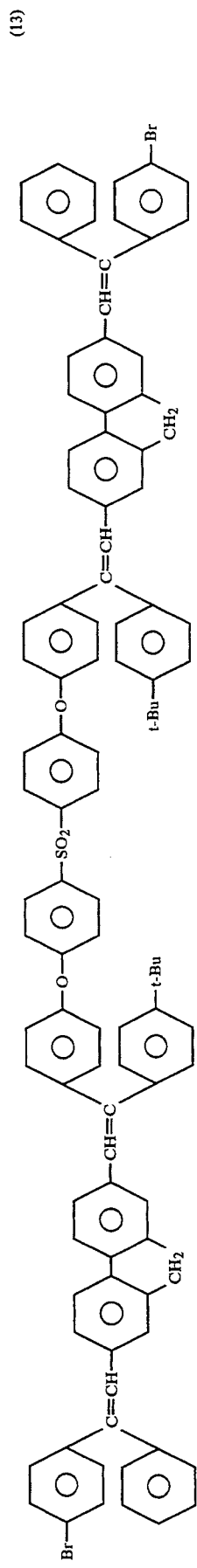
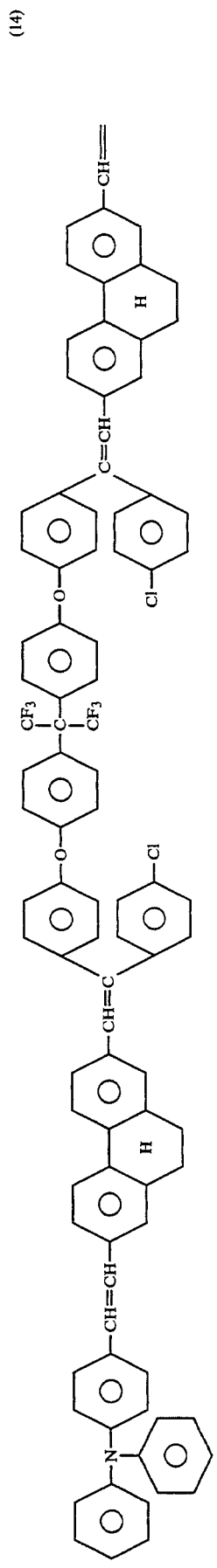

(15)
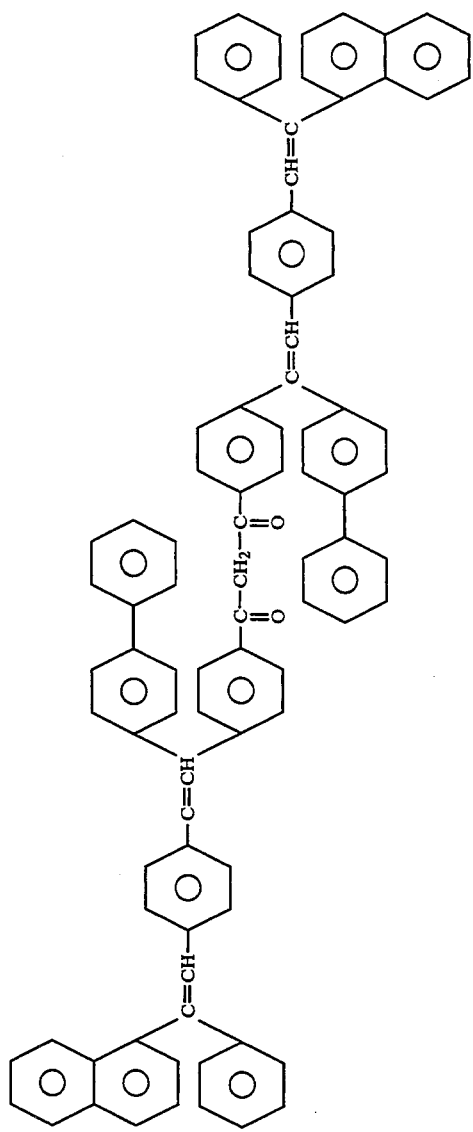
(16)
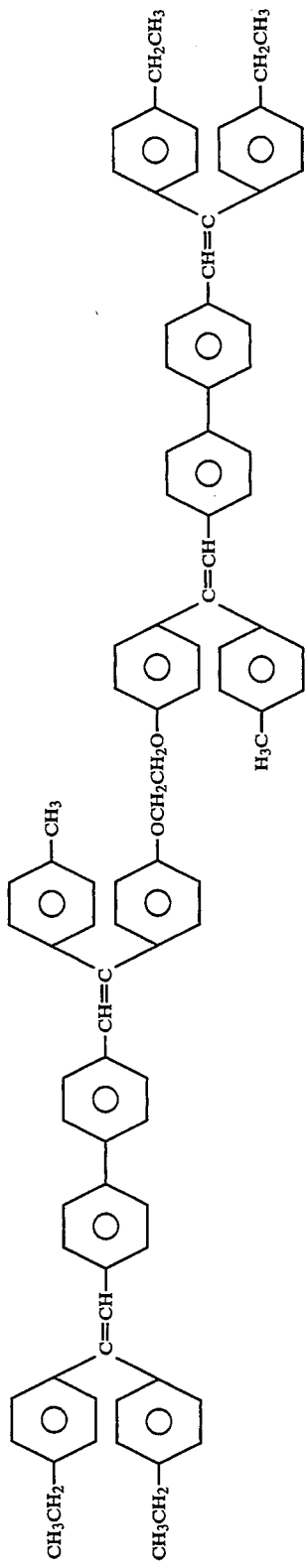
(17)
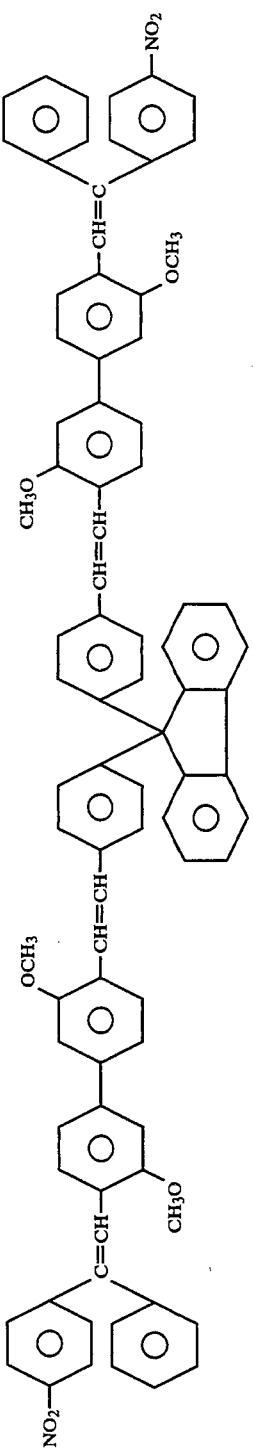

-continued
(18)
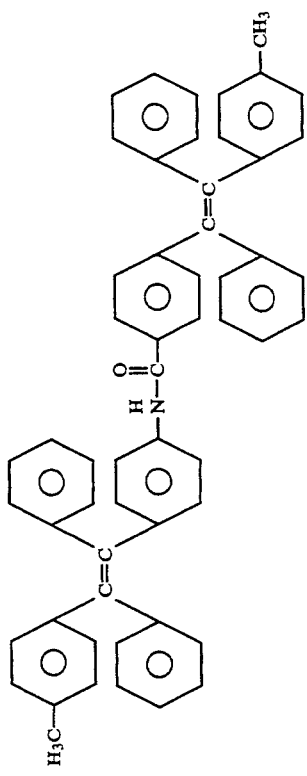
(19)
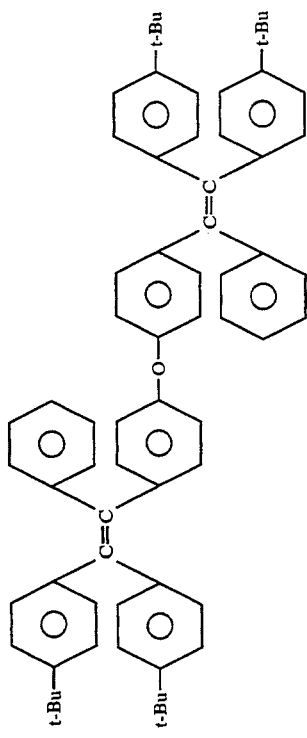
(20)
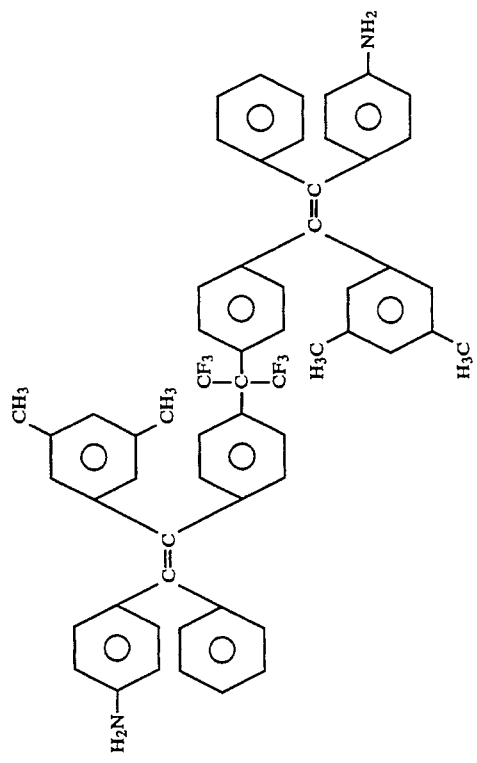

-continued
(21)
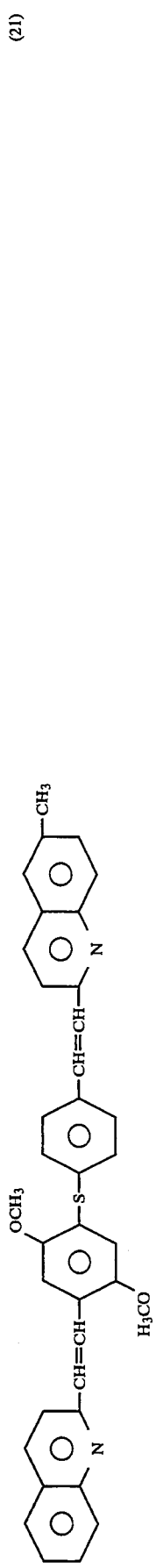
(22)
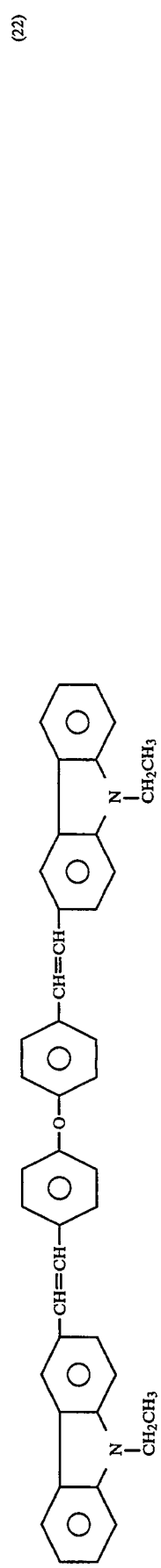
(23)
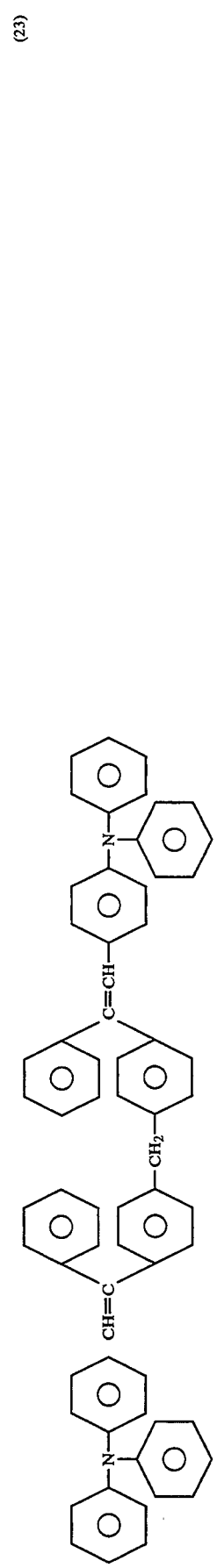
(24) (25)
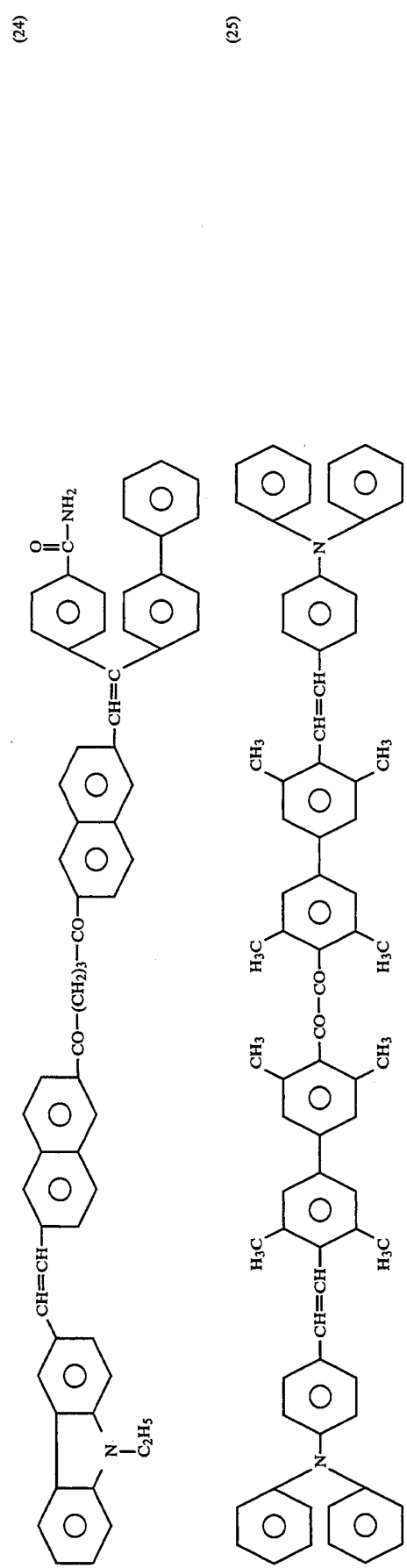

(26) 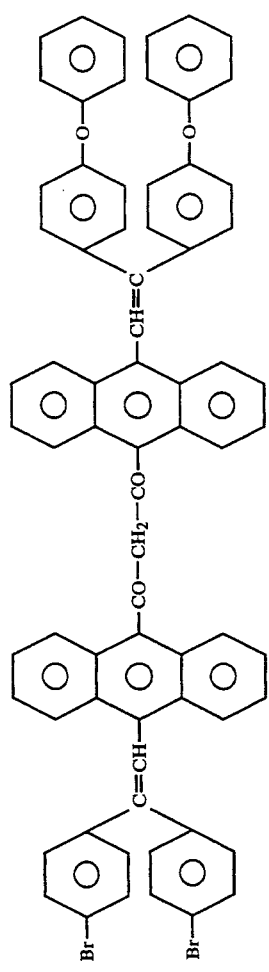
(27) 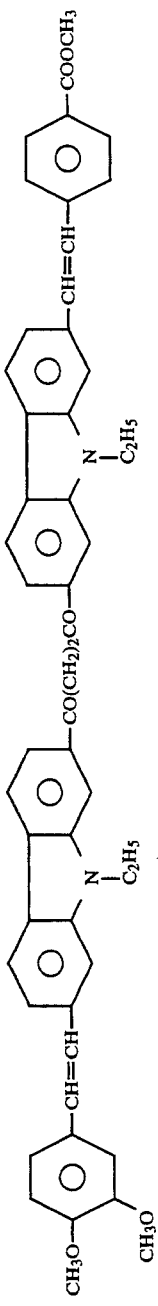
(28) 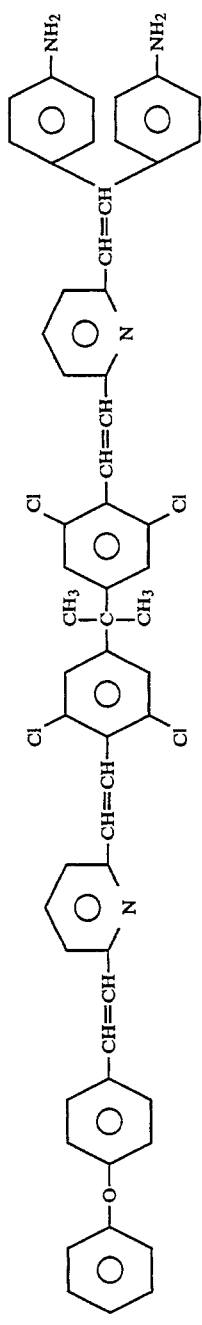
(29) 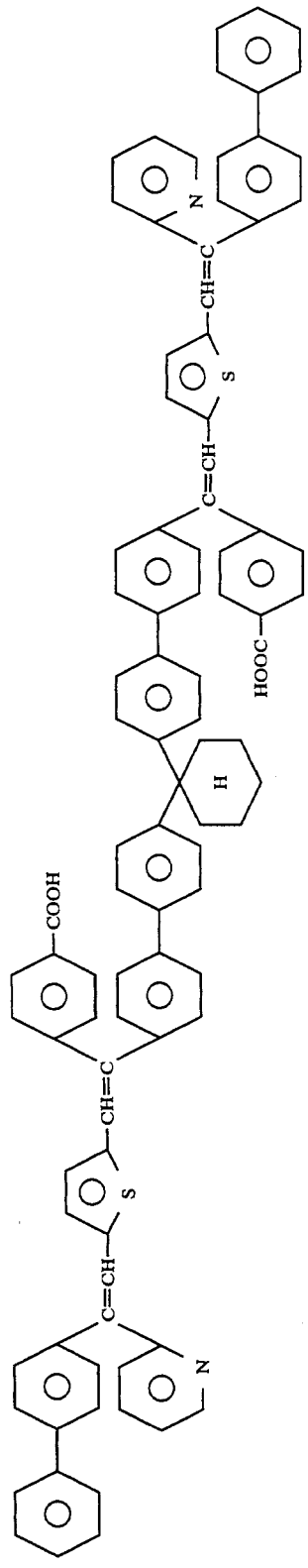

(30) (31) (32) (33)
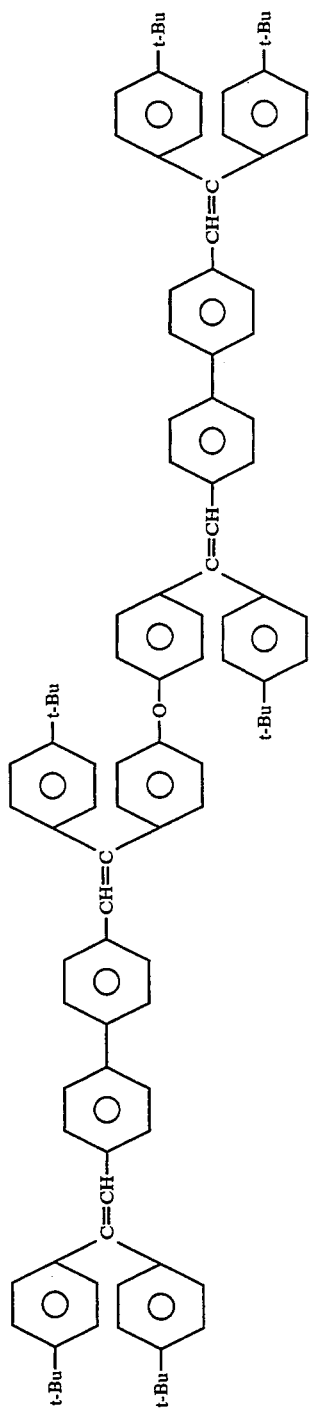
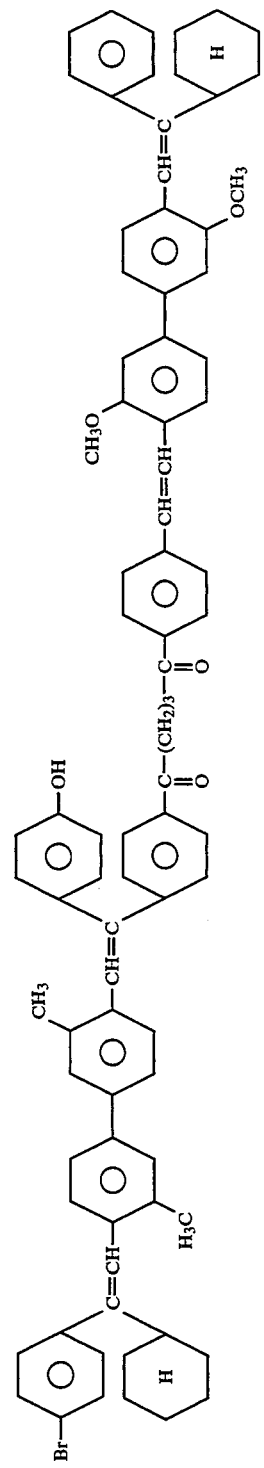
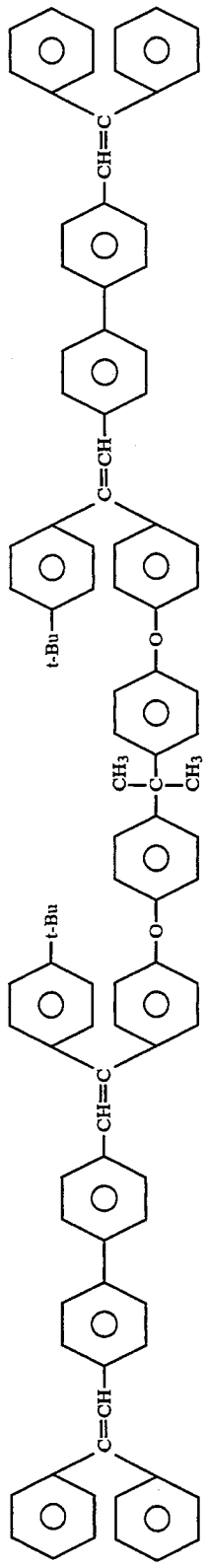
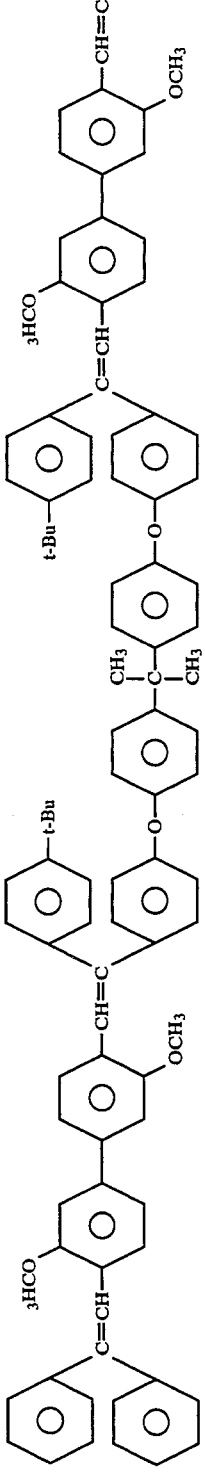
(t-Bu; tertiarybutyl)

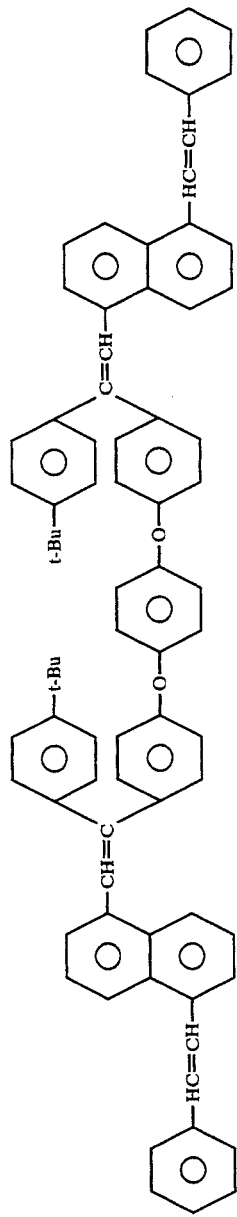
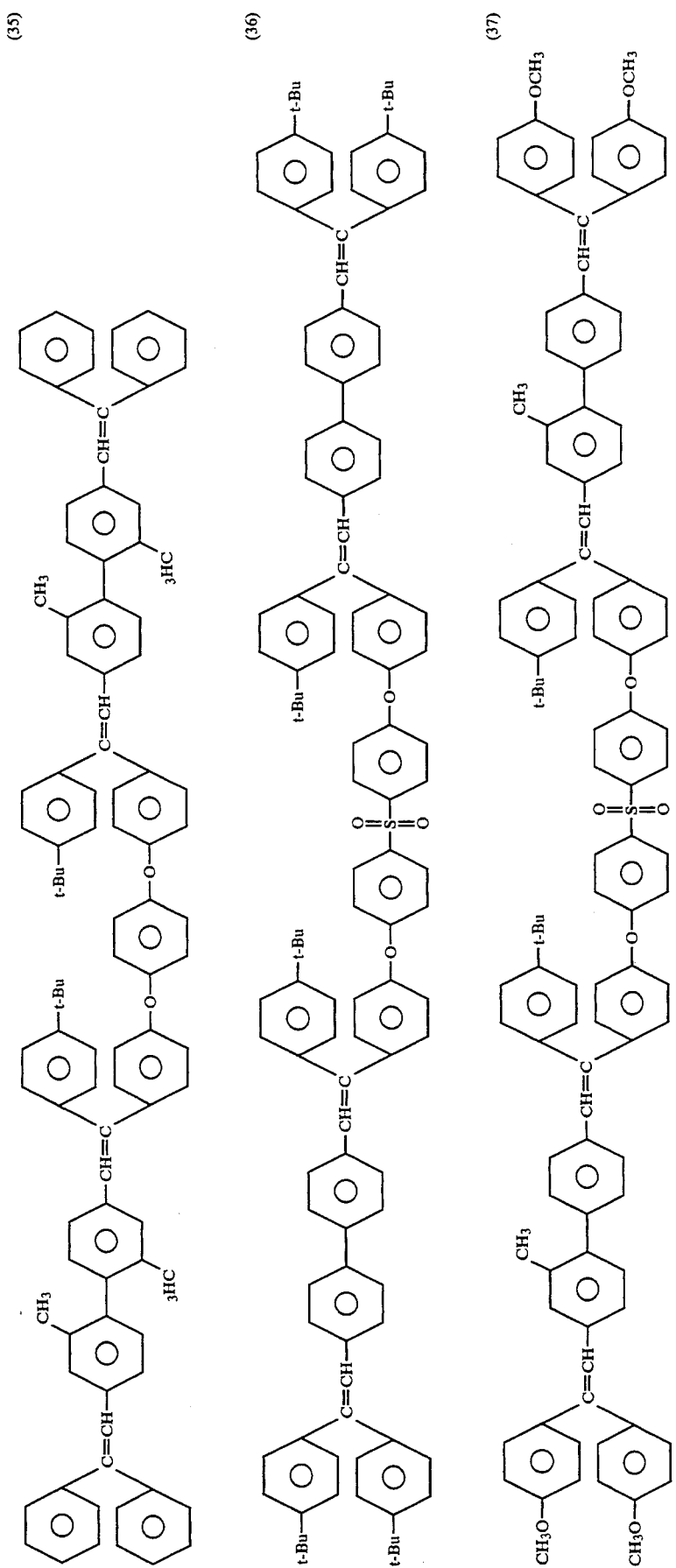

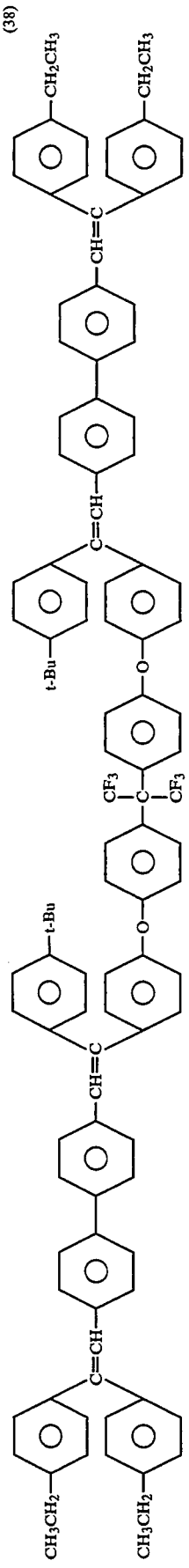
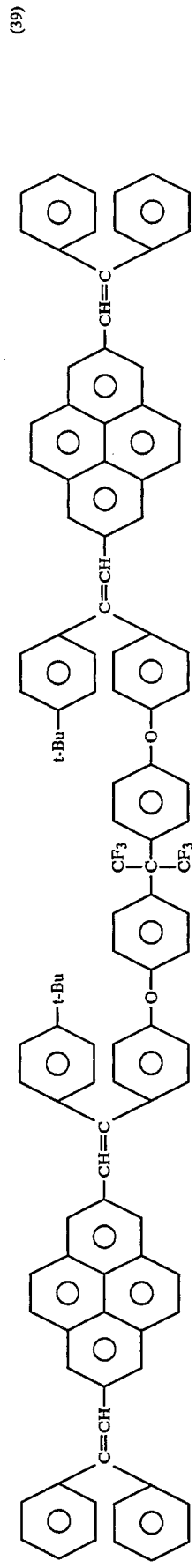
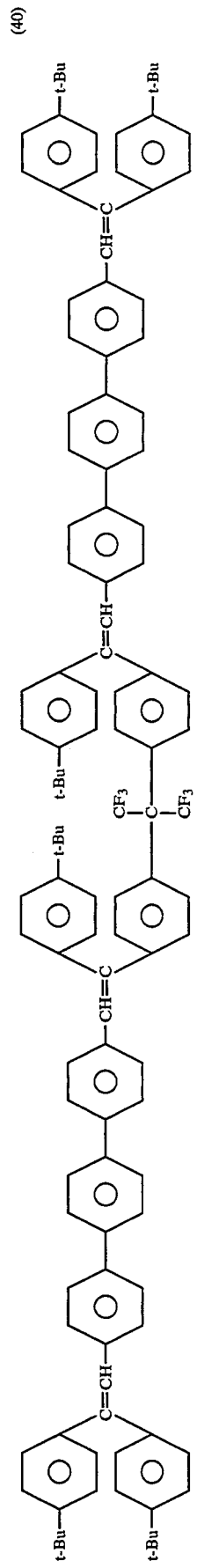

(41)
(42)
(43)
(44)
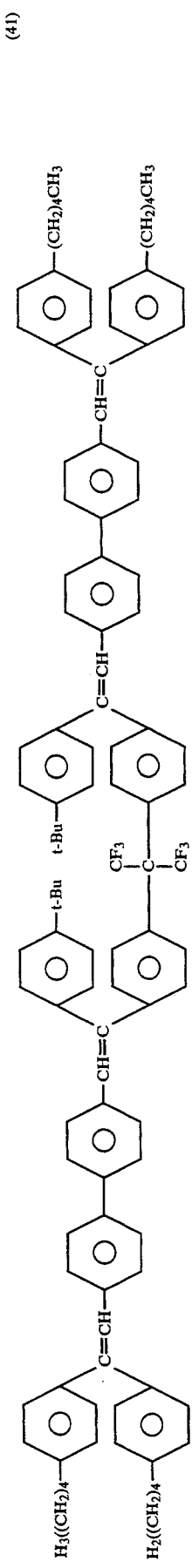
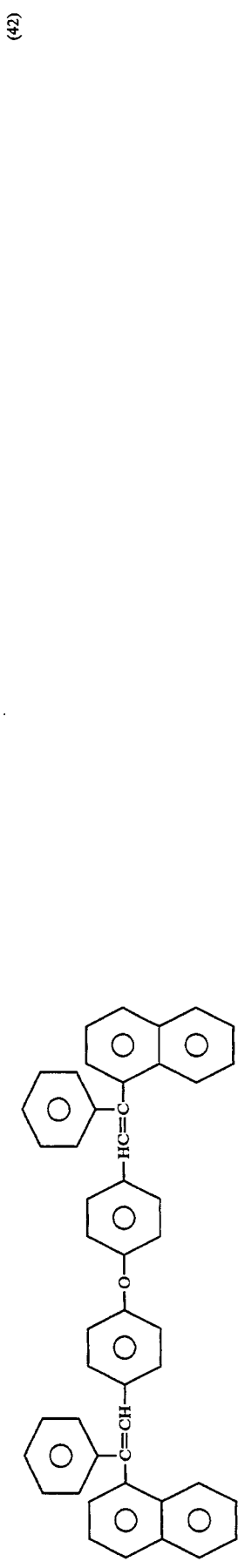
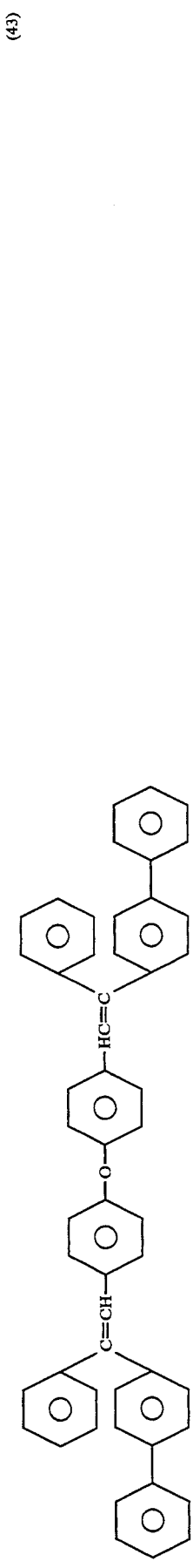
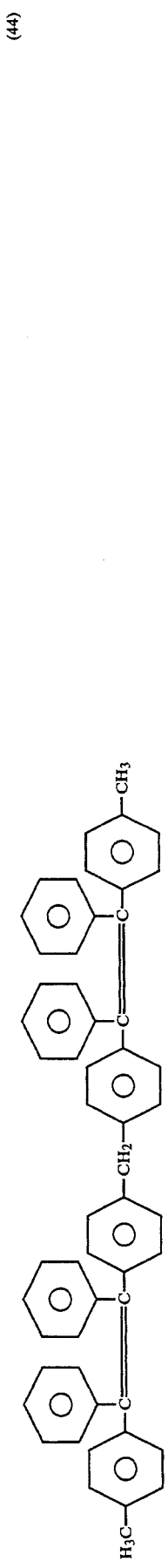

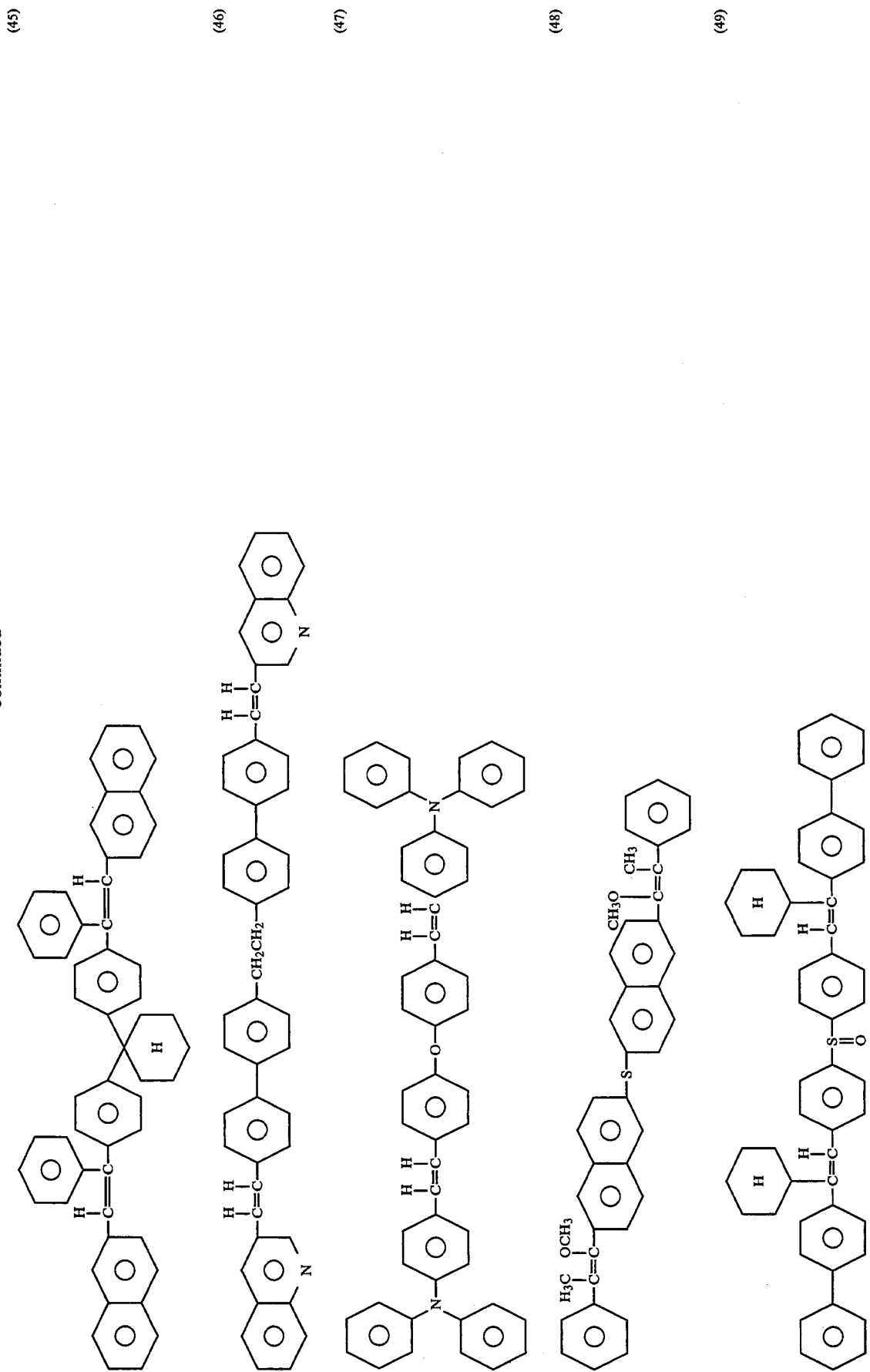

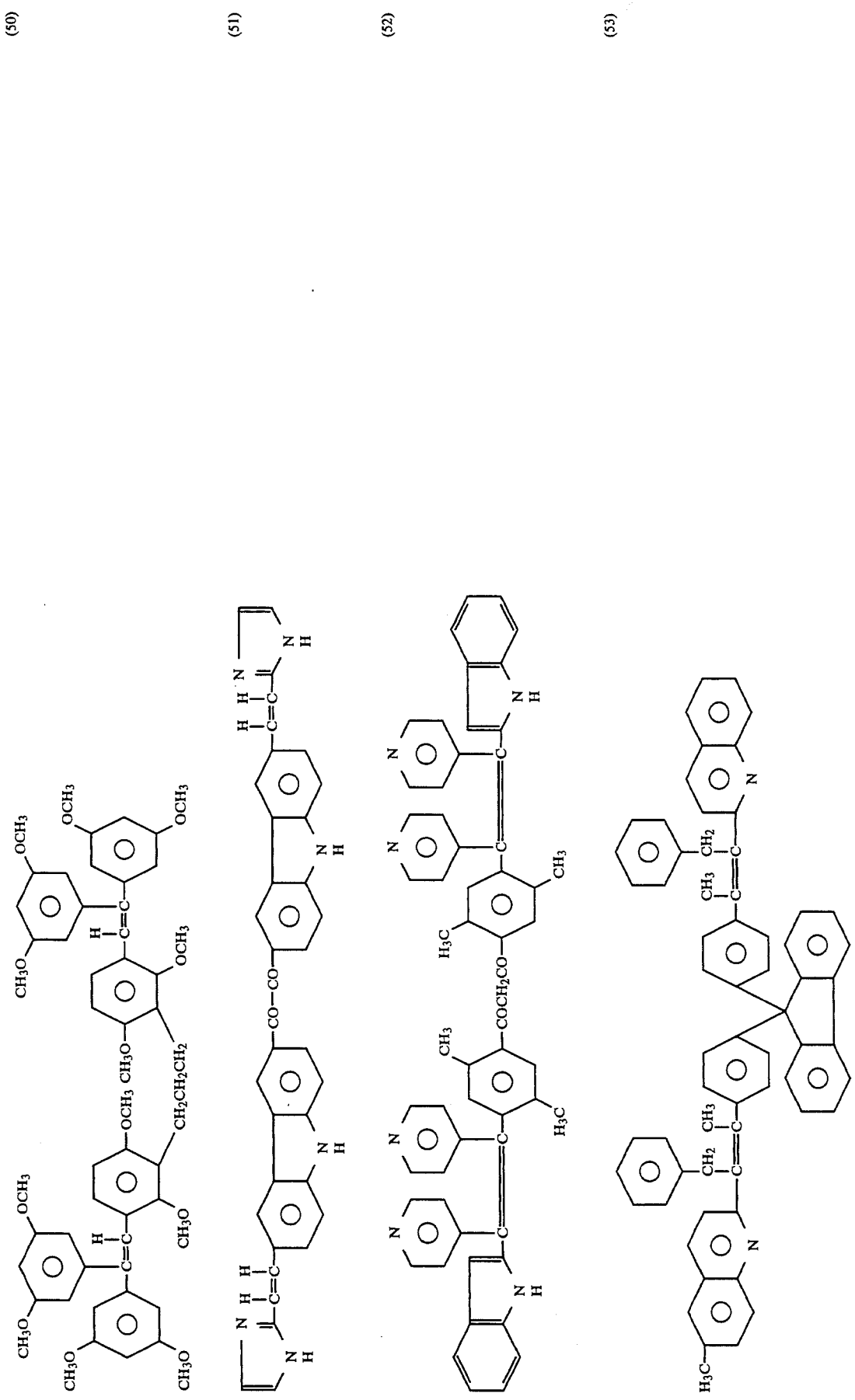

-continued
(54)
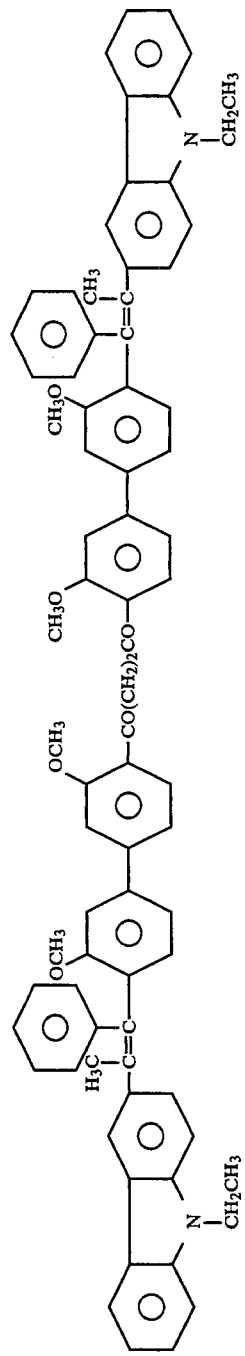
(55)
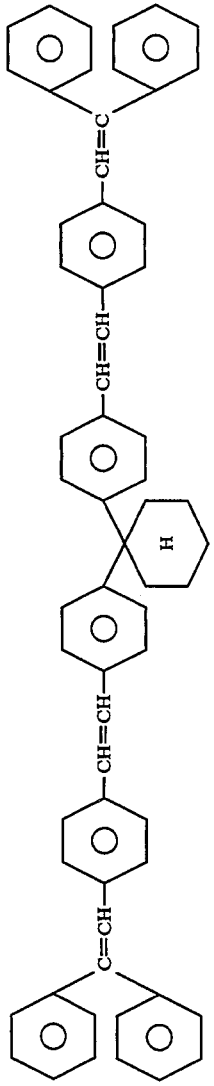
(56)
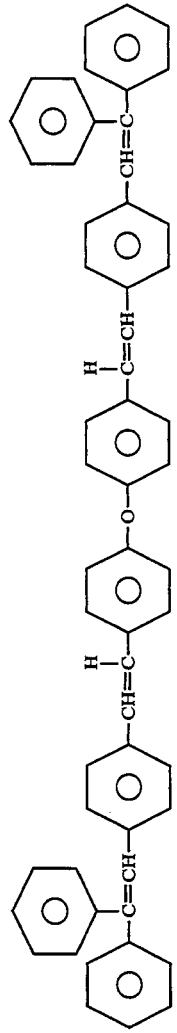
(57)
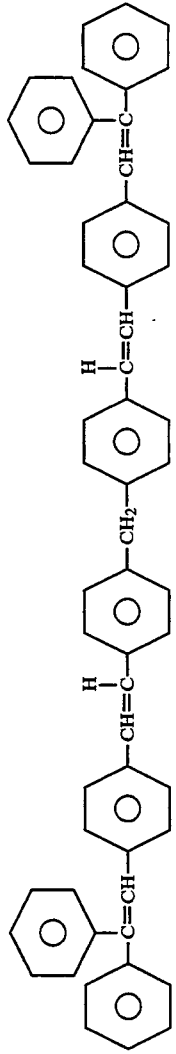
(58)
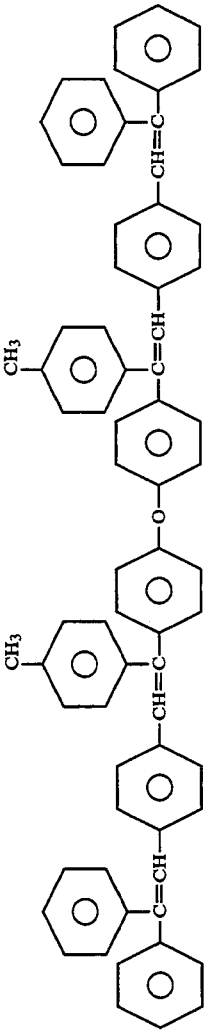

-continued
(59) 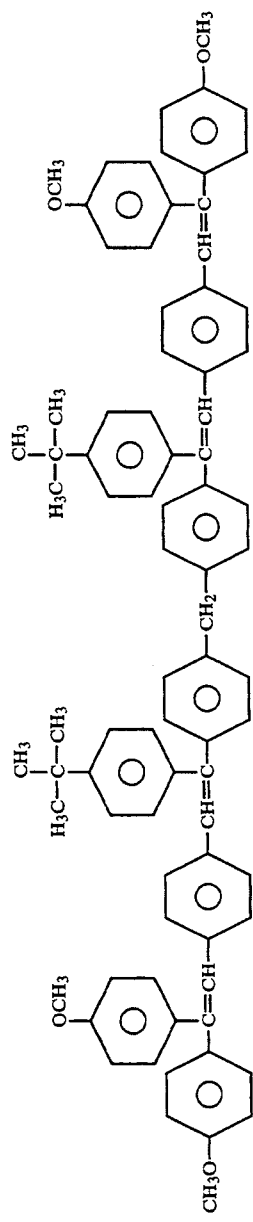
(60) 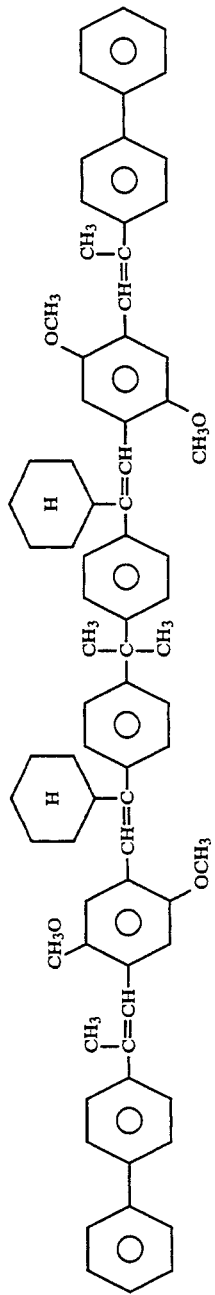
(61) 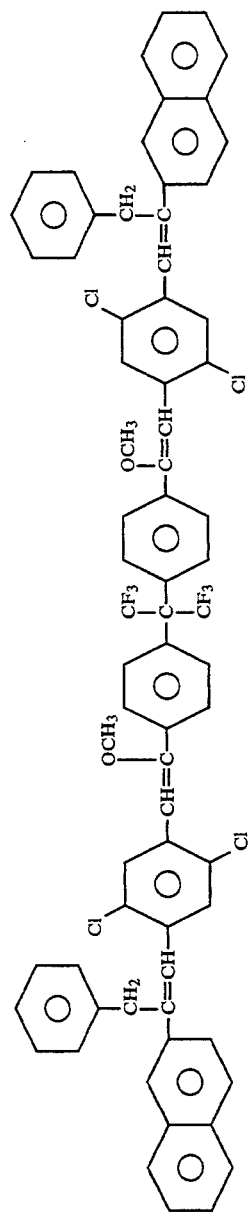
(62) 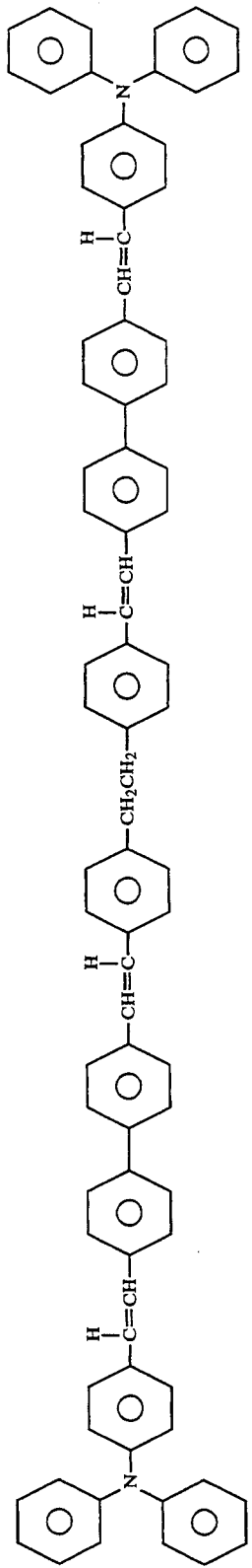

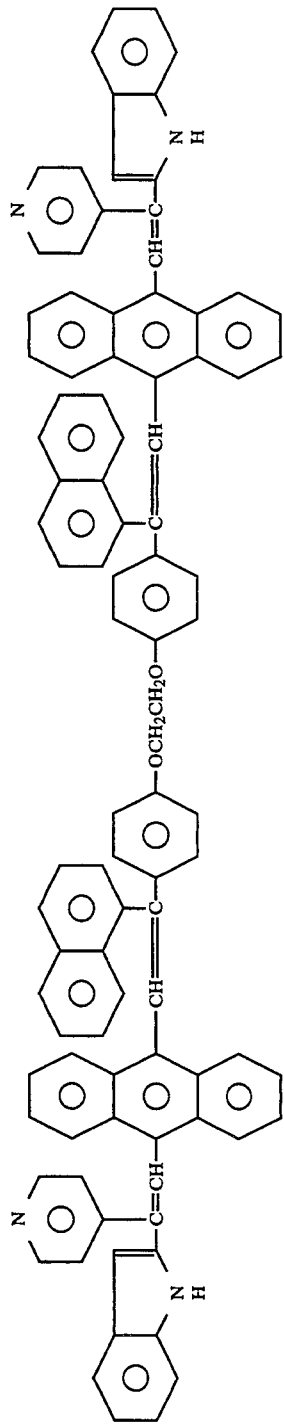
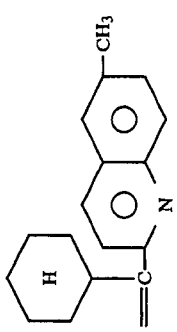
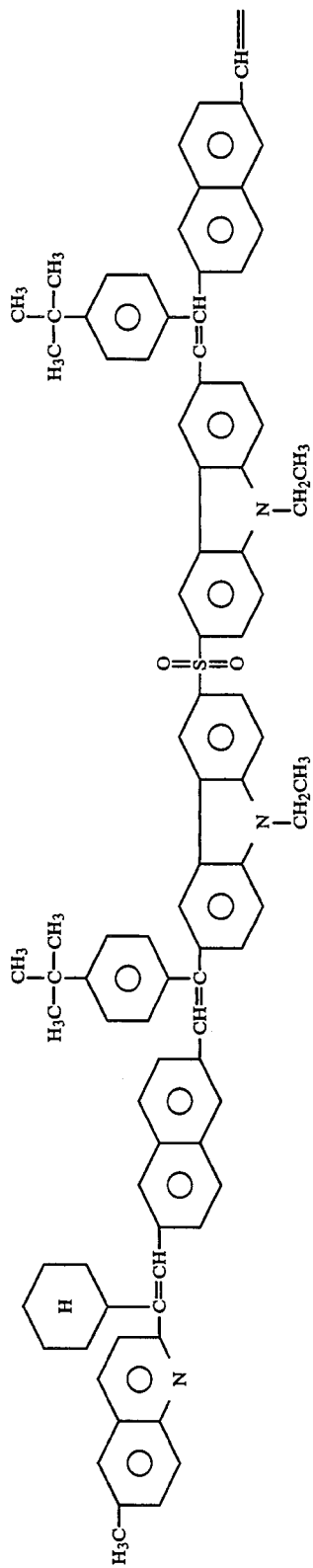

-continued
(66)
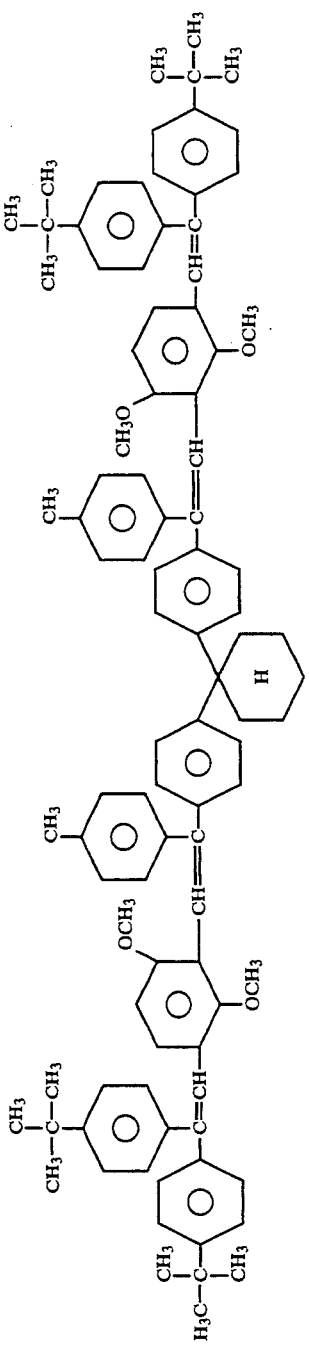
(67)
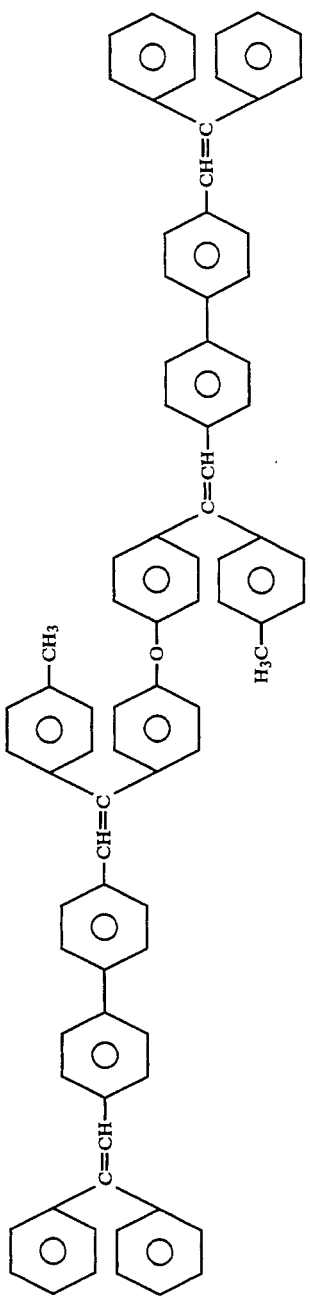
(68)
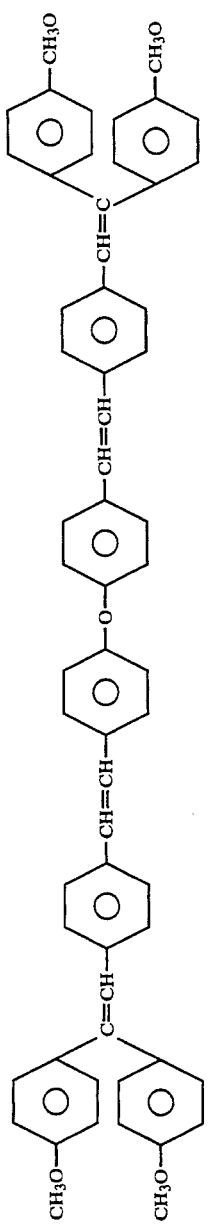

-continued
(69) 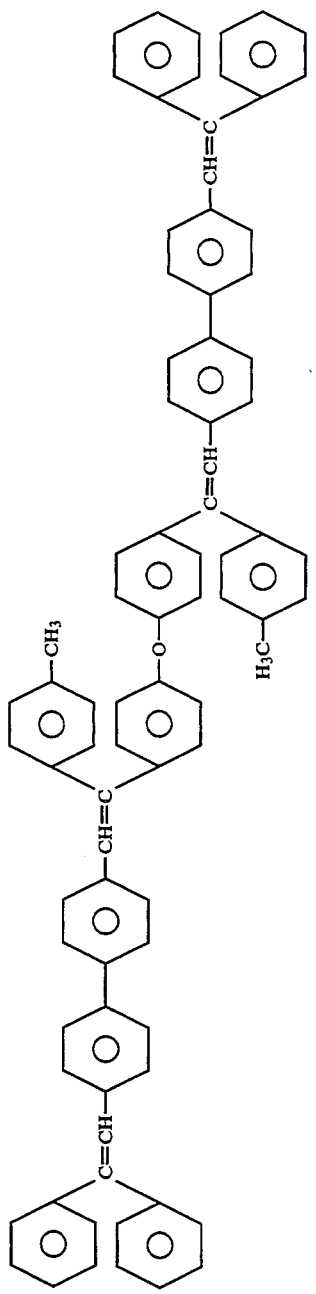 (70) 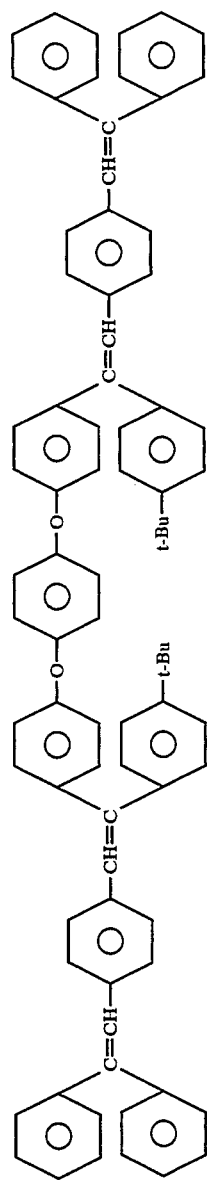 (71) 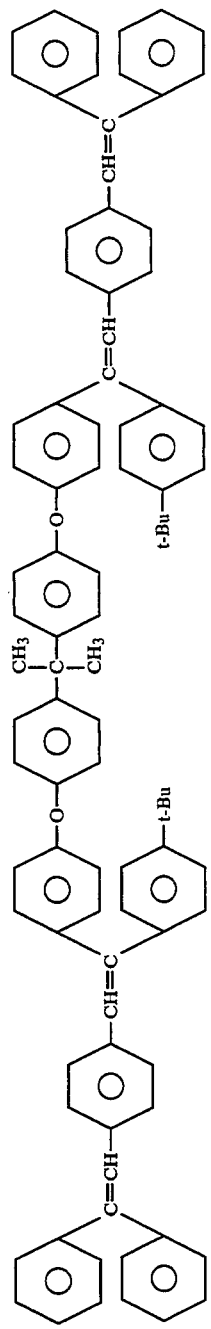 (72) 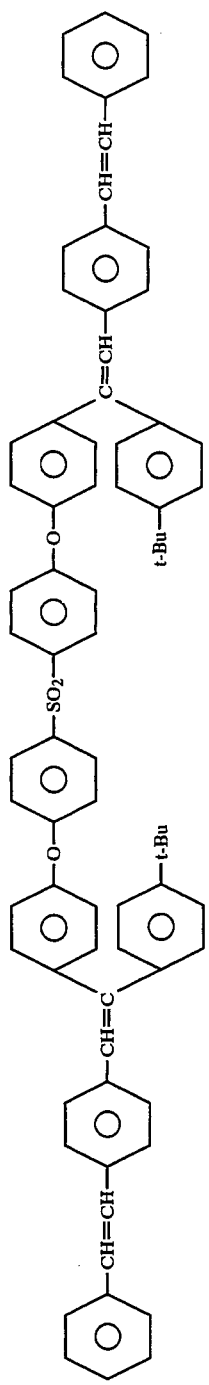

(73) (74) (75) (76)
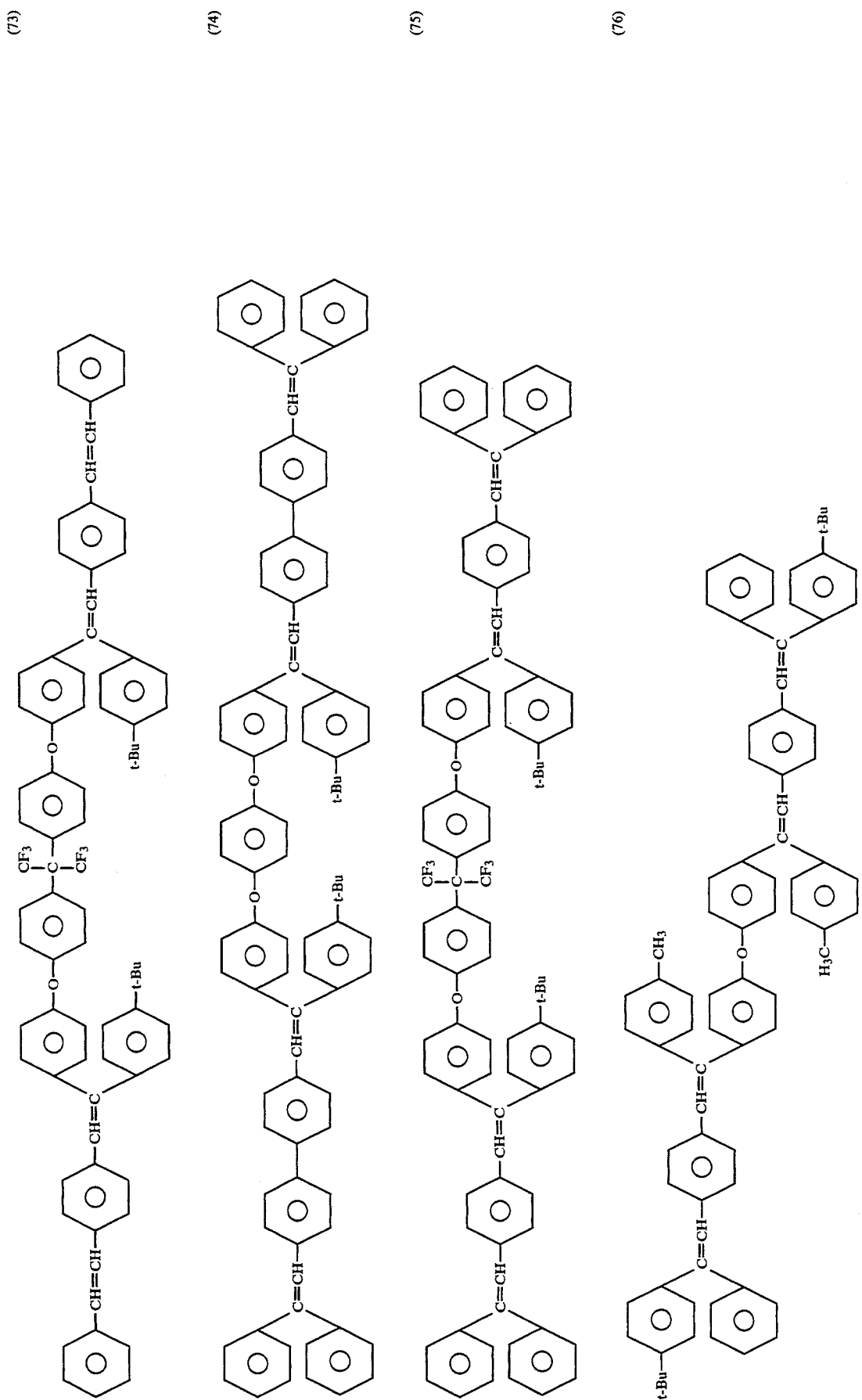
-continued

(77)
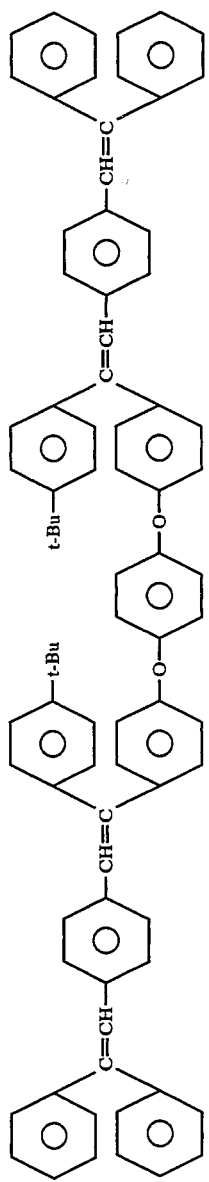

In the present invention, the compound represented by the general formula (c):
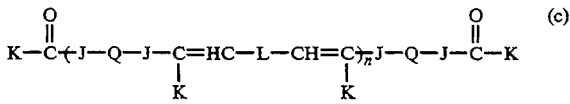
(wherein J, K, L and Q are the same as defined above. n is an integer of 1 to 5) can be used as a light emitting material.
Specific examples of the compounds represented by the general formula (c) are shown below.

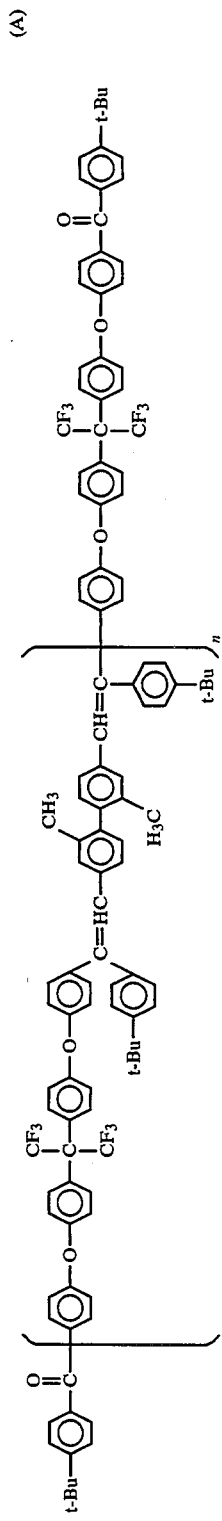
(A)
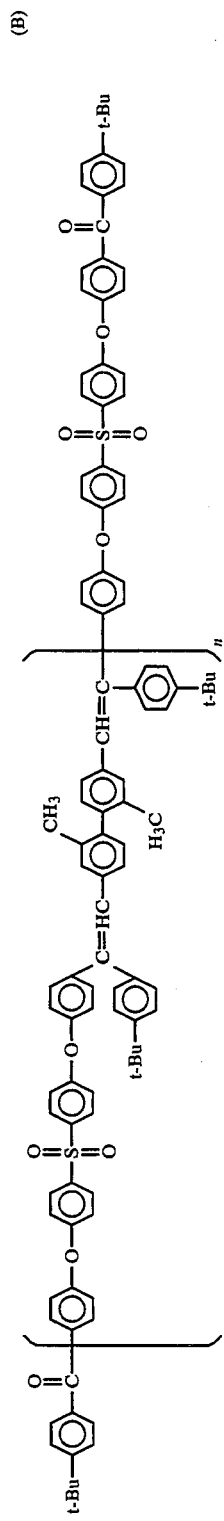
(B)
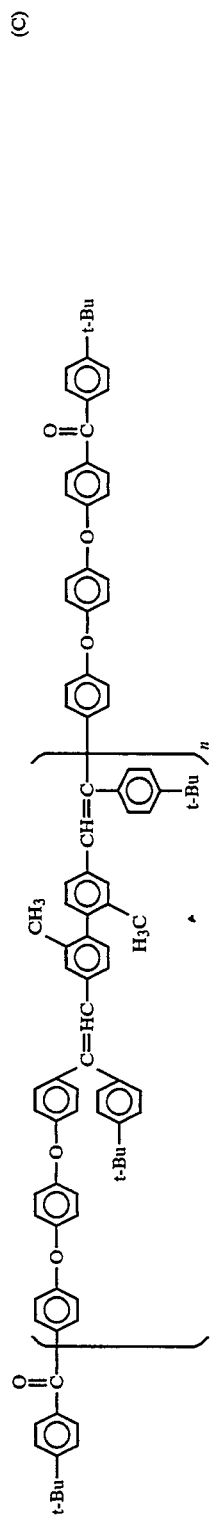
(C)
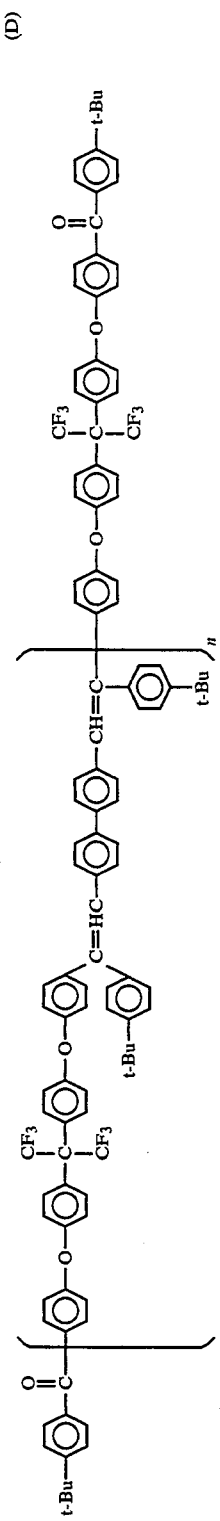
(D)

-continued
(E) 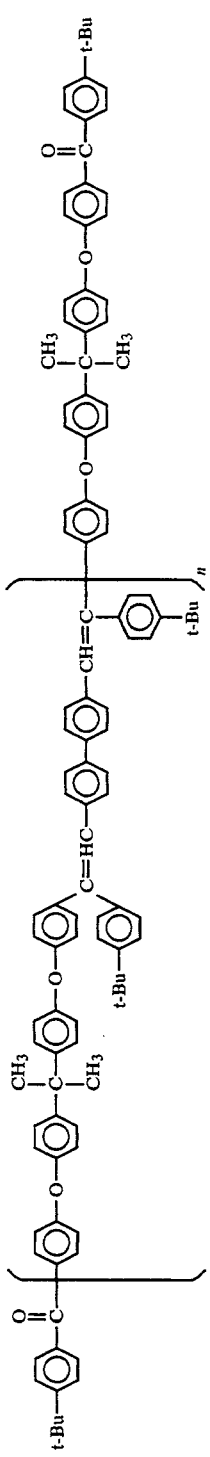
(F) 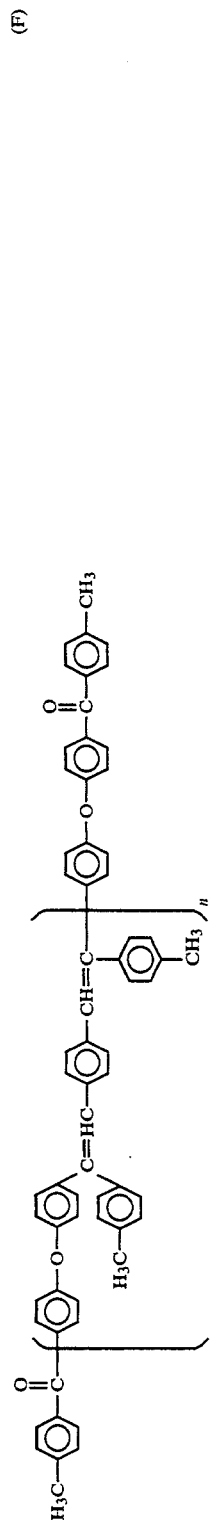
(G) 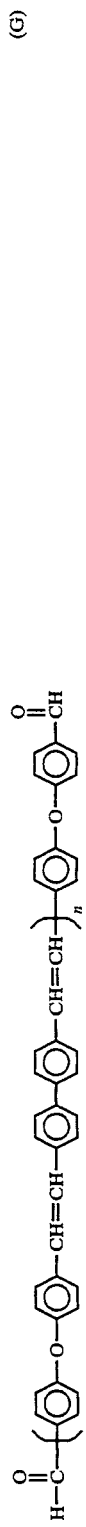
(H) 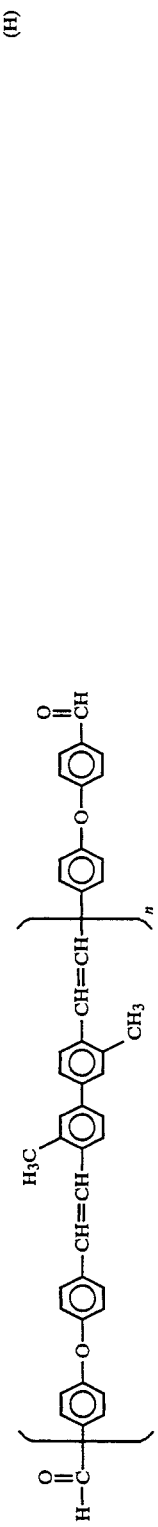
(I) 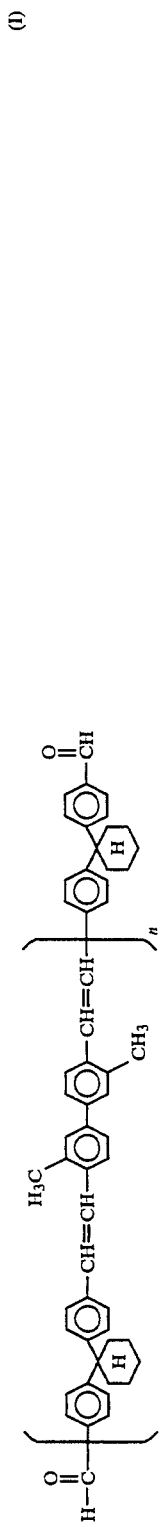
(J) 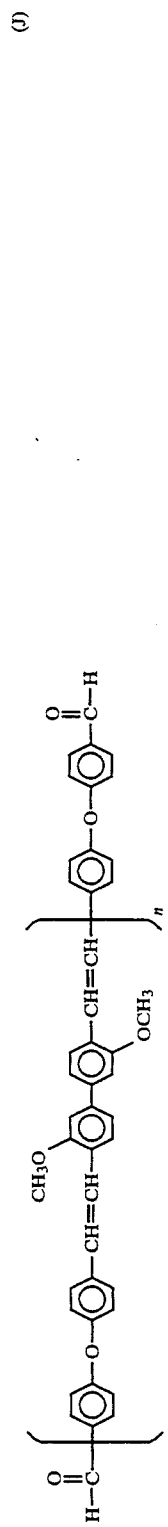

-continued
(K) 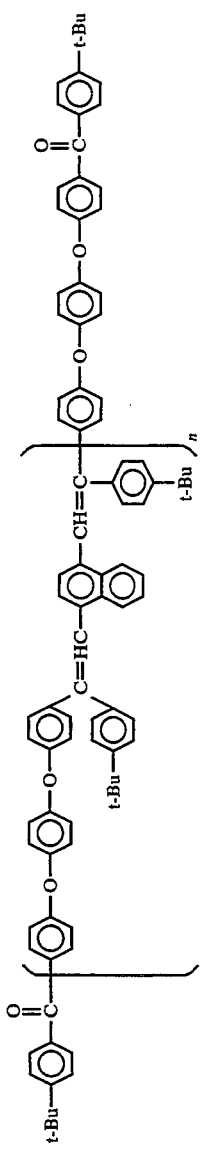
(L) 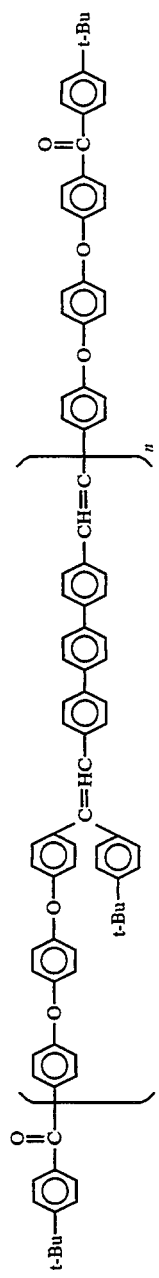

As described above, the compound represented by the general formula (a) or (b) include various ones, but the general ones are symmetrical dimerized styryl compounds represented by the general formula (d) or (e):

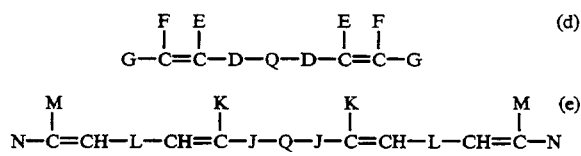

(wherein D, E, F, G, J, K, L, M, N and Q are the same as defined above).

The light emitting layer in the EL device of the present invention can be prepared by forming the compound represented by the above general formula (a), (b) or (c) into thin film by a known method such as the vapor deposition method, the spin-coating method, the casting method or the LB method. Particularly, a molecular accumulated film means a thin film formed by depositing said compound from a gaseous state, or a thin film formed by solidification of said compound from a solution or liquid state. Usually, said molecular accumulated film is distinguished from a thin film (molecular built-up film) formed by the LB method, by the difference in the aggregation structure or the higher-order structure, or the functional difference resulting therefrom.

Said light emitting layer, as disclosed in Japanese Patent Application Laid-Open No. 194393/1984, can be formed by dissolving a binding agent such as a resin and said compound in a solvent to prepare solution, which is formed into thin film by the spin-coating method and the like.

The film thickness of the light emitting layer thus formed is not particularly limited, and can be determined appropriately according to the circumstances. Usually, it is preferably in the range of 5 nm to 5 µm.

The light emitting layer in the EL device of the present invention has an injection function of injecting holes from an anode or a hole-injecting and -transporting layer, and electrons from a cathode or an electron-injecting and -transporting layer upon application of an electric field, a transport function of transporting injected charges (holes and electrons) by the action of an electric field, and a light emitting function of providing a field for recombination of electrons and holes, thereby emitting light. There may be a difference in ease between hole injection and electron injection, and a difference in transport ability represented by mobilities of holes and electrons, but it is preferably to move either one of the charges.

Generally, in the compound represented by the above general formula (a), (b) or (c) to be used as said light emitting layer, since the ionization potential is smaller than 6.0 eV or so, holes can be injected relatively easily when the proper metal or compound is chosen as an anode.

Since the electron affinity is larger than 2.8 eV or so, electrons can be injected relatively easily, and besides, the function of transporting electrons and holes is excellent when the proper metal or compound is chosen as a cathode. Moreover, since said compound has a strong fluorescence in the solid state, it has a high ability to transform the excited states of said compound formed upon recombination of electrons with holes, its aggregate or its crystal into light.

There are various embodiments of the structure of the EL device of the present invention. Basically, the above light emitting layer is sandwiched between a pair of electrodes (anode and cathode), and if necessary, a hole-injecting and -transporting layer or an electron-injecting and -transporting layer may be interposed between them. Specific examples of the structure are; (1) anode/light emitting layer/cathode, (2) anode/hole-injecting and -transporting layer/light emitting layer/cathode, (3) anode/hole-injecting and -transporting layer/light emitting layer/electron-injecting and -transporting layer/cathode, and (4) anode/light emitting layer/electron-injecting and -transporting layer/cathode.

Said hole-injecting and -transporting layer and said electron-injecting and -transporting layer are not always necessary, but these layers improve light emitting property more greatly.

It is preferable that any EL device having the above structure be supported by the substrate. Said substrate is not particularly limited. Substrates conventionally used for an organic EL device, for example, substrates composed of glass, transparent plastic, or quartz can be used.

As to the anode in the organic EL device of the present invention, a metal, an alloy, an electro-conducting compound or a mixture thereof, all having a large work function (not less than 4 eV), is preferably used as an electrode material. Specific examples of electrode materials are metals such as Au, and an electro-conductive transparent materials such as CuO, ITO, SnO$_2$, and ZnO. Said anode can be prepared by forming said electrode material into thin film by vapor deposition or sputtering. To obtain light emission from said electrode, it is preferable that the transmittance be more than 10% and the resistance of the sheet as an electrode be not more than several hundred Ω/□.

The film thickness is usually in the range of 10 nm to 1 µm, preferably 10 to 200 nm, depending upon the material.

On the other hand, as to the cathode, a metal, an alloy, an electroconductive compound or a mixture thereof, all having a small work function (not more than 4 eV) is preferably used as an electrode material. Specific examples of such electrode materials are sodium, a sodium-potassium alloy, magnesium, lithium, a mixture of magnesium and copper, Al/AlO$_2$, and indium. Said cathode can be prepared by forming said electrode material into thin film by vapor deposition or sputtering. The resistance of the sheet as an electrode is preferably not more than several hundred Ω/□. The film thickness is usually in the range of 10 nm to 1 µm, preferably 50 to 200 nm. In the EL device of the present invention, though not prescribed, it is preferable that either anode or cathode be transparent or translucent because light emission is transmitted and obtained with high efficiency.

As described above, there are various embodiments of the structure in the EL device of the present invention. The hole-injecting and -transporting layer in the EL device having the above structure (2) or (3) is a layer comprising a hole-transporting compound and has a function of transporting holes injected from the anode to the light emitting layer. By interposing said hole-injecting and -transporting layer between the anode and the light emitting layer, more holes are injected into the light emitting layer at lower voltage, and besides, electrons injected into the light emitting layer from the cathode or the electron-injecting and -transporting layer are accumulated in the vicinity of the interface in the light emitting layer due to the electron barrier existing in the interface between the light emitting layer and the hole-injecting and -transporting layer, thereby improving light emission efficiency to form a device having excellent light emitting performance.

The hole-transporting compound to be used as the above hole-injecting and -transporting layer is, when placed between two electrodes where an electric field is applied and holes are injected from the anode, preferably able to properly transport said holes to the light emitting layer, and has a hole mobility of at least $10^{-6}$ cm$^2$/V·S when an electric field of $10^4$ to $10^6$ V/cm is applied.

Said hole-transporting compound is not particularly limited, so long as it has preferable properties as described above, and any compound can be used selected from those used conventionally as the charge-transporting materials for holes in photoconductive materials, or known compounds used for hole-injecting and -transporting layers of EL devices.

Examples of said charge-transporting material are triazole derivatives (described in the specification of U.S. Pat. No. 3,112,197, etc.), oxadiazole derivatives (described in the specification of U.S. Pat. No. 3,189,447, etc.), imidazole derivatives (described in Japanese Patent Publication No. 16096/1962, etc.), polyarylalkane derivatives (described in the specifications of U.S. Pat. Nos. 3,615,402, 3,820,989 and 3,542,544, and in Japanese Patent Publication Nos. 555/1970 and 10983/1976, and further in Japanese Patent Application Laid-Open Nos. 93224/1976, 17105/1980, 4148/1981, 108667/1980, 156953/1980 and 36656/1981, etc.), pyrazoline derivatives or pyrazolone derivatives (described in the specifications of U.S. Pat. Nos. 3,180,729 and 4,278,746, and in Japanese Patent Application Laid-Open Nos. 88064/1980, 88065/1980, 105537/1974, 51086/1980, 80051/1981, 88141/1981, 45545/1982, 112637/1979 and 74546/1970, etc.), phenylenediamine derivatives (described in the specification of U.S. Pat. No. 3,615,404, and in Japanese Patent Publication Nos. 10105/1976, 3712/1971 and 25336/1972, and further in Japanese Patent Application Laid-Open Nos. 53435/1979, 110536/1979 and 119925/1979, etc.), arylamine derivatives (described in the specification of U.S. Pat. Nos. 3,567,450, 3,180,703, 3,240,597, 3,658,520, 4,232,103, 4,175,961 and 4,012,376, and in Japanese Patent Publication Nos. 35702/1974 and 27577/1964, and further in Japanese Patent Application Laid-Open Nos. 144250/1980, 119132/1981 and 22437/1981, and German Patent No. 1,110,518, etc.), amino-substituted chalcone derivatives (described in the specification of U.S. Pat. No. 3,526,501, etc.), oxazole derivatives (described in the specification of U.S. Pat. No. 3,257,203, etc.), styrylanthracene derivatives (described in Japanese Patent Application Laid-Open No. 46234/1981, etc.), fluorenone derivatives (described in Japanese Patent Application Laid-Open No. 110837/1979, etc.), hydrazone derivatives (described in the specification of U.S. Pat. No. 3,717,462, and in Japanese Patent Application Laid-Open Nos. 59143/1979, 52063/1980, 52064/1980, 46760/1980, 85495/1980, 11350/1982 and 148749/1982, etc.), and stilbene derivatives (described in Japanese Patent Application Laid-Open Nos. 210363/1986, 228451/1986, 14642/1986, 72255/1986, 47646/1987, 36674/1987, 10652/1987, 30255/1987, 93445/1985, 94462/1985, 174749/1985, and 175052/1985, etc.)

In the present invention, the above compounds can be used as a hole-transporting compound, but it is preferred to use porphyrin compounds (described in Japanese Patent Application Laid-Open No. 2956965/1988, etc.), aromatic tertiary amine compounds or styrylamine compounds (described in the specification of U.S. Pat. No. 4,127,412, and Japanese Patent Application Laid-Open Nos. 27033/1978, 58445/1979, 149634/1979, 64299/1979, 79450/1980, 144250/1980, 119132/1981, 295558/1986, 98353/1986 and 295695/1988), and most preferably, said aromatic tertiary amine compounds are used.

Representative examples of said porphyrin compounds are porphyrin; 1,10,15,20-tetraphenyl-21H,23H-porphyrin copper (II), 1,10,15,20-tetraphenyl-21H,23H-porphyrin zinc (II), 5,10,15,20-tetrakis(pentafluorophenyl)-21H,23H-porphyrin, siliconphthalocyanine oxide, aluminum phthalocyanine chloride, phthalocyanine (nonmetal), dilithium phthalocyanine, copper tetramethylphthalocyanine, copper phthalocyanide, chrome phthalocyanine, zinc phthalocyanine, lead phthalocyanime, titanium phthalocyanine oxide, magnesium phthalocyanine, and copper octamethylphethalocyanine.

Representative examples of said aromatic tertiary amine compounds or styrylamine compounds are
N,N,N',N'-tetraphenyl-4,4'-diaminophenyl
N,N'-diphenyl-N,N'-di(3-methylphenyl)-4,4'-diaminobiphenyl,
2,2-bis(4-di-p-tolylaminophenyl)propane,
1,1-bis(4-di-p-tolylaminophenyl)-cyclohexane,
N,N,N',N'-tetra-p-tolyl-4,4'-diaminobiphenyl,
1,1-bis(4-di-p-tolylaminophenyl)-4-phenylcyclohexane,
bis(4-dimethylamino-2-methylphenyl)phenylmethane,
bis(4-di-p-tolylaminophenyl)phenylmethane,
N,N'-diphenyl-N,N'-di(4-methoxyphenyl)-4,4'-diaminobiphenyl,
N,N,N',N'-tetraphenyl-4,4'-diaminodiphenylether,
4,4'-bis(diphenylamino)quadriphenyl, N,N,N-tri(p-tolyl)amine,
3-(di-p-tolylamino)-4'-[4(di-p-tolylamino)styryl]stilbene,
4-N,N-diphenylamino-(2-diphenylvinyl)benzene,
3-methoxy-4'-N,N-diphenylaminostilbene, and N-phenylcarbazole.

Said hole-injecting and -transporting layer in the EL device of the present invention may be made up of one layer comprising one, or two or more hole-transporting compounds, or a laminate of hole-injecting and -transporting layers comprising different compounds from those of the above layer.

On the other hand, the electron-injecting and -transporting layer in the EL device having the above structure (3) comprises an electron-transporting compound, and has a function of transporting electrons injected from the cathode to the light emitting layer. Said electron-transporting compound is not particularly limited, and any compound can be used selected from the conventionally known compounds.

Preferable examples of said electron-transporting compound are nitro-substituted fluorenone derivatives such as:

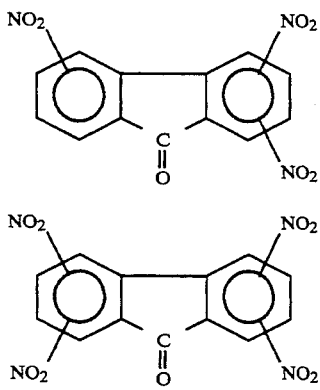

thiopyrandioxide derivatives such as:

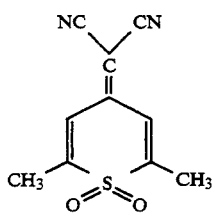

diphenylquinone derivatives such

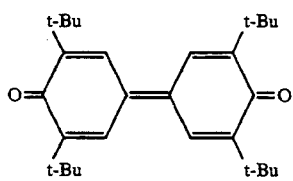

(described in Polymer Preprints, Japan, Vol. 37, No. 3, p. 681 (1988), etc.), compounds such as:

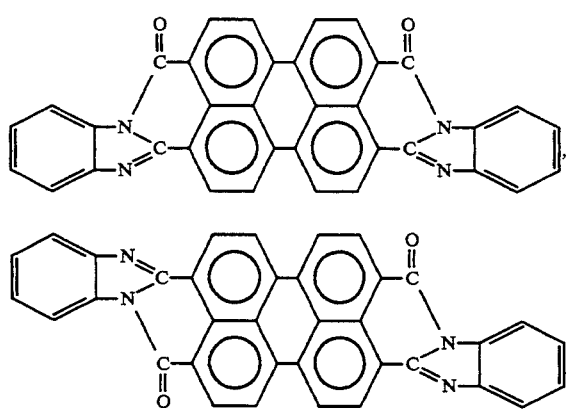

(described in J. J. Appl. Phys., Vol. 27, p. 269 (1988), etc.), anthraquinodimethane derivatives (described in Japanese Patent Application Laid-Open Nos. 149259/1982, 55450/1983, 225151/1986, 233750/1986 and 104061/1988, etc.), fluorenylidenemethane derivatives (described in Japanese Patent Application Laid-Open Nos. 69657/1985, 143764/1986, 148159/1986, etc.), anthrone derivatives (described in Japanese Patent Application Laid-Open Nos. 225151/1986 and 233750/1986, etc.), and oxadiazole derivatives disclosed in appl. Phys. Lett., Vol. 55, p.1489 (1989) such as:

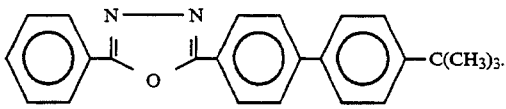

Subsequently, the preferable process for preparing an EL device of the present invention will be explained with examples of each device having each structure. The EL device comprising the above structure of anode/light emittimg layer/cathode is prepared in the following manner. First, on the proper substrate, a thin film comprising the desired electrode material, for example, the material for am anode is formed in a thickness of not more than 1/μm, preferably in the range of 10 to 200 nm by vapor deposition or sputtering to prepare an anode. Then, on said anode, the compound represented by the general formula (a) as a light emitting material is formed into thin film to prepare a light emitting layer. As the method of forming said light emitting material into thin film, for example, the spin-coating method, the casting method, the LB method and the vapor deposition method can be used. The vapor deposition method is preferable in that a uniform thin film can be obtained and pinholes are less likely to be formed. When said vapor deposition method is employed for forming said light emitting material into thin film, the conditions of vapor deposition vary depending upon the kind of the light emitting material to be used, or the desired crystal structure and the aggregation structure of the molecular accumulated film. Usually, it is preferred to select conditions appropriately in the following ranges; a temperature for heating boat of 50° to 400° C., a pressure of $10^{-5}$ to $10^{-3}$ Pa, a vapor deposition rate of 0.01 to 50 nm/sec, a substrate temperature of $-50°$ to $+300°$ C., and a film thickness of 5 nm to 5 μm. After said light emitting layer is formed, a thin film comprising an electrode material for a cathode is formed therein in a thickness of not more than 1 μm, preferably 50 to 200 nm to prepare a cathode, whereupon the desired EL device can be obtained. Said EL device can be prepared in reverse order, that is, in order of a cathode, a light emitting layer and an anode.

Subsequently, the process for preparing an EL device comprising anode/hole-injecting and -transporting layer/light emitting layer/cathode will be explained. First, an anode is formed in the same manner as in the above EL device, and then a thin film comprising a hole-transporting compound is formed thereon by the vapor deposition method to prepare a hole-injecting and -transporting layer. In this case, the conditions of vapor deposition are selected according to those of forming a thin film of the above light emitting material. Then, on said hole-injecting and -transporting layer, a light emitting layer and a cathode are prepared in turn in the same manner as in preparing the above EL device, whereupon the desired EL device can be obtained.

Said EL device can be prepared in reverse order, that is, in order of a cathode, a light emitting layer, a hole-injecting and -transporting layer, and an anode.

Moreover, the process for preparing an EL device comprising anode/hole-injecting and -transporting layer/light emitting layer/electron-injecting and -transporting layer/cathode will be explained. First, an anode, a hole-injecting and -transporting layer and a light emitting layer are prepared in turn in the same manner as in preparing the above EL device, and then on said light emitting layer, a thin film comprising an electron-transporting compound is formed by the vapor deposition method to prepare an electron-injecting layer. Then, on said layer, a cathode is prepared in the same manner as in preparing the above EL device, whereupon the desired EL device can be obtained.

Said EL device can be prepared in reverse order, that is, in order of a cathode, an electron-injecting and -transporting layer, a light emitting layer, a hole-injecting and -transporting layer, and an anode.

When a DC voltage of about 1 to 30 V is applied to the EL device thus obtained, with an anode being polarity (+) and a cathode being polarity (−), an emission of light is observed on the side of transparent or translucent electrode. When a voltage is applied with the opposite polarity, no electric current flows and no emission of light is obtained. When AC voltage is applied, an emission of light is obtained only with an anode being (+) and a cathode being (−). Any wave form of AC voltage may be applied.

Subsequently, the mechanism of light emission in said EL device is described taking the structure of anode/-hole-injecting and -transporting layer/light emitting layer/cathode as an example. Upon applying voltage with the above anode being polarity (+) and the above cathode being polarity (−), holes are injected into the hole-injecting and -transporting layer from said anode by the action of an electric field.

Said injected holes are transported to the interface of the light emitting layer through said hole-injecting and -transporting layer, and are injected or transported to the area in which light emitting function is shown (for example, a light emitting layer) from said interface.

On the other hand, electrons are injected into the light emitting layer from the cathode by the action of an electric field, and further transported to recombine with holes in the area of holes, that is, where the light emitting function is shown (in this sense, the above area may be said to be a recombination area). Upon said recombination, the excited states of the molecule, its aggregate or its crystal is formed and transformed to light. The recombination area may be in the interface between the hole-injecting and -transporting layer and the light emitting layer, or in the interface between the light emitting layer and the Cathode, or in the central part of the light emitting layer remote from both interfaces. Said area varies depending on the kind of the compound to be used, its aggregation or its crystal structure.

The styryl compounds to be used for the organic EL device of the present invention represented by the above general formulas (a), (b) and (c) are novel compounds. These styryl compounds can be produced by various processes. Herein taking novel compounds represented by the general formula (d) or (e) as examples, processes for their producing will be described.

The dimerized styryl compound represented by the above general formula (d) can be produced by various processes, but more efficiently it can be produced by the following process.

Process I is a process for producing a dimerized styryl compound represented by the general formula (h):

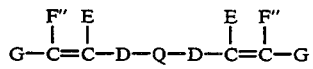

(wherein D, E, F″, G and Q are the same as defined above), which process comprises condensing a phos-phorus compound containing an arylene group or a divalent aromatic heterocyclic ring (hereinafter referred to as just "an arylene group-containing phosphorus compound") represented by the general formula (f):

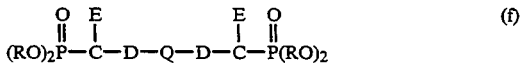

(wherein R is an alkyl group having 1 to 4 carbon atoms or a phenyl group. D, E and Q are the same as defined above), and ketone represented by the general formula (g):

(wherein G is the same as defined above. F″ is the same as the above F, excluding that F is an alkyl group, an aralkyl group or an alkoxyl group).

That is, Process I is a process for producing the desired dimerized styryl compound of the general formula (h) by condensation reaction of an arylene group-containing phosphorus compound represented by the general formula (f) and ketone represented by the general formula (g) as described above.

D, E and Q in the general formula (f) correspond to D, E and Q of the dimerized styryl compound (h) to be produced.

R is an alkyl group having 1 to 4 carbon atoms (e.g., a methyl group, an ethyl group, a propyl group, and a butyl group) or a phenyl group. Said arylene group-containing phosphorus compound can be obtained by reacting, according to a known method, for example the Arbsov reaction, an aromatic bishalomethyl compound represented by the general formula:

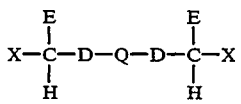

(wherein X is a halogen atom. D, E and Q are as defined above), and trialkyl phosphite or triphenyl phosphite represented by the general formula:

(wherein R is as defined above).

As to the ketone of the general formula (g), F″ and G are selected corresponding to F″ and G of the dimerized styryl compound (h) to be produced. G is the same as in the above general formula (d). F″ is the same as F in the above general formula (d), excluding that F is an alkyl group, an aralkyl group or an alkoxyl group.

The condensation reaction of the general formula (f) and ketone of the general formula (g) can proceed under various conditions. As a reaction solvent to be used in this reaction, hydrocarbon, alcohols and ethers are preferable. Specific examples are methanol, ethanol, isopropanol, butanol, 2-methoxyethanol, 1,2-dimethoxyethane, bis(2-methoxyethyl)ether, dioxane, tetrahydrofuran, toluene, xylene, dimethyl sulfoxide, N,N-dimethylformamide, N-methylpyrrolidone, and 1,3- dimethyl-2-imidazolidinone. Among them preferable are tetrahydrofuran and dimethyl sulfoxide.

As a condensing agent, sodium hydroxide, potassium hydroxide, sodium amide, sodium hydride, n-butyllithium, and alcoholate such as sodium methylate and potassium-t-butoxide can be used at need. Among them preferable are n-butyllithium and potassium-t-butoxide.

The reaction temperature varies depending upon the kind of the reaction material to be used and the other conditions, and cannot be determined unconditionally, but usually it is determined in the wide range of about 1° to 100° C., most preferably 10° to 70° C.

Process II is a process for producing a dimerized styryl compound represented by the above general formula (d), which process comprises condensing a phosphorus compound represented by the general formula (i):

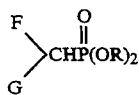 (i)

(wherein F, G and R are as defined above), and diketone represented by the formula (j):

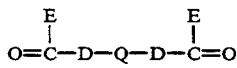 (j)

(wherein D, E and Q are as defined above).

The desired dimerized styryl compound of the general formula (d) can be produced by condensation reaction of a phosphorus compound represented by the general formula (i) and diketone represented by the general formula (j). R in the general formula (i) is an alkyl group having 1 to 4 carbon atoms (e.g., a methyl group, an ethyl group, a propyl group, and a butyl group) or a phenyl group. F and G correspond to F and G of the dimerized styryl compound to be produced. Said phosphorus compound can be obtained by a known method, for example, according to the Arbsov reaction, by reacting a halomethyl compound represented by the general formula:

(wherein X, F and G are as defined above), and trialkyl phosphite or triphenyl phosphite represented by the general formula:

(wherein R is as defined above).

As to the diketone (dialdehyde when E is hydrogen) of general formula (j), E, E and Q are selected corresponding to E, D and Q of the dimerized styryl compound to be produced.

Said diketone (or dialdehyde), especially aromatic diketone (or aromatic dialdehyde) can be produced by a known process, for example, by the following process (1) or (2).

(1) Vilsmeier Reaction

Aromatic dialdehyde represented by the general formula:

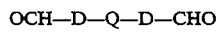

can be prepared by reacting the compound represented by the general formula:

(wherein D and Q are as defined above), and N,N-dimethyl formamide and phosphoryl chloride (POCl₃).

(2) Friedel-Crafts Acylation

Aromatic diketone represented by the general formula (j) can be prepared by reacting the compound represented by the general formula:

(wherein D and Q are as defined above), and acid chloride represented by the general formula:

(wherein E is as defined above) in the presence of Lewis acid.

The condensation reaction of the phosphorus compound of the general formula (i) and diketone (dialdehyde) of the general formula (j) can proceed under various conditions. The reaction solvent and the condensing agent to be used preferably in this reaction are the same as used in the above Process I.

The reaction temperature varies depending upon the kind of the reaction material to be used and the other conditions, and cannot be determined unconditionally, but usually it is selected in the wide range of about 0° to 100° C., most preferably 0° to 70° C.

A dimerized styryl compound of the above general formula (e) can be produced by various processes, but more efficiently by the following Process Process III is a process for producing a dimerized styryl compound represented by the above general formula (e), which process comprises condensing a phosphorus compound containing an arylene group or a divalent aromatic heterocyclic ring (hereinafter referred to as just "an arylene group-containing phosphorus compound") represented by the general formula (k):

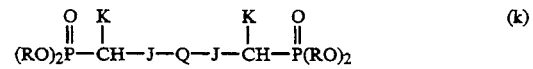 (k)

(wherein J, K, R and Q are as defined above), and aldehyde represented by the general formula (l):

 (l)

(wherein L, M and N are as defined above).

Process III is a process for producing the desired dimerized styryl compound of the general formula (e) by condensation reaction of an arylene group-containing phosphorus compound represented by the general formula (k) and aldehyde represented by the general formula (l) as described above.

J, K and Q in the general formula (k) correspond to J, K and Q of the dimerized styryl compound of the general formula (e) to be produced.

R is an alkyl group having 1 to 4 carbon atoms (e.g., a methyl group, an ethyl group, a propyl group, and a butyl group) or a phenyl group.

The arylene group-containing phosphorus compound of the general formula (k) can be obtained by a known method, for example, according to Arbsov reaction, by reacting aromatic bishalomethyl compound represented by the general formula:

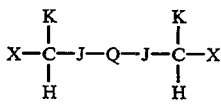

(wherein X, J, K and Q are as defined above), and trialkyl phosphite or triphenyl phosphite represented by the general formula:

(wherein R is an defined above).

As to the aldehyde of the general formula (l), L, N and M are selected corresponding to L, N and M of the dimerized styryl compound of the general formula (e) to be produced.

Said aldehyde can be produced by a known process. For example, by introducing a halogen atom specifically to the compound represented by the general formula:

(wherein L, N and M are as defined above) by substitution reaction of a C—H bond radical by N-haloamide, especially N-chloro- and N-bromo-succinic acid amide, a compound represented by the following general formula:

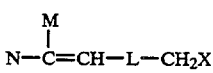

(wherein X, L, N and M are as defined above) is obtained.

Said compound can be converted into aldehyde by using a known reaction, for example, by the following reaction (i) or (ii).

(i) Sommelet Reaction Aldehyde represented by the general formula (l) can be obtained by monoalkylation reaction in which the above halogenated alkyl compound is reacted with hexamethylenetetramine $((CH_2)_6N_4)$, and then hydrolysis thereof.

(ii) Kornblum Oxidation

Aldehyde represented by the general formula (l) can be obtained by reacting the above halogenated alkyl compound with dimethyl sulfoxide.

The condensation reaction of an arylene group-containing phosphorus compound of the general formula (k) and aldehyde of the general formula (l) can proceed under various conditions.

The reaction solvent and the condensation agent to be used preferably in this reaction are the same as used in the above Process I. The reaction temperature varies depending upon the kind of the reaction material to be used and the other conditions, and cannot be determined unconditionally, but usually it is determined in the wide range of about 0° to 100° C., most preferably 0° to 70° C.

Process IV is a process of producing a dimerized styryl compound represented by the above general formula (e), which process comprises condensing a phosphorus compound represented by the general formula (m):

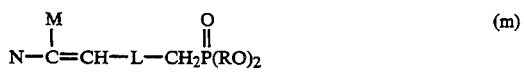

(wherein L, M, N and R are as defined above), and diketone represented by the general formula (n):

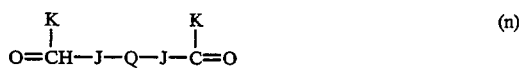

(wherein J, K and Q are as defined above).

Process IV is a process for producing the desired dimerized styryl compound of the general formula (e) by condensing a phosphorus compound represented by the general formula (m) and diketone (dialdehyde) represented by the general formula (n) as described above.

L, M and N in the general formula (m) are selected corresponding to L, M and N of the dimerized styryl compound of the general formula (e) to be produced.

The phosphorus compound represented by the general formula (m) can be obtained by a known process, for example, according to the Arbsov reaction, by reacting an aromatic bishalomethyl compound represented by the general formula:

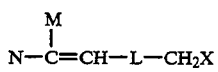

(wherein L, N, M and X are the same as defined above), and trialkyl phosphite or triphenyl phosphite represented by the general formula:

(wherein R is as defined above).

As to the diketone (dialdehyde when K is hydrogen) of the general formula (n), J, K and Q are selected corresponding to J, K and Q of the dimerized styryl compound of the general formula (e) to be produced.

The aromatic diketone (or aromatic dialdehyde) of the general formula (n) can be produced by a known process. Further details of the process are described in the above Process II.

The condensation reaction of a phosphorus compound of the general formula (m) and diketone (dialdehyde) of the general formula (n) can proceed under various conditions. The reaction solvent and the condensing agent to be used preferably in this reaction are the same as used in the above Process I.

The reaction temperature varies depending upon the kind of the reaction material to be used and the other conditions, and cannot be determined unconditionally, but usually it is determined in the wide range of about 0° to 100° C., most preferably 0° to 70° C.

An oligomer compound represented by the general formula (c) can be obtained by the above Processes I to IV. The reaction temperature is most preferably 0° to 80° C.

The present invention is described in greater detail with reference to the examples and the comparative examples, but the present invention is not limited to thereto.

PREPARATION EXAMPLE 1

(1) Preparation of the Compound of Chemical Formula [II]

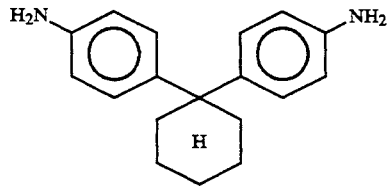

(molecular weight: 262)

325.25 g of aniline hydrochloride (molecular weight: 129.60) was heated while stirring in absence of solvent to 120° C., and 70.27 g (0.717 mol) of cyclohexane (molecular weight: 98) was added dropwise over 30 minutes. Then, the temperature of the bath was raised, heated under reflux (158° C.) for 15 hours, and left cool. Since the reaction solution was coagulated, it was dissolved with about 1 l of warm water (60° to 70° C. ) and about 500 ml of ethyl acetate, and neutralized with 18% aqueous solution of NaOH (600 ml of the solution was used).

After that, the organic layer was taken out, and the aqueous layer was extracted once with 200 ml of ethyl acetate. The organic layer was added to the extract, and the mixture was dehydrated with magnesium sulfate, then concentrated to dryness, and 293 g of a crude product was obtained. The crude product was purified on 5 kg of silica gel column (solvent; $CHCl_3/CH_3OH=100/1$) to obtain 136.22 g of a product of the formula [I] as a mixture containing some spots of slightly higher or lower purity than that of the desired product (yield: 72.52%).

(2) Preparation of the Compound of Chemical Formula [II]

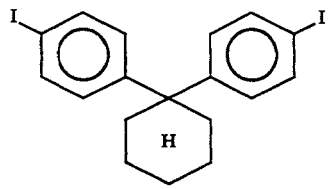

(molecular weight: 487.8)

81.17 g (0,305 mol) of compound [I] was suspended in 343.4 ml of aqueous solution of HCl, 343.3 ml of water was added thereto, then cooled with 3122 g of ice, and 357 ml of aqueous solution of 45.27 g (0.656 mol) of $NANO_2$ (molecular weight: 69) was added dropwise over 15 minutes. Then, the mixture was reacted for 20 minutes at 0° C. or lower, 830 ml of aqueous solution of 209.17 g (1.26 mol) of KI (molecular weight: 166) was added dropwise over 40 minutes, and the resulting mixture was reacted for 2 hours at 0° C. or lower.

Subsequently, 2 l of ethyl acetate was added to separate the organic layer, and the aqueous layer was extracted three times with 500 ml of ethyl acetate. The extract and the organic layer were mixed, washed five times with 1 l of water, dehydrated with anhydrous magnesium sulfate, and concentrated to dryness to obtain 166.6 g of a crude product. The crude product was suspended in 1 l of n-hexane, heat-filtered to remove the insoluble matter. The resulting solution was left to be cooled, and the precipitated crystal was filtrated (Crystal [II]: 56.6 g). The filtrate was concentrated to dryness and mixed with the insoluble matter (containing 110 g of impurity). The mixture was purified with 3 kg of silica gel column (solvent: n-hexane) to obtain 38.08 g of the product represented by the formula [II]. The total amount of the product of the formula [II] was 102.6 g (yield: 68.96%).

(3) Preparation of the Compound of Chemical Formula [III]

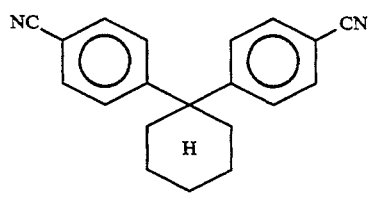

(molecular weight: 286)

113 g (0.232 mol) of the Compound [II] was dissolved in 283 ml of N,N'-dimethylformamide (DMF), 46.6 g (0.521 of CuCN (molecular weight: 89.5) was added thereto and reacted at 175° C. for 4 hours. The reaction product was cooled and put in 1 l of 28% aqueous ammonia to decompose the copper complex, then extracted three times with 1 l of ethyl acetate, dehydrated with anhydrous magnesium sulfate, and concentrated to dryness to obtain 66 g of a crude product of the formula [III] (yield: 99.47%). The crude product was used in the next step without being purified.

(4) Preparation of the Compound of Chemical Formula [IV]

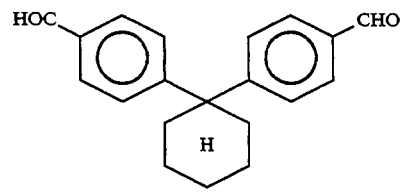

(molecular weight: 292)

66 g (0.23 mol) of the compound [III] was suspended in 627 ml (12.456 mol) of 75% formic acid (molecular weight: 46), 66 g of Raney nickel alloy was added and heated under reflux (108° C.) for two hours, and left to be cool. Then, Raney nickel alloy was filtrated, and 1 l of $CHCl_3$ was added to the reaction solution to separate the organic layer. The aqueous layer was extracted once with 100 ml of $CHCl_3$, and the filtrated Raney nickel alloy was washed well with 100 ml of $CHCl_3$ and mixed with the organic layer. The mixture was washed 9 times with 1 l of water, dehydrated with anhydrous magnesium sulfate, and concentrated to dryness to obtain 50 g of a crude product.

The crude product was purified with 3 kg of silica gel column (solvent: ethyl acetate/n-hexane=1/10), and 38.21 g of the product of the formula [IV] was obtained (yield: 56.89%).

(5) Preparation of the Compound of the Chemical Formula [V]

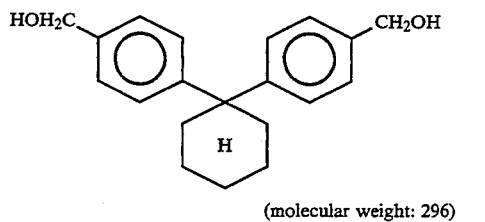

(molecular weight: 296)

22.697 g (0.078 mol) of the Compound [IV] was suspended in 230 mol of tetrahydrofuran (THF), and 7.346 g (0.194 mol) of NaBH$_n$ (molecular weight: 37.83) was added over 20 minutes (in the course of the step, the temperature rose to 30° C., and the mixture was cooled with water). Then, the mixture was reacted at room temperature for one hour and a half.

To the reaction solution, 400 ml of water and 200 ml of ethyl acetate were added, and the organic layer was separated out. The aqueous layer was extracted two times with 100 ml of ethyl acetate and mixed with the organic layer, and the mixture was washed with 200 ml of water four times. The resulting mixture was dehydrated with anhydrous magnesium sulfate, and concentrated to dryness to obtain 22.85 g of the product represented by the formula [V] (yield: 99.39%).

(6) Preparation of the Compound of Chemical Formula [VI]

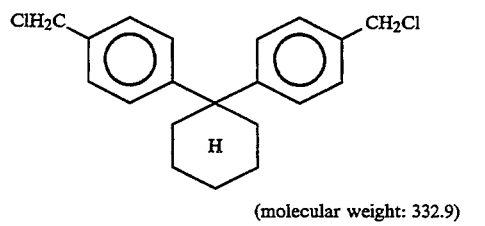

(molecular weight: 332.9)

20.46 g (0.069 mol) of the Compound [V] was suspended in 200 ml of toluene, 1 ml of pyridine was added, 20.559 g (0.173 mol) of SOCl$_2$ (molecular weight: 118.97) was added dropwise thereto over 20 minutes, and the resulting mixture was reacted at room temperature for 2 hours and a half. After the reaction was completed, the reaction mixture was washed by adding 500 ml of water, and the organic layer was separated. The organic layer was washed with 500 ml of 2% NaHCO$_3$, washed three times with 300 ml of water to be adjusted to about pH 7, then dehydrated with anhydrous magnesium sulfate, concentrated to dryness to obtain 23.72 g of a crude product. To the crude product, 47 ml of n-hexane was added. The mixture was stirred well, to precipitate a white crystal. The crystal was filtrated to obtain 16.92 g of the product of the formula [VI] (yield: 73.53%, gas chromatography (GC) purity: 98.352%).

(7) Preparation of the Compound of the Formula [VII]

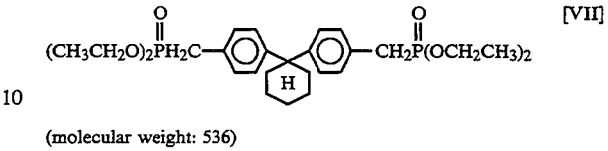

(molecular weight: 536)

To 10.5 g (0.031 mol) of the compound of the formula [VI], 19 g (0.110 mol) of triethyl phosphite was added, and the resulting mixture was stirred for 5 hours while heated at 150° C. in an atmosphere of argon gas. After the mixture was left overnight, triethyl phosphite in excess was distilled away under reduced pressure to obtain 16.2 g of a compound in paste form (formula [VII]) (yield: 98%).

(8) Preparation of the Compound of the Formula [VIII]

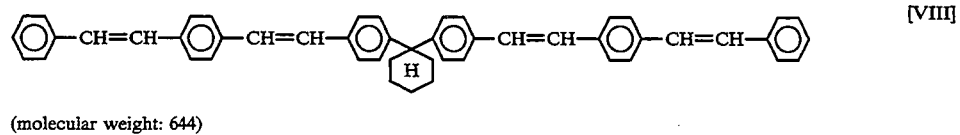

(molecular weight: 644)

4.0 g (0.007 mol) of the compound of the formula [VII] was dissolved in 100 ml of anhydrous tetrahydrofuran in a stream of argon gas, and 1.6 g (0.015 mol) of potassium-t-butoxide was added.

After that, 50 ml of a tetrahydrofuran solution of 3.1 g (0,015 mol) of 4-stilbene carboxy-aldehyde was added dropwise over 30 minutes. The mixture was stirred for 7 hours while heated at 40° C., and 1.75 g of a pale yellow powder precipitated was taken by filtration.

For transfication, the powder was recrystallized with benzene containing a slight amount of iodine, and 1.56 g of a pale yellow powder having a melting point of 283.0° to 285.0° C. was obtained (yield: 33%).

$^1$H-NMR of the product was as follows.
$^1$H-NMR (CDCl$_3$, TMS)
δ=6.8 to 7.3 ppm (m; 34H, aromatic ring-H and vinyl-CH=CH—)
δ=1.4 to 2.4 ppm (b; 10H, cyclohexyl-H)
IR spectrum (KBr pellet method)
980 cm−1 ($\sigma_{C-H}$ trans)

The elementary analysis for C$_{50}$H$_{44}$ was as follows. The values in parentheses are theoretical.

C 93.40% (93.12%), H 6.62% (6.88%), N 0.00% (0%).

The above analytical values confirmed that the product obtained was the compound of the formula [VIII].

PREPARATION EXAMPLE 2

(1) 51 g (0.168 mol) of O,O-diethyldiphenylmethylphosphonate (molecular weight: 302.3) was dissolved in 200 ml of anhydrous tetrahydrofuran in a stream of argon gas. Immediately on adding 19.0 g (0.169 mol) of potassium-t-butoxide, the solution turned to yellow. Thereafter, 21.0 g (0.174 mol) of p-trialdehyde was added dropwise over one hour at room temperature. The resulting mixture was stirred while heated at 50° C. for 5 hours, and then 100 ml of methanol and 100 ml of water were added to separate the organic layer. The aqueous layer was extracted once with 100 ml of $CH_2Cl_2$, and mixed with the organic layer, and concentrated to dryness. The resulting matter was purified on silica gel column (solvent: $CH_2Cl_2$), to obtain 34.4 g of yellow powder which was the compound of the formula [I-2] (Yield 74%).

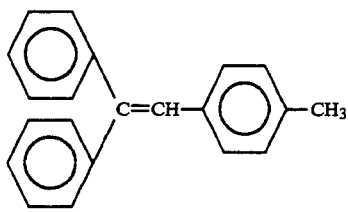

[I-2]

(molecular weight: 272)

(2) 25.0 g (0.0917 mol) of the compound of the formula [I-2], 16.0 g (0.09 mol) of N-bromosuccinic acid imide and 1.6 g (0.006 mol) of peroxide benzoyl were suspended in 200 ml of carbon teterachloride, and heated while strongly stirring. The resulting solution reacted in bubbling at an ambient temperature of 100° C., being stirred in reflux for 6 hours.

The resulting white precipitate was collected by filtration, washed with methanol to obtain the compound of the formula [II-2] as 21.6 g of a pale yellowish powder (yield: 67%).

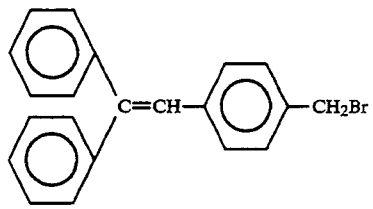

[II-2]

(molecular weight: 349)

(3) 28.5 g (0.0815 mol) of the compound of the formula [II-2] and 35.0 g (0.211 mol) of tryethyl phosphite were stirred for 5 hours while heated at an ambient temperature of 120° C. in an atmosphere of argon gas.

The resulting mixture was left overnight, and then tryethyl phosphite in excess was vacuum-distilled away to obtain a compound of the formula [III-2] as 32.0 g of pasty matter (yield: 97%).

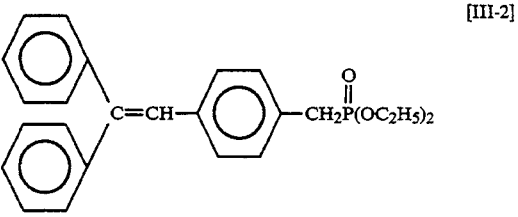

[III-2]

(molecular weight: 406)

(4) 2.8 g (0.0068 mol) of the compound of the formula [III-2] was dissolved, in a stream of argon gas, in 100 ml of anhydrous tetrahydrofuran, and 1.0 g (0.0089 mol) of potassium-t-butoxide was added. Thereafter, 100 ml of tetrahydrofuran solution of 1.0 g (0.0034 mol) of the compound of the formula [IV-1] obtained in Example 1 (4) was added dropwise to the solution over 30 minutes. After the resulting solution was stirred for 3 hours at room temperature, 100 ml of methanol and 50 ml of water were added, and 1.5 g of a yellow powder precipitated was collected by filtration. The powder was recrystallized with benzene containing a light amount of iodine for the purpose of transfication, and purified on silica gel column (solvent: $CH_2Cl_2$) to obtain 1.2 g of a yellow powder (yield: 46%).

$^1$H-NMR of the product was as follows.
$^1$H-NMR(CDCl$_3$, TMS)

$\delta = 6.8$ to 7.3 ppm (m; 42H, aromatic ring-H and methylidene $-CH=C=$)

$\epsilon = 1.4$ to 2.4 ppm (b ;10H, cyclohexyl-H)

From a direct-leading mass spectrum (MS), the molecular ion peak (m/Z=796) of the objective product only was detected.

The result of the elementary analysis provided the composition formula as $C_{62}H_{52}$ is as follows. The values in parentheses are theoretical.

C 93.06% (93.43%), H 6.63% (6.57%), N 0.00% (0%).

IR spectrum (KBr pellet method)
980 cm$^{-1}\sigma$ (CH) trans)

Above results confirmed that the yellow powder produced above was a dimer represented by the formula:

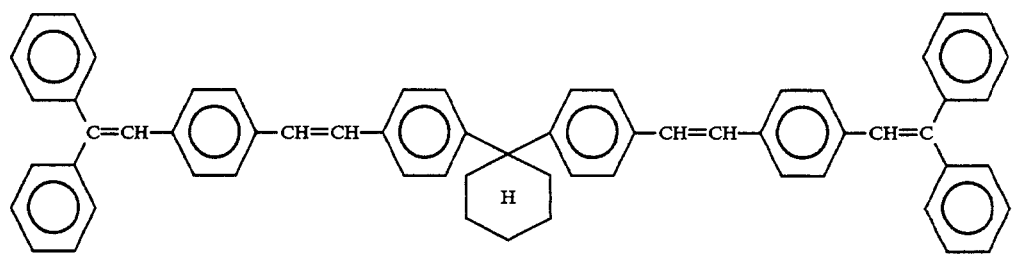

PREPARATION EXAMPLE 3

(1) Preparation of Grignard Reagent

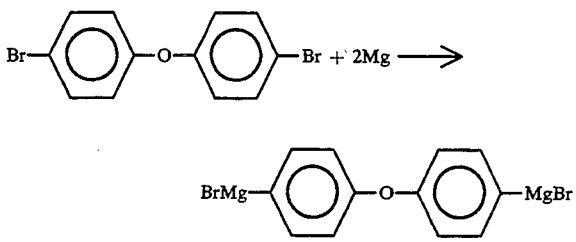

To 39.3 g (1.62 gram atom) of magnesium in form of turnins and 600 ml of dry-distilled THF stirred while heated to 50° C., a small amount of iodine was added to activate magnesium. To the resulting mixture, a solution obtained by dissolving 241.5 g (0.738 mol) of 4,4'-dibromodiphenylether in 1 l of dry-distilled THF was added dropwise. The dropping was completed in about an hour. As said solution of 4,4'-dibromodiphenylether solution was added dropwise, the reaction solution turned into green, and ten minutes after dropping, the dark green turned into a green mixed with pale brown turbidity. Since the reaction heat raises the temperature, the temperature of the water bath was controlled to adjust the reaction temperature to 50° to 55° C. In the course of the reaction where excess Mg (3.4 g) still remained (about 1.5 hours after the dropping finished) the green color was completely gone. By gas chromatography 4,4'-dibromodiphenylether was not detected. After the completion of the dropping, the solution was stirred for 3 hours at 52° to 55° C., then started to be cooled, and after 30 minutes when the solution was cooled to 17° C., 800 ml of THF was added. All these reactions were conducted in an atmosphere of argon.

(2) Formylation Reaction

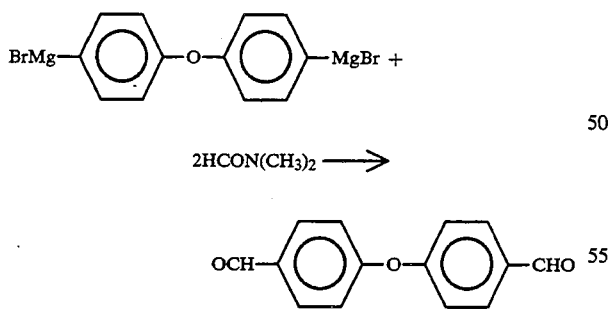

While all the Grignard reagent solution was somewhat cooled so that the temperature of the reaction solution was kept to be 20° C., a solution obtained by dissolving 132 g (1.81 mol) of dried DMF in 660 ml of THF was added dropwise over 45 minutes. After stirred at room temperature (5° to 15° C.) overnight, the solution was poured into 2 kg of ice water, and 480 g of ammonium chloride was added. After stirred for some while, the solution was extracted 5 times with 1 l of ethyl acetate, and the ethyl acetate layer was filtrated out and evaporated to obtain 165 g of a brown viscous liquid.

As the end point of the reaction, the time when dialdehyde stopped increasing and the pattern of the thin layer chlomatography (TLC) no more changed according to the determination by a gas chromatography was regarded. The product was then purified by column chromatography (column: silica gel, carrier: chloroform) to obtain 23 g of a white solid.

NMR analysis (solvent: $CDCl_3$, internal standard: tetramethylsilane (TMS))

$\delta = 9.93$ ppm (s, 2H) 7.9 ppm (d, 4H) 7.2 ppm (d, 4H)

IR analysis: 1695 $cm^{-1}$ (CHO), 1220 $cm^{-1}$ (ether), 862 $cm^{-1}$ (1,4-substituent)

Melting Point: 57° to 58° C.

By these analytical values, it was confirmed that the above product was 4,4'-diformylphenylether represented by the formula:

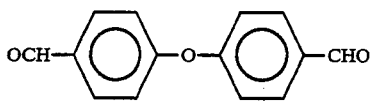

(3) 3.0 g (0.0073 g) of the compound of the formula [III-2] obtained in Preparation 2 (3) was dissolved, in a stream of argon, in 100 ml of anhydrous tetrahydrofuran, and 0.8 g (0.0073 mol) of potassium-t-butoxide was added. Subsequently, 100 ml of a tetrahydrofuran solution of 0.8 g (0.0037 mol) of the compound of the formula [I-2] obtained in Example 2 (1) was added dropwise at room temperature over 30 minutes. After the resulting solution was stirred for 6 hours while heated at 50° C., 100 ml of methanol was added, and a yellow powder was precipitated. The precipitate was filtrated to obtain 0.5 g of a yellow powder. In order to transfy all the resulting powder, it is recrystallized with benzene comprising a slight amount of iodine, and further purified on a silica gel column (solvent: $CH_2Cl_2$, 45 mm in inner diameter × 150 mm in length) to obtain 0.4 g of a pale yellow powder (yield: 15%).

The melting point of the resulting pale yellow powder was 200° to 201° C. $^1$H-NMR of the product was as follows.

$^1$H-NMR ($CDCl_3$, TMS)

$\delta = 8$ to 7.3 ppm (m; 42H, aromatic compound-H and methylidene —CH=C=) and vinyl —CH=CH—)

By MS, the molecular ion peak of the objective product (m/Z=730) only was detected.

The result of an elementary analysis providing the composition formula as $C_{56}H_{42}O$ is as follows. The values in the parentheses are theoretical.

C: 92.27 % (92.02% ), H: 6.01% (5.79%), N: 0.00% (0%)

IR spectrum (KBr pellet method)

980 $cm^{-1}$ ($\sigma_{(C-H)}$ trans)

Above results confirmed that the pale yellow powder as the above product was a compound represented by the formula:

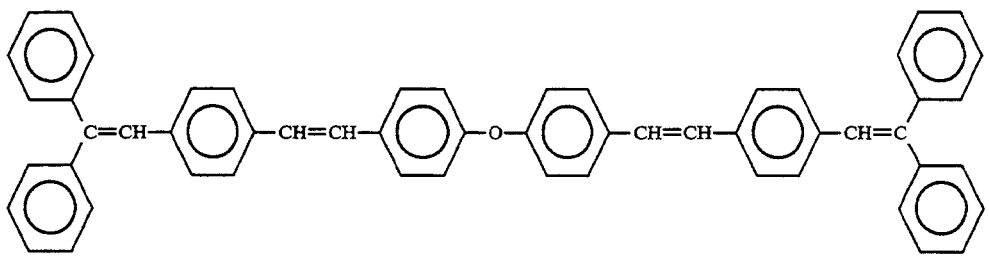

PREPARATION EXAMPLE 4

Preparation of:

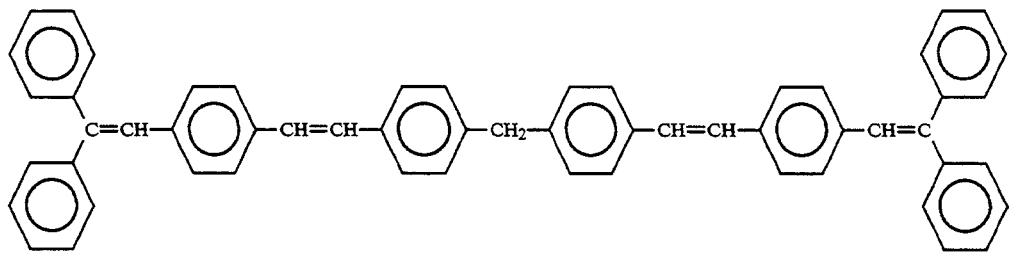

(1) Preparation of:

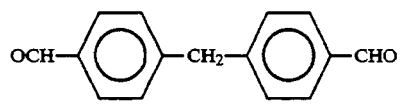

(molecular weight: 224; 4,4'-diformylphenylmethane)

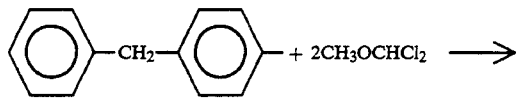

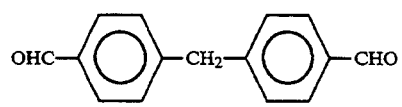

70 g (0.417 mol) of diphenylmethane was dissolved in 1 l of dried methylene chloride, cooled to 0° C., then 466 g (2.45 mol) of titanium tetrachloride was added while the solution was stirred, and 2255 g (2.22 mol) of dichloromethyl methylether was added dropwise to it. The dropping was completed in one hour while the reaction solution was kept at 0° C. The solution was stirred for further one hour, then returned to room temperature in two hours, and stirred overnight.

As TLC pattern was not changed even with further stirring, a post-treatment was conducted. The reaction solution was poured into a solution obtained by adding 70 ml of conc hydrochloric acid to 2.4 kg of ice water, and the mixture was stirred for 30 minutes, and extracted with of isopropyl ether and 1.2 l of ethyl acetate. Subsequently the oil layer was put together with the extract, and the mixture was washed with water, dried with anhydrous sodium sulfate when pH of the washing water became 5 to 6, and evaporated under reduced pressure to obtain 101 g of a pale yellow solid. Said crude product was purified by a column chromatography (column: silica gel, carrier: ethyl acetate/hexane) to obtain 22 g of a white crystal.

$^1$H-NMR (CDCl$_3$, TMS) of the product
$\delta$=9.9 ppm (s, 2H), 7.75 ppm (s, 4H) 7.28 ppm (d, 4H) 4.08 ppm (s, 2H)

IR analysis: 1685 cm$^{-1}$ (—CHO), 1600 cm$^{-1}$ (benzene), 850 cm$^{-1}$ (1,4-substituent)

(2) Preparation of:

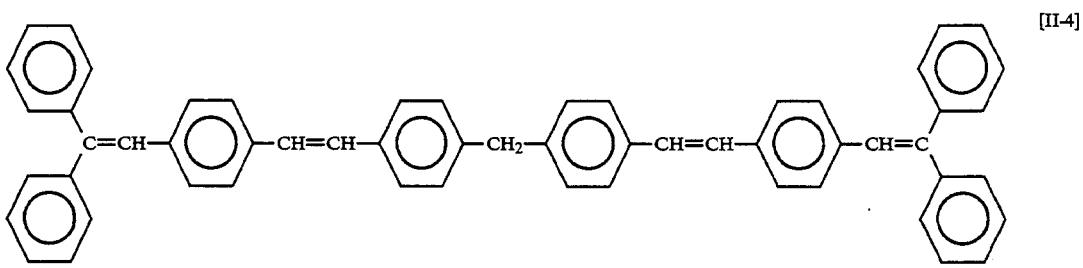

(molecular weight: 728)

The procedure of Preparation Example 3 (4) was repeated except that 4,4'-diformylphenylmethane, that is, the compound of the formula [I-4] obtained in (1) above was used in place of 4,4'-diformylphenylether, and the desired compound was obtained. The analytical data are as follows.

Melting Point: 210° to 211.5° C.

¹H-NMR (CDCl₃, TMS)

δ=6.8 to 7.4 ppm (m; 42H, aromatic ring-H and methylidene —CH=C=) and vinyl —CH=CH—)

δ=3.9 ppm (s; 2H, central methylene —CH₂—)

By MS, the molecular ion peak of the objective product (m/Z=724) was detected. The result of an elementary analysis providing the composition formula as C₅₇H₄₄ is as follows. The values in the parentheses are theoretical.

C: 93.84% (93.92%), H: 5.92% (6.08%), N: 0.00% (0%).

IR spectrum (KBr pellet method)

980 cm⁻¹ ($\sigma_{(C-H)}$ trans)

From the above results, it was confirmed that the pale yellow powder resulted above was a compound represented by the formula:

PREPARATION EXAMPLE 5

Preparation of

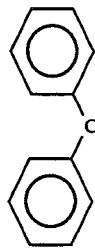

(1) Preparation of

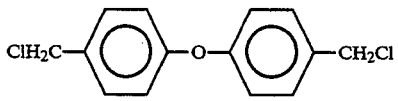  [I-5]

The above compound was prepared according to the preparing way as follows.

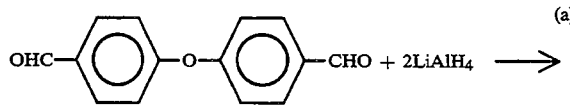 (a)

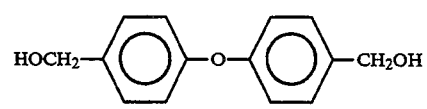 (b)

-continued

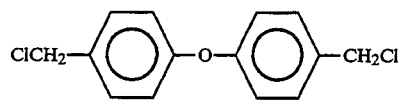

(a) Preparation of 4,4'-di(hydroxymethyl)diphenylether

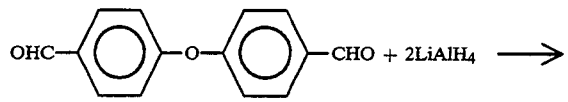

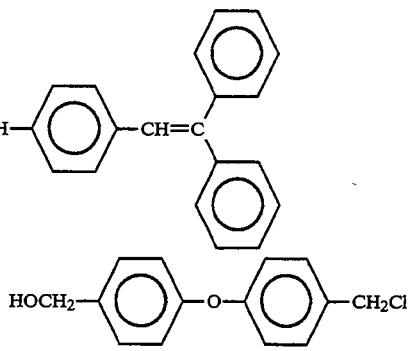

A solution obtained by dissolving 30 g (0.133 mol) of 4,4'-diformylphenylether in 150 ml of THF dried by a molecular sieve was dropped at 0° C. into a slurry consisting of 12 g (0.316 mol) of LiAlH₄ and 850 ml of dried THF. It took 40 minutes to drop the solution, and a grey viscous slurry resulted. A TLC analysis showed that no dialdehyde remained more. Further, the slurry was stirred at 0° C. for two hours, and analyzed by TLC, which resulted one spot. After 10 ml of ethyl acetate was added dropwise at 5° C. or lower, 250 ml of water was added dropwise at 15° C. or lower. Subsequently, 240 ml of (1: 1) hydrochloric acid was added, and the resulting mixture was extracted three times with 250 ml of ethyl acetate, and then the oily layer was added together. The resulting mixture was washed with water, dried with anhydrous sodium sulfate, and evaporated to obtain 28.2 g of a white solid. The result of analyzing the solid is as follows.

¹H-NMR (CDCl₃, internal standard: TMS)

δ=7.3 ppm (d, 4H) 6.9 ppm (d, 4H) 4.57 ppm (s, 3.1 ppm (s, 2H)

The above results confirmed that the white solid was 4,4'-di(hydroxymethyl)diphenylether.

The while solid was used as it was as the starting material of next reaction.

(b) Preparation of 4,4'-di(chloromethyl)diphenylether

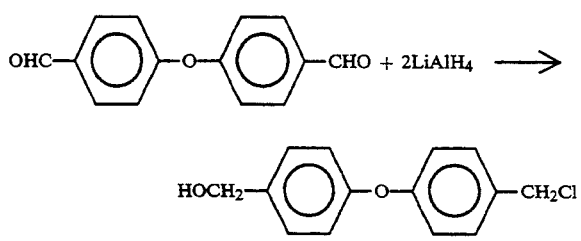

To 28 g (0.122 mol) of 4,4'-di(hydroxymethyl)diphenylether obtained in (a) above, 56 ml of conc hydrochloric acid was added, and stirred on an oil bath at 110° C. for 2 hours and a half. After it was confirmed by TLC analysis that the material was hardly remained, the aqueous layer was removed by filtration, and the resulting cake was washed with water till it became neutral. The cake was then air-dried at 40° C. to obtain 30.5 g of the desired crude crystal. The crude crystal was purified on a column chromatography (column: silica gel, carrier: ethyl acetate/hexane) to obtain 24.5 g of the desired product.

Melting Point: 52° to 53° C.

$^1$H-NMR (CDCl$_3$, standard: TMS)

δ=7.27 ppm (d, 4H), 6.9 ppm 4.5 ppm (s,

IR: 1590 cm$^{-1}$ (benzene ring), 1249 cm$^{-1}$ (phenylether), 870 cm$^{-1}$ (1,4-substituent), 660 cm$^{-1}$ (C—Cl)

(2) Preparation of

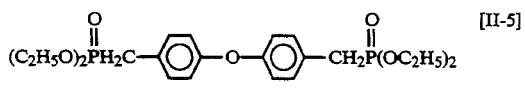

(molecular weight: 486)

To 10 g (0.037 mol) of the compound of the formula [I-5], 16 g (0.09 mol) of triethyl phosphite was added, and the mixture was stirred for 2 hours, in an atmosphere of argon gas, while heated at 150° C. The mixture was left overnight, and excess triethyl phosphite was vacuum-distilled away to obtain 17.8 g of a compound of the formula [II-5] in paste form (yield: 99%).

(3) Preparation of

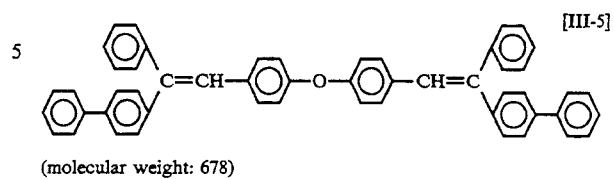

(molecular weight: 678)

4.2 g (0.0086 mol) of the compound of the formula [II-5] was, in an atmosphere of argon gas, dissolved in 200 ml of dimethylsulfoxide, and 2.0 (0.0173 mol) of potassium-t-butoxide was added thereto. Then, 4.5 g (0.0173 mol) of N-benzoylbiphenyl was added, and stirred for 6 hours while heated at 50° C. Dimethylsulfoxide in the reaction solution was vacuum-distilled away, and 200 ml of methanol was added to the remainder, and cooled to −20° C. The while powder precipitated was purified on silica gel column (solvent: CH$_2$Cl$_2$, 40 mm in diameter×250 mm in length) to obtain 1.43 g of a white powder (yield: 25%).

$^1$H-NMR of the product was as follows.

$^1$H-NMR(CDCl$_3$, TMS)

δ=6.5 to 7.6 ppm (m; 38H, aromatic ring-H and methylidine —CH=C=)

By MS, the molecular ion peak (m/Z=678) only was detected.

The result of elementary analysis providing the composition formula as C$_{52}$H$_{38}$O is as follows. Values in the parentheses are theoretical.

C: 92.09% (92.00%), H: 5.72% (5.64%), N: 0.00% (0%).

The above results confirmed that the above-mentioned product was a compound represented by the formula:

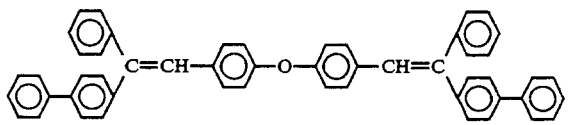

PREPARATION EXAMPLE 6

Preparation of

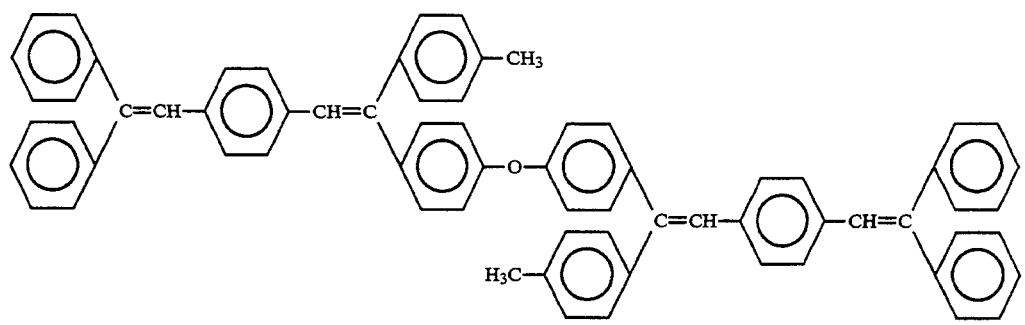

(1) Preparation of

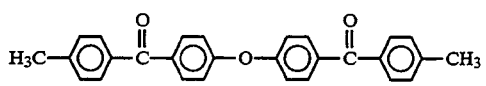

(molecular weight: 406)

In a 200 ml three-neck flask, 20 g (0.15 mol) of aluminum chloride and 100 ml of 1,2-dichloroethane were placed, and while the mixture was cooled to 0° C., 15.0 g (0.009 mol) of p-methylbenzoylchloride was added dropwise in a stream of argon over two hours. Subsequently, a solution of 8.2 g (0.048 mol) of diphenylether and 10 ml of 1,2-dichloroethane was added dropwise at 0° C. over two hours. After the dropping was completed, the resulting solution was stirred for two hours. Then the solution was left overnight, and poured onto 100 g of ice, and the aqueous layer was extracted with 100 ml of methylene chloride, and the organic layer was washed two times with 100 ml of a 5% aqueous solution of sodium hydroxide and three times with 100 ml of water, and the organic layer was dried with potassium carbonate. When the solvent was distilled away, a white powder was obtained. The powder was recrystallized with a mixed solvent (methylene: ethanol=9:1) to obtain 10 g of the desired white scale crystal (yield: 51%).

Melting Point: 202.0° to 203.0° C.

$^1$H-NMR (CDCl$_3$, TMS),

δ=7.0 to 7.9 ppm (m; 16H, aromatic ring-H)

δ=2.4 ppm (s; 6H, methyl group-CH$_3$)

(2) Preparation of

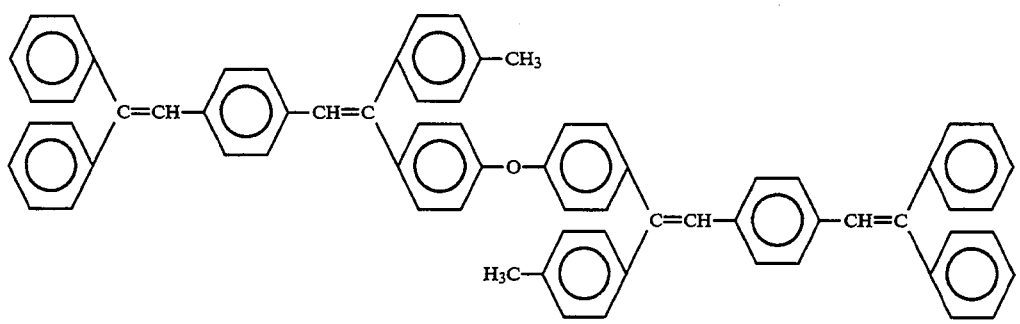

(molecular weight: 910)

3.8 g (0.0093 mol) of the compound of the formula [III-2] obtained in Preparation Example 2 (3) was, in a stream of argon gas, suspended in 150 ml of dimethylsulfoxide, and 2.0 g (0.0049 mol) of the compound of the formula [I-6] (diketone) obtained in (1) above and 1.2 g (0.010 mol) of potassium-t-butoxide were added thereto. The solution was a red brown suspension, and was stirred at room temperature for 6 hours. The solution was left overnight, and the solvent was distilled away. Then 700 ml of methanol was put into the reaction mixture, and the precipitated pale yellow powder was taken by filtration. The powder was purified on a silica gel column (solvent: CH$_2$Cl$_2$, 40 mm in diameter×230 mm in length), to obtain 0.9 g (yield: 20%) of amorphous crystal. Determination by a differential scanning calorimetry (DSC) showed that Tg of the crystal was 91.7° C.

$^1$H-NMR of the product was as follows.

$^1$H-NMR (CDCl$_3$, TMS )

δ=6.6 to 7.4 ppm (m; 18H, aromatic ring-H)

δ=2.3 ppm (s, 6H, methyl group-CH$_3$)

By MS, the molecular ion peak of the desired product (m/Z=910) only was detected.

The result of an elementary analysis providing the composition formula as C$_{70}$H$_{54}$O was as follows. The values in the parentheses are theoretical.

C: 92.49% (92.27%), H: 5.80% (5.97%), O: 0.00% (0%)

The above fact confirmed that the above-mentioned product, was a compound represented by the formula:

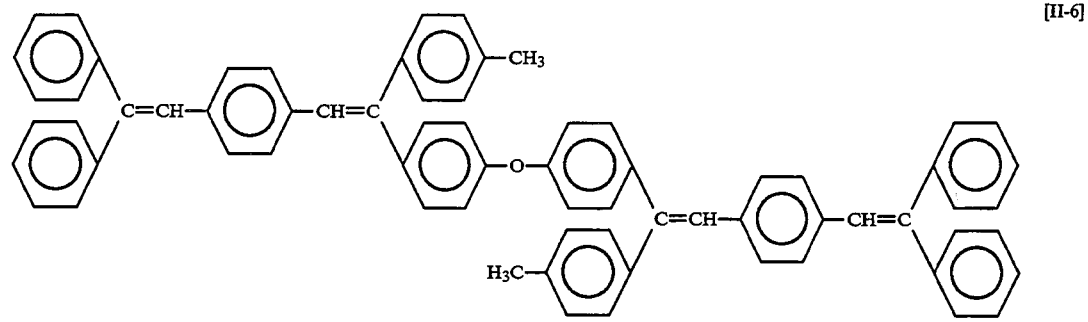

PREPARATION EXAMPLE 7

The same procedure as in Preparation Example 5 (3) was repeated except that 3-(N-ethyl)-carbazolcarboxyaldehyde was used in place of 4-benzoylbiphenyl to obtain Compound 7 shown in Table 1. The physical properties of the compound are shown in Table 1.

PREPARATION 8

Preparation of:

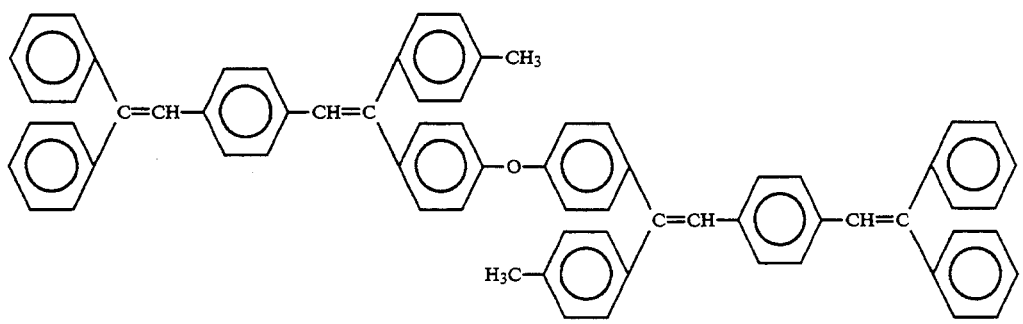

(molecular weight: 1062)(C$_{82}$H$_{62}$O)

(1)

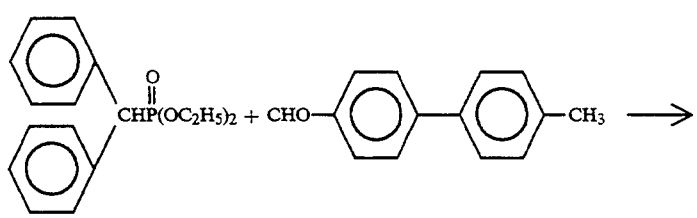

11.2 g (0.037 mol) of O,O-diethyldiphenylmethylphosphonate and 7.2 g (0.036 mol) of 4-methyl-4'-formylbiphenyl were, in a stream of argon gas, dissolved in 200 ml of anhydrous dimethylsulfoxide, and 4.1 g (0.036 mol) of potassium-t-butoxide was added thereto.

Then, the solution was stirred at room temperature for six hours, and 200 ml of methanol was added to obtain 8.0 g of a white powder (yield: 64%) as a precipitate. The melting point of the compound was 128.0° to 129.0° C.

$^1$H-NMR of the product was as follows.
$^1$H-NMR(CDCl$_3$, TMS)

δ=6.8 to 7.4 ppm (m; 19H, aromatic ring-H and methylidene —CH=C=)
δ=2.3 ppm (s; 3H, methyl group —CH$_3$)

(2)

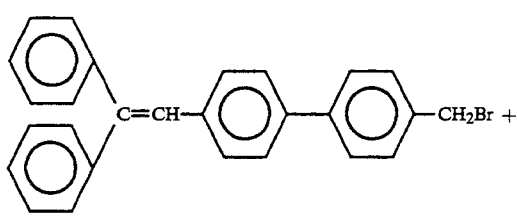

N-bromosuccinimide ⟶

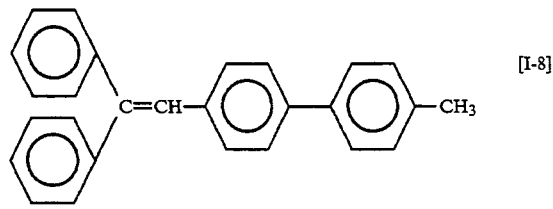

[I-8]

(molecular weight: 346)

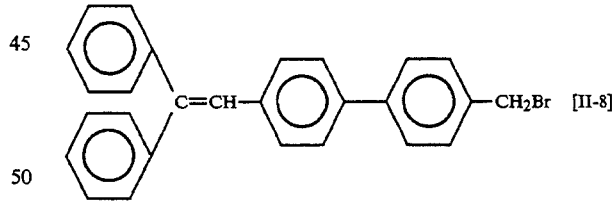

[II-8]

(molecular weight: 425)

6.5 g (0.018 mol) of the compound [I-8], 3.5 g (0.019 mol) of N-bromosuccinimide and 0.7 g of benzoyl peroxide were suspended in 150 ml of carbon tetrachloride, and stirred vigorously at an ambient temperature of 100° C. The mixture was stirred in reflux for 4 hours, the solvent was distilled away to obtain 10 g of a pale yellow powder. The powder was purified on silica gel column (solvent: methylene chloride) to obtain 5.3 g of a white powder (yield: 70%). The melting point of the compound was 127.0° to 128.0° C.

$^1$H-NMR of the product was as follows.
$^1$H-NMR(CDCl$_3$, TMS)

δ=7.6 to 6.9 ppm (m; 19H, aromatic ring-H and methylidine —CH=C=)
δ=4.5 ppm (s; 2H, bromomethyl-CH$_2$Br)

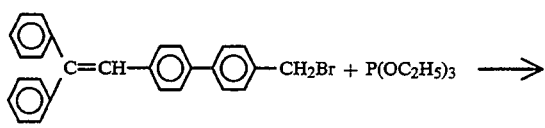

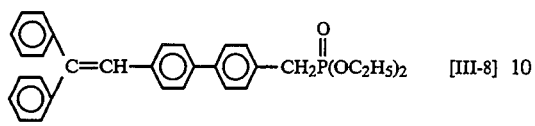

(molecular weight: 425)

To 5.3 g (0.0125 mol) of the compound [II-8], 13.0 g (0.079 mol) of triethyl phosphite was added, and stirred to obtain 6.0 g (quantitative) of a pale yellow powder. The melting point of the compound was 62° to 64° C.
$^1$H-NMR of the compound was as follows.
$^1$H-NMR(CDCl$_3$, TMS)
δ=7.0 to 7.4 ppm (m; 18H, aromatic ring-H)
δ=6.9 ppm (s; 1H, methylidene —CH=C=)
δ=4.0 ppm (q; 4H, ethoxy group —CH$_2$—)
δ=3.1 ppm (d; 2H, —CH$_2$—P, J=16Hz )
δ=1.3 ppm (t; 6H, ethoxy group —CH$_3$)

The same procedure of Preparation Example 6 (2) for preparing [II-6] was repeated except that the compound [III-8] prepared in Preparation Example 8 (3) was used in place of diketone compound [I-6] obtained in Preparation Example 6 (1), and Compound 8 shown in Table 1 was prepared. The physical properties of the resulting compound are shown in Table 1.

TABLE 1

| Com-pound | Composition Formula (Molecular Weight) | Melting Point (°C.) | $^1$H-NMR (CDCl$_3$, TMS) | State | Mass Spectrum | Result of Elementary Analysis (%) ( ): Values in parentheses are theoretical |
|---|---|---|---|---|---|---|
| Preparation Example 7 | (22) C$_{44}$H$_{36}$N$_2$O (608) | 237.0~238.0 | δ = 8.1~6.9 ppm (m; 28H, Aromatic Ring and Carbazol Ring —H) δ = 4.25 ppm (q; 4H, Ethyl group —CH$_2$—) δ = 1.4 ppm (t; 6H, Ethyl group —CH$_3$) | White powder | m/Z = 608 | C: 86.53 (86.81) H: 5.72 (5.96) N:4.32 (4.60) |
| Preparation Example 8 | (69) C$_{82}$H$_{62}$O (1062) | 203.0~204.0 | δ = 6.8~7.9 ppm (m; 56H, Aromatic Ring and H of —CH=C) δ = 2.5 ppm (s; 6H, Methyl group —CH$_3$) | Yellowish green powder | m/Z = 1062 | C: 92.31 (92.31) H: 5.41 (5.41) N: 0.00 (0.00) | for six hours while heated at 110° C., in an atmosphere of argon gas. The solution was left overnight, and excess triethyl phosphite was vacuum distilled away to obtain a compound in yellow paste form. The compound was purified on a silica gel column (solvent: initially methylene chloride, and subsequently a mixture of methylene and acetone with a ratio by volume of 1:1)

PREPARATION EXAMPLE 9

Preparation of

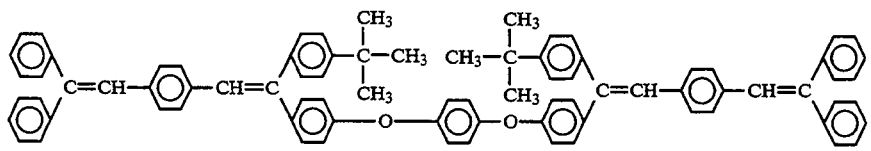

(1) Preparation of Diketone as the Starting Material

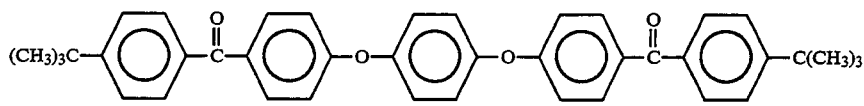

The diketone compound as the starting material was prepared according to the reaction formulae as follows.

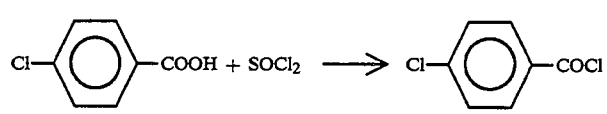

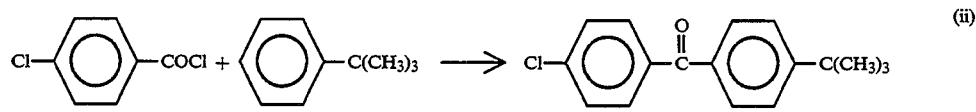

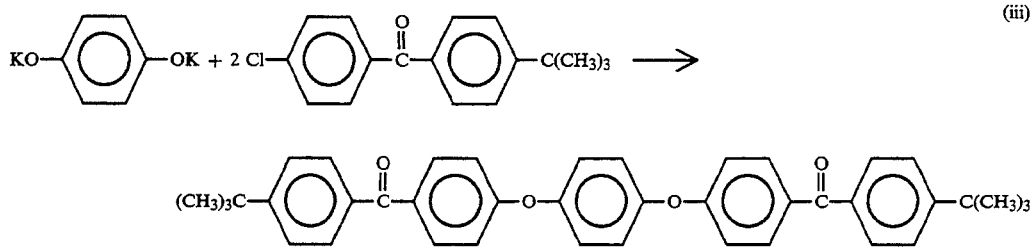

(i) Preparation of p-chlorobenzoic acid chloride

A mixture of 76 g (0.486 mol) of p-chlorobenzoic acid 0.3 ml of pyridine and 150 ml of thionyl chloride was heated gradually while stirring, and reacted until no carboxylic acid remained at 45° to 60° C. (confirmed by nuclear magnetic resonance (NMR) analysis). When carboxylic acid was not present more, vacuum distillation was conducted to obtain 86 g of orange yellow liquid. A NMR analysis confirmed that the orange yellow liquid was p-chlorobenzoic acid chloride.

(ii) Preparation of p-t-butylbenzoyl-4-chlorobenzene

To 64 g (0.48 mol) of anhydrous aluminum chloride and 200 ml of methylene chloride which were stirred at room temperature, 84 g (0.48 mol) of chlorobenzoyl chloride was added dropwise. To the resulting brown solution, 76 g (0.567 mol) of t-butylbenzene was added dropwise at 35° to 40° C. As no acid chloride remained 30 minutes after the completion of dropping, the reaction solution was poured into ice water, and extracted with isopropylether (IPE). Then the oil layer was washed with dilute hydrochloric acid, washed with sodium hydrogencarbonate, washed with water, then dried with anhydrous sodium sulfate, and evaporated to obtain 145 g of a viscous liquid. After left at room temperature, the liquid was crystallized. The solution was filtrated with a silica gel column using IPE/n-hexane =1/20 as a carrier to obtain 85 g of a slightly yellow solid. The slightly yellow solid was confirmed to be p-t-butylbenzoyl-4-chlorobenzene by NMR analysis.

(iii) Preparation of 1,4-bis(4-t-butylbenzoylphenoxy)benzene

From a mixture solution of 15 g (0.136 mol) of hydroquinone, 15.3 g (0.237 mol) of potassium hydroxide and 70 ml of water, water was removed by vacuum distillation, and subsequently, the residue was dried for 15 hours by a vacuum drier at 120° C. Then, 80 g (0.294 mol) of p-t-butylbenzoyl-4-chlorobenzene, PEG-6000 (1.3 g) and 150 ml of dimethylsulfoxide were stirred for 41 hours while heated at 150° C. The reaction solution was cooled, and 700 ml of water was added and filtrated to make a wet cake, and 2 l of ethyl acetate was added and filtrated. The filtrate was evaporated, and a solution of ethyl acetate/hexane=1/7 was added to make a wet cake and filtrated. Further, 53.4 g of a wet cake obtained by combining two cakes was purified on a 5 kg silica gel column with THF/n-hexane=1/7 as a carrier. As the resulting solid was colored, it was decolored and purified on 3.5 kg of silica gel column with THF/n-hexane=1/7 as the carrier. The pale yellow solid obtained was recrystallized with hexane to obtain 22 g of white crystal. A high performance liquid chromatography (HPLC) showed that the purity of the crystal was 99.6%, and the melting point was 192 to 193° C., and NMR analysis confirmed that the crystal was 1,4-bis(4-t-butylbenzoylphenoxy)benzene.

(2) Preparation of the Desired Product 2.85 g (0.007 mol) of the compound obtained in Preparation Example 2 (3) was added to 50 ml of dimethylsulfoxide in a stream of argon gas, and suspended, then 1.86 g (0.0032 mol) of the diketone compound obtained in Preparation Example 9 and 0.82 g (0.007 mol) of potassium-t-butoxide were added to the suspension. The resulting red brown suspension was stirred for 5 hours and left overnight, and the solution was distilled away. To the reaction mixture, 100 ml of methanol was put in, and the precipitated pale yellow powder was taken by filtration. The powder was purified on a silica gel column (solvent :CHCl$_3$/n-hexane=2/3 (ratio by volume), column: 120 g) to obtain 0.82 g (yield: 24%) of pale yellow powder. The melting point of the pale yellow powder obtained was 246° to 247° C.

$^1$H-NMR of the compound was as follows.

$^1$H-NMR (CDCl$_3$, TMS)

δ=6.7 to 7.4 ppm (m; 52H, aromatic ring-H, vinyl group —CH=C)

δ=1.5 ppm (s; 18H, t-butyl group —CH$_3$)

By MS, the molecular ion peak (m/Z =1086) of the objective product only was detected.

The result of an elementary analysis with the composition formula as C$_{82}$H$_{70}$O$_2$ was as follows. Values in the parentheses are theoretical.

C: 90.71% (90.57%), H: 6.32% (6.49%), O: 0.00% (0%).

The above result confirmed that the above product was the desired product.

PREPARATION EXAMPLE 10

The same procedure as in Preparation Example 9 was taken except that bisphenol A was used in place of hydroquinone, and Compound 10 shown in Table 2 was obtained. Table 2 shows the physical properties of said compound.

PREPARATION EXAMPLE 11

The same procedure as in Preparation Example 9 was taken except that bis(4-hydroxyphenyl)sulfone was used in place of hydroquinone and that Compound A:

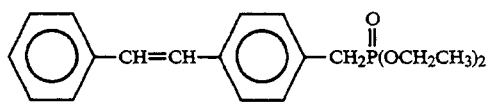

was used in place of the compound obtained in Preparation Example 2 (3), and Compound 11 shown in Table 2 was obtained. The physical properties of said compound are shown in Table 2.

PREPARATION EXAMPLE 12

The same procedure as in Preparation Example 9 was taken except that 2,2-bis(4-hydroxyphenyl)fluoropropane was used in place of hydroquinone and that the above-mentioned Compound A was used in place of the compound obtained in Preparation Example 2 (3), and Compound 12 shown in Table 2 was obtained. The physical properties of said compound are shown in Table 2.

PREPARATION EXAMPLE 13

The same procedure as in Preparation Example 9 was taken except that the compound obtained in Preparation Example 8 (3) was used in place of the compound obtained in Preparation Example 2 (3). The physical properties of said compound are shown in Table 2.

PREPARATION EXAMPLE 14

The procedure as in Preparation Example 9 was taken except that the compound represented by the formula:

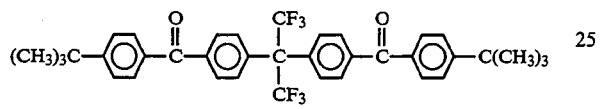

was used in place of the diketone compound of Preparation Example 9, and Compound 14 shown in Table 2 was obtained. The physical properties of said compound are shown in Table 2.

PREPARATION EXAMPLE 15

Preparation Example 1 of Oligomer Compound (1) Production of Phosphorus Compound containing Arylene Group 9.0 g of 4,4'-bis(bromomethyl)biphenyl and 11 g of triethyl phosphite were stirred on oil bath in a stream of argon for 6 hours while heated at 140° C. Then, the excess triethyl phosphite was vacuum-distilled away. After left overnight, 9.5 g of a white crystal (yield :80%) was obtained. The melting point of the resulting white crystal was 97.0° to 100.0° C.

$^1$H-NMR of the above compound is as follows.
$^1$H-NMR (CDCl$_3$, TMS)
$\delta$=7.0 to 7.6 ppm (m; 8H, biphenylene ring —H)
$\delta$=4.0 ppm (q; 8H, ethoxymethylene —CH$_2$)
$\delta$=3.1 ppm (d; 4H, J=20 Hz ($^{31}$P - $^1$H coupling) P—CH$_2$)
$\delta$=1.3 ppm (t; 12H, ethoxymethyl —CH$_3$)

The results as above confirmed that the resulting white crystal was a phosphonate containing arylene group represented by the formula:

(2) Preparation of Oligomer Compound 2.1 g (0.0016 mol) of the phosphoric acid ester compound obtained in Preparation Example 15 (1) was added in a stream of argon to 50 ml of dimethyl sulfoxide to be suspended, and subsequently 1.0 g (0.0048 mol ) of the compound obtained in Preparation Example 9

TABLE 2

| Com- pound | | Composition Formula (Molecular Weight) | Melting Point (°C.) | $^1$H-NMR (CDCl$_3$, TMS) | State | Mass Spectrum | Result of Elementary Analysis (%) ( ): Values in parentheses are theoretical |
|---|---|---|---|---|---|---|---|
| Preparation Example 10 | (71) | C$_{91}$H$_{81}$O$_2$ (1204) | — | $\delta$ = 6.6~7.4 ppm (m; 56H, Aromatic Ring and H of —CH=C) $\delta$ = 1.3 ppm (s; 18H, t-butyl group —CH$_3$) $\delta$ = 1.7 ppm (s; 6H, Propyl group —CH$_3$) | Yellow Amorphous | m/Z = 1204 | C: 90.81 (90.66) H: 6.45 (6.69) N: 0.00 (0.00) |
| Preparation Example 11 | (72) | C$_{76}$H$_{66}$O$_4$S (1074) | — | $\delta$ = 6.7~8.0 ppm (m; 48H, Aromatic Ring and H of —CH=C) $\delta$ = 1.3 ppm (s; 18H, t-butyl group —CH$_3$) | Pale Yellow Amorphous | m/Z = 1074 | C: 84.51 (84.88) H: 5.93 (6.19) N: 0.00 (0.00) |
| Preparation Example 12 | (73) | C$_{70}$H$_{66}$O$_2$F$_6$ (1160) | — | $\delta$ = 6.9~7.6 ppm (m; 48H, Aromatic Ring and H of —CH=C) $\delta$ = 1.3 ppm (s; 18H, t-butyl group —CH$_3$) | Pale Yellow Amorphous | m/Z = 1160 | C: 81.88 (81.70) H: 5.57 (5.73) N: 0.00 (0.00) |
| Preparation Example 13 | (74) | C$_{94}$H$_{78}$O$_2$ 91238) | 273.0~274.0 | $\delta$ = 6.7~7.5 ppm (m; 56H, Aromatic Ring and H of —CH=C) $\delta$ = 1.5 ppm (s; 18H; t-butyl group —CH$_3$) | Pale Yellow Powder | m/Z = 1238 | C: 89.94 (91.08) H: 6.28 (6.34) N: 0.00 (0.00) |
| Preparation Example 14 | (75) | C$_{79}$H$_{66}$F$_6$ (1128) | 233.0~234.0 | $\delta$ = 6.9~7.6 ppm (m; 48H, Aromatic Ring and H of —CH=C) $\delta$ = 1.5 ppm (s, 18H, t-butyl group —CH$_3$) | Pale Green Powder | m/Z = 1128 | C: 83.82 (84.02) H: 5.67 (5.89) N: 0.00 (0.00) |

(3) and 1.0 g (0.0089 mol) of potassium-t-butoxide were added. The resulting red brown suspension was stirred

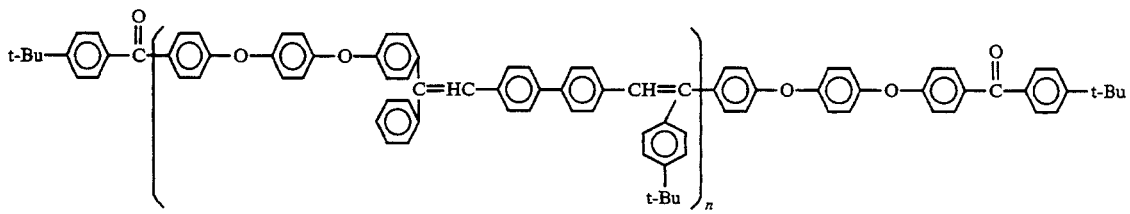

for 5 hours at room temperature, and left overnight. Then, the solution was distilled away, and 100 ml of methanol was put in the reaction mixture, and the precipitated pale yellow powder was taken by filtration. The pale yellow powder was purified on a silica gel column (solvent: CHCl₃, column: 40 mm in inner diameter×200 mm in length) to obtain 0.8 g of pale yellow powder.

The result of mass spectrometry showed that the compound was a mixture comprising the component represented by the chemical formula:

(herein, W indicates a relative strength, being an integer of 1 to 4)

The relative strength was:

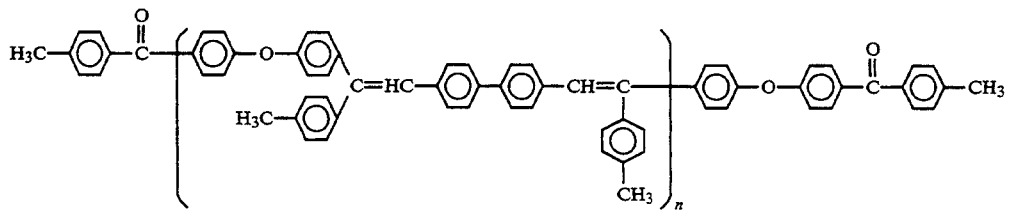

W(1):W(2):W(3):W(4)=9:3:1: 1.

As the result of IR spectrum (KBr pellet method) of the mixture, an absorption at $\nu_{c-o}$ 730 cm$^{-1}$ was detected, and accordingly it was shown that the terminal was aldehyde.

PREPARATION EXAMPLE 16

Preparation Example of Oligomer Compound 2

1.5 g (0.0033 mol) of phosphoric acid ester compound obtained in Preparation Example 15 (1) was added in a stream of argon gas to 100 ml of dimethylsulfoxide to be suspended, and subsequently, 2.0 g (0.0034 mol) of the compound obtained in Preparation Example 9 (3) and 0.8 g (0.0071 mol) of potassium-t-butoxide were added. The resulting red brown suspension was stirred for 5 hours at 40° C., and left overnight. After the solution was distilled away, 100 ml of methanol was put into the reaction mixture, and the precipitated pale yellow powder was taken by filtration. The soluble portion of methylene chloride in pale yellow powder alone was purified on a silica gel column (solvent: CHCl₃, column: 40 mm in inner diameter×200 mm in length) to obtain 0.13 g of a pale yellow powder. The melting point of the compound was 300° C. or more. Measurement of the mass spectrum of that compound showed that the compound comprises the component represented by the following chemical formula.

PREPARATION EXAMPLE 17

Preparation Example of Oligomer Compound 3

The same procedure as in Preparation Example 16 was repeated except 4,4-bis(p-tollyl)phenylether represented by

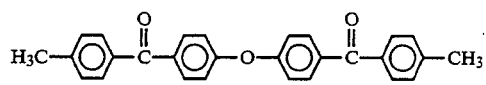

1 place of diketone compound used in Preparation Example 16, and the compound as under was obtained.

Measurement of the mass spectrum of the compound showed that the compound comprises the component wherein n=1 to 4. As the result of measuring the IR spectrum of that mixture (KBr pellet method), an absorption was found at $\nu_{c-o}$=1700 cm$^{-1}$.

EXAMPLE 1

Indium tin oxide (ITO) was provided on a 25 mm×75 mm×1.1 mm glass substrate in a 100 nm thick film formed by the vapor deposition method to obtain a transparent supporting substrate (manufactured by HOYA Co., Ltd.).

Said transparent supporting substrate was attached to the substrate holder of a commercially available vapor deposition system (manufactured by ULVAC Co., Ltd.), 200 mg of TPDA was placed in an electrically-heated boat made of molybdenum, and 200 mg of the compound (DSBC) represented by the formula [VIII] obtained in the Preparation Example 1 was placed in another boat made of molybdenum. The pressure in the vacuum chamber was decreased to 1×10$^{-4}$ Pa.

After that, said boat containing TPDA was heated to 215° to 220° C., and TPDA was vapor-deposited on the transparent supporting substrate at a deposition rate of 0.1 to 0.3 nm/sec, to obtain a hole injection layer of 70 nm in thickness. In this deposition process, the substrate was at room temperature.

Without taking the substrate out of the vacuum chamber, DSBC from another boat was laminate-deposited in thickness of 80 nm on the hole injection layer, to form the emitting layer. The deposition was performed with the boat temperature of 330° C. or so, at a deposition rate of 0.2 to 0.4 nm/sec, and the substrate was at room temperature.

The substrate was taken out of the vacuum chamber, and a stainless steel mask was placed on said emitting layer, which was then attached to the substrate holder again.

In the electrically-heated boat made of molybdenum, 1 g of magnesium ribbon was placed, and 500 mg of indium was placed in another electrically-heated boat made of molybdenum. Then the pressure in the vacuum chamber was decreased to $2 \times 10^{-4}$ Pa, and subsequently indium began to be deposited at the deposition rate of 0.03 to 0.08 nm/sec, and simultaneously magnesium in another boat began to be deposited at a deposition rate of 1.7 to 2.8 nm/sec. The temperatures of the boats each containing indium and magnesium were 800° C. and 500° C., respectively.

Under the above conditions, a mixed metal electrode of magnesium and indium was laminate-deposited in thickness of 150 nm as the opposite electrode on the emitting layer to form the element. When said element is formed, the emitting layer did not get opaque visually.

Upon applying a DC voltage of 7.5 V to the resulting element with the ITO electrode as the anode and the mixed metal electrode of magnesium and indium as the cathode, a current of approximately 5.56 mA/cm$^2$ passed and the emitting light was Blue in chromaticity coordinates. The peak wavelength determined by spectrometry was 477 nm, the brightness was 200 cd/m$^2$ and the efficiency was 1.51 l m/W.

SEM photograph just after the formation of said element showed that a uniform and amorphous thin film was formed. The thin film forming property (1) was (C) rank. After 6 months, SEM photograph showed that neither precipitation of crystal nor pinhole was observed. The thin film maintaining property (2) was (C) rank.

EXAMPLE 2

ITO was provided on a 25 mm×75 mm×1.1 mm glass substrate in a 100 nm thick film formed by the vapor deposition method to obtain a transparent supporting substrate (manufactured by HOYA Co., Ltd.).

Said transparent supporting substrate was attached to the substrate holder of a commercially available vapor deposition system (manufactured by ULVAC Co., Ltd.), 200 mg of TPDA was placed in an electrically-heated boat made of molybdenum, and 200 mg of the compound (DPVSPC) represented by the formula [IX] was placed in another boat made of molybdenum.

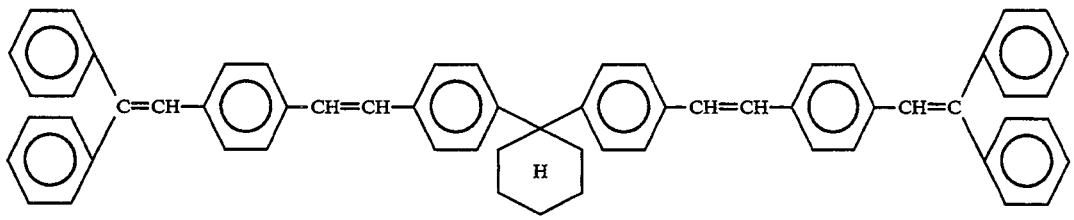

The pressure in the vacuum chamber was decreased to $1 \times 10^{-4}$ Pa.

After that, said boat containing TPDA was heated to 215° to 220° C., and TPDA was vapor-deposited on the transparent supporting substrate at a deposition rate of 0.1 to 0.3 nm/sec, to obtain a hole injection layer of 70 nm in thickness. In this deposition process, the substrate was at room temperature.

Without taking the substrate out of the vacuum chamber, DPVSPC from another boat was laminate-deposited in thickness of 80 nm on the hole injection layer, to form the emitting layer. The deposition was performed with the boat temperature of 320° C. or so, at a deposition rate of 0.2 to 0.4 nm/sec, and the substrate was at room temperature.

The substrate was taken out of the vacuum chamber, and a stainless steel mask was placed on said emitting layer, which was then attached to the substrate holder again.

In the electrically-heated boat made of molybdenum, 1 g of magnesium ribbon was placed, and 500 mg of indium was placed in another electrically-heated boat made of molybdenum.

Then the pressure in the vacuum chamber was decreased to $2 \times 10^{-4}$ Pa, and subsequently indium began to be deposited at the deposition rate of 0.03 to 0.08 nm/sec, and simultaneously magnesium in another boat began to be deposited at a deposition rate of 1.7 to 2.8 nm/sec. The temperatures of the boats each containing indium and magnesium were 800° C. and 500° C. respectively. When said element is formed, the emitting layer did not get opaque visually.

Under the above conditions, a mixed metal electrode of magnesium and indium was laminate-deposited in thickness of 150 nm as the opposite electrode on the emitting layer to form the element.

Upon applying a DC voltage of 12.5 V to the resulting element with the ITO electrode as the anode and the mixed metal electrode of magnesium and indium as the cathode, a current of approximately 210 mA/cm$^2$ passed and the emitting light was Greenish Blue in chromaticity coordinates. The peak wavelength determined by spectrometry was 484 nm, and the brightness was 200 cd/m$^2$.

SEM photograph just after the formation of said element showed that a uniform and amorphous thin film was formed. The thin film forming property (1) was (C) rank. After 6 months, SEM photograph showed that neither precipitation of crystal nor pinhole was observed and the thin film maintaining property (2) was (C) rank. Further, Tg was 82.1° C. and the heat resistant thin film property (3) was (C) rank.

The EL emitting light was hardly changed and the thin film property was evidently improved as seen from the Comparative Example 1.

EXAMPLE 3

ITO was provided on a 25 mm×75 mm×1.1 mm glass substrate in a 100 nm thick film formed by the vapor deposition method to obtain a transparent supporting substrate (manufactured by HOYA Co., Ltd.).

Said transparent supporting substrate was attached to the substrate holder of a commercially available vapor deposition system (manufactured by ULVAC Co., Ltd.), 200 mg of TPDA was placed in an electrically-heated boat made of molybdenum, and 200 mg of the compound (DPVSPE) represented by the formula [X] was placed in another boat made of molybdenum.

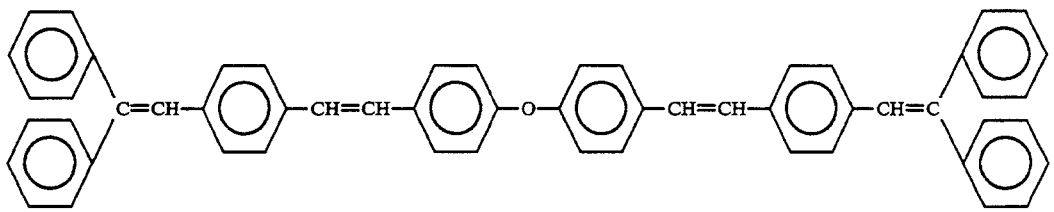

The pressure in the vacuum chamber was decreased to $1 \times 10^{-4}$ Pa.

After that, said boat containing TPDA was heated to 215° to 220° C., and TPDA was vacuum-deposited on the transparent supporting substrate at a deposition rate of 0.1 to 0.3 nm/sec, to obtain a hole injection layer of 70 nm in thickness. In this deposition process, the substrate was at room temperature.

Without taking the substrate out of the vacuum chamber, DPVSPE from another boat was laminate-deposited in thickness of 80 nm on the hole injection layer, to form the emitting layer. The deposition was performed with the boat temperature of 320° C. or so, at a deposition rate of 0.2 to 0.4 nm/sec, and the substrate was at room temperature.

The substrate was taken out of the vacuum chamber, and a stainless steel mask was placed on said emitting layer, which was then attached to the substrate holder again.

In the electrically-heated boat made of molybdenum, 1 g of magnesium ribbon was placed, and 500 mg of indium was placed in another electrically-heated boat made of molybdenum. Then the pressure in the vacuum chamber was decreased to $2 \times 10^{-4}$ Pa, and subsequently indium began to be deposited at the deposition rate of 0.03 to 0.08 nm/sec, and simultaneously magnesium in another boat began to be deposited at a deposition rate of 1.7 to 2.8 nm/sec. The temperatures of the boats each containing indium and magnesium were 800° C. and 500° C., respectively.

Under the above conditions, a mixed metal electrode of magnesium and indium was laminate-deposited in thickness of 150 nm as the opposite electrode on the emitting layer to form the element. When said element is formed, the emitting layer did not get opaque visually.

Upon applying a DC voltage of 12.5 V to the resulting element with the ITO electrode as the anode and the mixed metal electrode of magnesium and indium as the cathode, a current of approximately 266 mA/cm² passed and the emitting light was Greenish Blue in chromaticity coordinates. The peak wavelength determined by spectrometry was 483 nm, and the brightness was 400 cd/m².

SEM photograph just after the formation of said element showed that a uniform and amorphous thin film was formed. The thin film forming property (1) was (C) rank. After 6 months, SEM photograph showed that neither precipitation of crystal nor pinhole was observed. The thin film maintaining property (2) was (C) rank. Further, Tg was 71.3° C. and the heat resistant thin film property (3) was (C) rank.

The EL emitting light was hardly changed and the thin film property was evidently improved as seen from the Comparative Example 1.

EXAMPLE 4

ITO was provided on a 25 mm×75 mm×1.1 mm glass substrate in a 100 nm thick film formed by the vapor deposition method to obtain a transparent supporting substrate (manufactured by HOYA Co., Ltd.).

Said transparent supporting substrate was attached to the substrate holder of a commercially available vapor deposition system (manufactured by ULVAC Co., Ltd.), 200 mg of TPDA was placed in an electrically-heated boat made of molybdenum, and 200 mg of the compound (DPVSPM) represented by the formula [XI] was placed in another boat made of molybdenum.

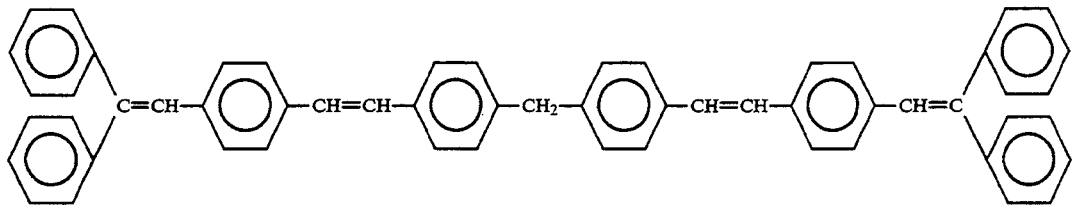

The pressure in the vacuum chamber was decreased to $1 \times 10^{-4}$ Pa.

After that, said boat containing TPDA was heated to 215° to 220° C., and TPDA was vapor-deposited on the transparent supporting substrate at a deposition rate of 0.1 to 0.3 nm/sec, to obtain a hole injection layer of 70 nm in thickness. In this deposition process, the substrate was at room temperature.

Without taking tile substrate out of the vacuum chamber, DPVSPM from another boat was laminate-deposited in thickness of 80 nm on the hole injection layer, to form the emitting layer. The deposition was performed with the boat temperature of 310° C. or so, at a deposition rate of 0.2 to 0.4 nm/sec, and the substrate was at room temperature.

The substrate was taken out of the vacuum chamber, and a stainless steel mask was placed on said emitting layer, which was then attached to the substrate holder again.

In the electrically-heated boat made of molybdenum, 1 g of magnesium ribbon was placed, and 500 mg of indium was placed in another electrically-heated boat made of molybdenum.

Then the pressure in the vacuum chamber was decreased to $2 \times 10^{-4}$ Pa, and subsequently indium began to be deposited at the deposition rate of 0.03 to 0.08 nm/sec, and simultaneously magnesium in another boat began to be deposited at a deposition rate of 1.7 to 2.8 rim/sec. The temperatures of the boats each containing indium and magnesium were 800° C. and and 500° C., respectively.

Under the above conditions, a mixed metal electrode of magnesium and indium was laminate-deposited in thickness of 150 nm as the opposite electrode on the emitting layer to form the element. When said element is formed, the emitting layer did not get opaque visually.

Upon applying a DC voltage of 15 V to the resulting element with the ITO electrode as the anode and the mixed metal electrode of magnesium and indium as the cathode, a current of approximately 200 mA/cm$^2$ passed and the emitting light was Blue Green in chromaticity coordinates. The peak wavelength determined by spectrometry was 488 nm, the brightness was 300 cd/m$^2$.

SEM photograph just after the formation of said element showed that a uniform and amorphous thin film was formed. The thin film forming property (1) was (C) rank. After 6 months, SEM photograph showed that neither precipitation of crystal nor pinhole was observed. The thin film maintaining property (2) was (C) rank. Further, Tg was 71.9° C. and the heat resistant thin film property (3) was (C) rank.

The EL emitting light was hardly changed and the thin film property was evidently improved as seen from the Comparative Example 1.

EXAMPLE 5

ITO was provided on a 25 mm×75 mm×1.1 mm glass substrate in a 100 nm thick film formed by the vapor deposition method to obtain a transparent supporting substrate (manufactured by HOYA Co., Ltd.).

Said transparent supporting substrate was attached to the substrate holder of a commercially available vapor deposition system (manufactured by ULVAC Co., Ltd.), 200 mg of TPDA was placed in an electrically-heated boat made of molybdenum, and 200 mg of the compound (BDMPVPE) (Tg=66.6° C.) represented by the formula [XII] was placed in another boat made of molybdenum.

The pressure in the vacuum chamber was decreased to $1 \times 10^{-4}$ Pa.

After that, said boat containing TPDA was heated to 215° to 220° C., and TPDA was vapor-deposited on the transparent supporting substrate at a deposition rate of 0.1 to 0.3 nm/sec, to obtain a hole injection layer of 60 nm in thickness. In this deposition process, the substrate was at room temperature.

Without taking the substrate out of the vacuum chamber, BDMPVPE from another boat was laminate-deposited in thickness of 60 nm on the hole injection layer, to form the emitting layer. The deposition was performed with the boat temperature of 310° C. or so, at a deposition rate of 0.2 to 0.4 nm/sec, and the substrate was at room temperature.

The substrate was taken out of the vacuum chamber, and a stainless steel mask was placed on said emitting layer, which was then attached to the substrate holder again.

In the electrically-heated boat made of molybdenum, 1 g of magnesium ribbon was placed, and 500 mg of indium was placed in another electrically-heated boat made of molybdenum.

Then the pressure in the vacuum chamber was decreased to $2 \times 10^{-4}$ Pa, and subsequently indium began to be deposited at the deposition rate of 0.03 to 0.08 nm/sec, and simultaneously magnesium in another boat began to be deposited at a deposition rate of 1.7 to 2.8 nm/sec. The temperatures of the boats each containing indium and magnesium were 800° C. and 500° C. respectively.

Under the above conditions, a mixed metal electrode of magnesium and indium was laminate-deposited in thickness of 150 nm as the opposite electrode on the emitting layer to form the element. When said element is formed, the emitting layer did not get opaque visually.

Upon applying a DC voltage of 15 V to the resulting element with the ITO electrode as the anode and the mixed metal electrode of magnesium and indium as the cathode, a current of approximately 154 mA/cm$^2$ passed and the emitting light was Blue in chromaticity coordinates. The peak wavelength determined by spectrometry was 485 nm, the brightness was 30 cd/m$^2$.

SEM photograph just after the formation of said element showed that a uniform and amorphous thin film was formed. The thin film forming property (1) was (C) rank. After months, SEM photograph showed that neither precipitation of crystal nor pinhole was observed. The thin film maintaining property (2) was (C) rank. Further, Tg was 66.6° C. and the heat resistant thin film property (3) was (C) rank.

EXAMPLE 6

ITO was provided on a 25 mm×75 mm×1.1 mm glass substrate in a 100 nm thick film formed by the

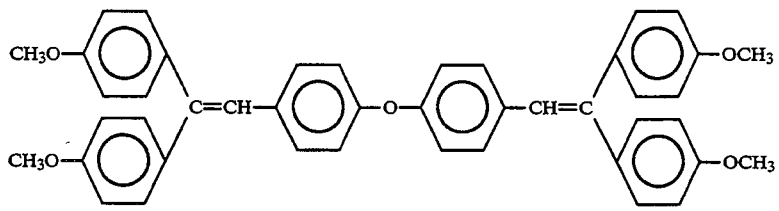

vapor deposition method to obtain a transparent supporting substrate (manufactured by HOYA Co., Ltd.).

Said transparent supporting substrate was attached to the substrate holder of a commercially available vapor deposition system (manufactured by ULVAC Co., Ltd.), 200 mg of TPDA was placed in an electrically-heated boat made of molybdenum, and 200 mg of the compound (DPVSTPE) (Tg=91.7° C.) represented by the formula [XIII] was placed in another boat made of molybdenum.

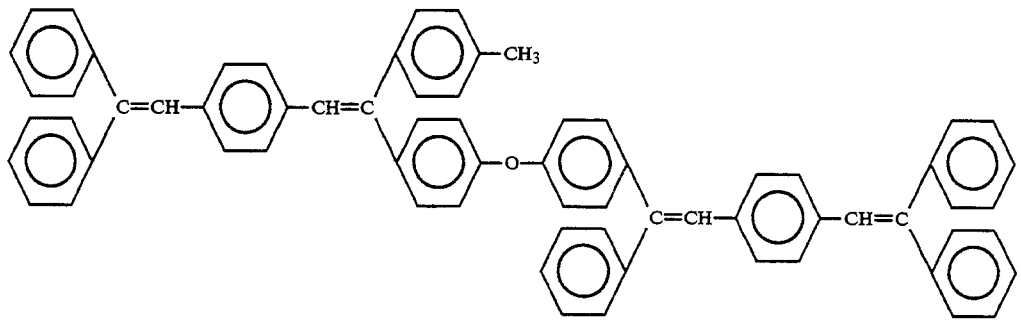

The pressure in the vacuum chamber was decreased to $1 \times 10^{-4}$ Pa.

After that, said boat containing TPDA was heated to 215° to 220° C., and TPDA was vapor-deposited on the transparent supporting substrate at a deposition rate of 0.1 to 0.3 nm/sec, to obtain a hole injection layer of 70 nm in thickness. In this vacuum deposition process, the substrate was at room temperature.

Without taking the substrate out of the vacuum chamber, DPVSTPE from another boat was laminate-deposited in thickness of 60 nm on the hole injection layer, to form the emitting layer. The deposition was performed with the boat temperature of 405° C. or so, at a deposition rate of 0.2 to 0.4 nm/sec, and the substrate was at room temperature.

The substrate was taken out of the vacuum chamber, and a stainless steel mask was placed on said emitting layer, which was then attached to the substrate holder again.

In the electrically-heated boat made of molybdenum, 1 g of magnesium ribbon was placed, and 500 mg of indium was placed in another electrically-heated boat made of molybdenum.

Then the pressure in the vacuum chamber was decreased to $2 \times 10^{-4}$ Pa, and subsequently indium began to be deposited at the deposition rate of 0.03 to 0.08 nm/sec, and simultaneously magnesium in another boat began to be deposited at a deposition rate of 1.7 to 2.8 nm/sec. The temperatures of the boats each containing indium and magnesium were 800° C. and 500° C., respectively.

Under the above conditions, a mixed metal electrode of magnesium and indium was laminate-deposited in thickness of 150 nm as the opposite electrode on the emitting layer to form the element. When said element is formed, the emitting layer did not get opaque visually.

Upon applying a DC voltage of 12 V to the resulting element with the ITO electrode as the anode and the mixed metal electrode of magnesium and indium as the cathode, a current of approximately 77 mA/cm$^2$ passed and the emitting light was Blue Green in chromaticity coordinates. The peak wavelength determined by spectrometry was 489 nm, and the brightness was 700 cd/m$^2$.

SEM photograph just after the formation of said element showed that a uniform and amorphous thin film was formed. The thin film forming property (1) was (C) rank. After months, SEM photograph showed that neither precipitation of crystal nor pinhole was observed. The thin film maintaining property (2) was (C) rank. Further, Tg was 91.7° C. and the heat resistant thin film property (3) was (C) rank.

EXAMPLES 7 AND 8

The same procedure was repeated as in Example 6 using the materials shown in Table 3. The results are shown in Table 3.

TABLE 3

| | Material of Emitting Layer (compound) | Material of Hole Injection Layer & Film Thickness (nm) | Film Thickness of Emitting Layer (nm) | Material of Emission Boat Temperature (°C.) | Applied Voltage (V) |
|---|---|---|---|---|---|
| Example 7 | (43) | TPDA 60 | 60 | 312 | 15 |
| Example 8 | (76) | TPDA 70 | 70 | 246 | 12.5 |

| | Current Density (mA/cm$^2$) | Brightness (cd/m$^2$) | Emitting Light (λmax) | Thin film Forming Property | Thin film Maintaining Property | Heat Resistant Thin Film Property |
|---|---|---|---|---|---|---|
| Example 7 | 16 | 20 | Blue 477 nm | C | C | C |
| Example 8 | 100 | 1030 | Greenish Blue 488 nm | C | C | C |

EXAMPLE 9

(ITO/hole injection layer/emitting layer/electron injection layer/Mg:In)

Glass substrate (25×75×1.1 mm, manufactured by HOYA Co., Ltd.) equipped with ITO transparent electrode of 100 nm in film thickness was used as a transparent supporting substrate, and said substrate was ultrasonically washed with isopropyl alcohol for 5 minutes and then washed by dipping in isopropyl alcohol, and further washed with UV ozone washing apparatus produced by Samco International Co., Ltd. Said transparent supporting substrate was dried using dry nitrogen gas and attached to the substrate holder of commercially available vacuum vapor deposition system. On the other hand, 200 mg of N,N'-diphenyl-N,N'-di(3-methylphenyl)-4,4'-diaminobiphenyl (TPDA) was placed in an electrically-heated boat made of molybdenum, 200 mg of the compound represented by the formula (A) was placed in another electrically-heated boat made of molybdenum, and further t-BuPBD [the compound represented by the formula (B)] was placed in the other boat made of molybdenum, which were attached to a vacuum vapor deposition system.

Next, the pressure in the vacuum chamber was decreased to $4 \times 10^{-6}$ Pa. After that, electricity passed to the above-described boat containing TPDA and the boat was heated to 20° C. and TPDA was vapor-deposited on the transparent supporting substrate at a deposition rate of 0.1 to 0.7 nm/sec, to provide a hole injection transport layer of 50 nm in thickness. Further, electricity passed to the above-described boat containing the compound represented by the formula (A), and the boat was heated to 360° C. and the compound was vapor-deposited on the above-described hole injection transport layer at a deposition rate of 0.1 to 0.3 nm/sec, to provide an emitting layer of 60 nm in thickness. Still further, electricity passed to the above-described boat containing t-BuPBD, and the boat was heated to 160° C. and t-BuPBD was vapor-deposited on the above emitting layer at a deposition rate of 0.1 to 0.4 nm/sec, to provide an electron injection layer. The temperature of said substrate during the vapor deposition was room temperature.

Next, the vacuum chamber was opened and the stainless steel mask was provided on said emitting layer. On the other hand, 3 g of magnesium was placed in an electrically-heated boat made of molybdenum, indium was placed in another electrically-heated filament, and the pressure in the vacuum chamber was decreased to $2 \times 10^{-6}$ Pa again. Then, electricity passed to the boat containing magnesium, magnesium was vapor-deposited at a deposition rate of 4 to 5 nm/sec, and simultaneously indium was heated and copper was vapor-deposited at a deposition rate of 0.2 to 0.3 nm/sec, which was the opposite electrode consisting of the mixture of magnesium and indium. Thus, the aimed EL element could be formed.

Upon applying a DC voltage of 7.5 V to the resulting element with the ITO electrode as the anode and the opposite electrode of a mixture of magnesium and indium as the cathode, a current of approximately 28 mA/cm² passed. The peak wavelength was 156 nm and the emitting light of Purplish Blue was obtained. The brightness was 80 cd/m².

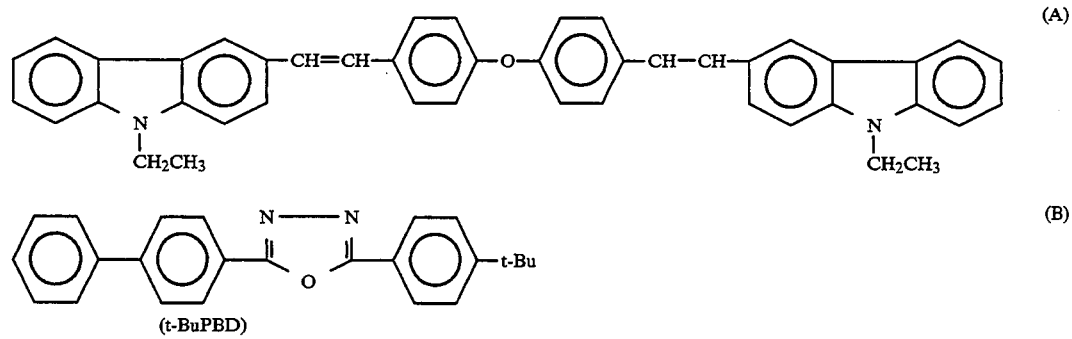

SEM photograph just after the formation of the element showed that a uniform and amorphous thin film was formed and the thin film forming property (1) was (C) rank. After 6 months, gEM photograph showed that neither precipitation of crystal nor pinhole was observed, and the thin film maintaining property (2) was (C) rank.

EXAMPLE 10

(ITO/hole injection layer/emitting layer/electron injection layer/MS:In)

Glass substrate (25×75×1.1 mm, manufactured by HOYA Co., Ltd.) equipped with ITO transparent electrode of 100 nm in film thickness was used as a transparent supporting substrate, and said substrate was ultrasonically washed with isopropyl alcohol for 5 minutes and then washed by dipping in isopropyl alcohol, and further washed with UV ozone washing apparatus produced by Samco International Co., Ltd. Said transparent supporting substrate was dried using dry nitrogen gas and attached to the substrate holder of commercially available vacuum vapor deposition system. On the other hand, 200 mg of N,N'-diphenyl-N,N'-di(3-methylphenyl)-4,4'-diaminobiphenyl (TPDA) was placed in an electrically-heated boat made of molybdenum, 200 mg of the compound represented by the formula (A) was placed in another electrically-heated boat made of molybdenum, and further t-BuPBD [the compound represented by the formula (B)]was placed in the other boat made of molybdenum, which were attached to a vacuum vapor deposition system.

Next, the pressure in the vacuum chamber was decreased to $4 \times 10^{-6}$ Pa. After that, electricity passed to the above-described boat containing TPDA and the boat was heated to 220° C., and TPDA was vapor-deposited on the transparent supporting substrate at a deposition rate of 0.1 to 0.7 nm/sec, to provide a hole injection transport layer of 50 nm in thickness. Further, electricity passed to the above-described boat containing the compound represented by the formula (A), and the boat was heated to 246° C. and the compound was vapor-deposited on the above-described hole injection transport layer at a deposition rate of 0.1 to 0.3 nm/sec, to provide an emitting layer of 60 nm in thickness. Still further, electricity passed to the above-described boat containing t-BuPBD, and the boat was heated to 160° C. and t-BuPBD was vapor-deposited on the above emitting layer at a deposition rate of 0.1 to 0.4 nm/sec, to provide an electron injection layer. The temperature of said substrate during the vapor deposition was room temperature.

Next, the vacuum chamber was opened and the stainless steel mask was provided on said emitting layer. On the other hand, 3 g of magnesium was placed in an electrically-heated boat made of molybdenum, indium was placed in another electrically-heated filament, and Upon applying a DC voltage of 17 V to the resulting element with the ITO electrode as the anode and the opposite electrode of a mixture of magnesium and indium as the cathode, a current of approximately 14 mA/cm$^2$ passed. The peak wavelength was 482 nm and the emitting light of Blue was obtained. The brightness was 300 cd/m$^2$.

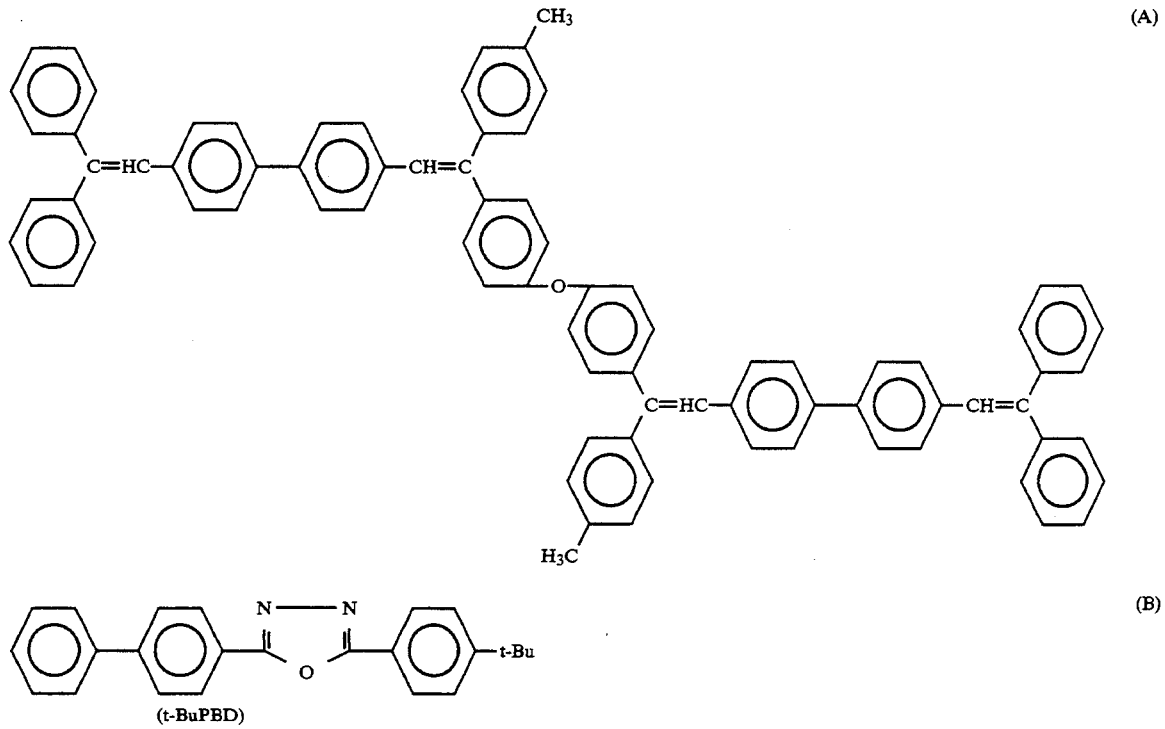

(A)

(B)

(t-BuPBD)

the pressure of the vacuum chamber was decreased to 2×10$^{-6}$ Pa again. Then, electricity passed to the boat containing magnesium, magnesium was vapor-deposited at a deposition rate of 4 to 5 nm/sec, and simultaneously indium was heated and copper was vapor-deposited at a deposition rate of 0.2 to 0.3 nm/sec, which was the opposite electrode consisting of the mixture of magnesium and indium. Thus, the aimed EL element could be formed.

EXAMPLES 11 TO 15

The same procedure was repeated as in Example 10 and the results were shown in Table 4.

EXAMPLES 16 TO 18

Example of the EL element using oligomer compound as the material for emission

The same procedure was repeated as in Example 10 and the results were shown in Table 4.

TABLE 4

| | Material of Emitting Layer (compound) | Material of Hole Injection Layer & Film Thickness (nm) | Film Thickness of Emitting Layer (nm) | Material of Electron Injection Layer & Film Thickness (nm) | Material of Emission Boat Temperature (°C.) | Applied Voltage (V) | Current Density (mA/cm$^2$) |
|---|---|---|---|---|---|---|---|
| Example 11 | (77) | TPDA 60 | 60 | PBD 20 | 395~402 | 10 | 16.8 |
| | | | | | | 12.5 | 56.0 |
| Example 12 | (71) | TPDA 60 | 70 | PBD 20 | 400 | 12.5 | 35.0 |
| Example 13 | (72) | TPDA 60 | 40 | PBD 20 | 410~413 | 7.5 | 9.1 |
| | | | | | | 10 | 48.0 |
| Example 14 | (73) | TPDA 60 | 40 | PBD 20 | 398~403 | 10 | 10.0 |
| Example 15 | (74) | TPDA 60 | 40 | PBD 20 | 410~415 | 10 | 17.0 |
| | | | | | | 12.5 | 52.5 |
| Example 16 | Preparation Example 15 | TPDA 60 | 40 | PBD 20 | 410~415 | 12.5 | 30.0 |
| Example 17 | Preparation Example 16 | TPDA 60 | 40 | PBD 20 | 400~405 | 10 | 17.0 |
| Example 18 | Preparation Example 17 | TPDA 60 | 40 | PBD 20 | 216~219 | 15 | 28.0 |

| | Brightness (cd/m$^2$) | Emitting Light (λmax) | Emitting Efficiency (lm/W) | Thin film Forming Property | Thin film Maintaining Property | Heat Resistant Thin Film Property |
|---|---|---|---|---|---|---|
| Example 11 | 55 | Greenish Blue | 1.0 | C | C | C |
| | 1030 | 488 nm | 0.46 | | | |

TABLE 4-continued

| | | | | | | |
|---|---|---|---|---|---|---|
| Example 12 | 700 | Blue Green 487 nm | 0.5 | C | C | C |
| Example 13 | 50 200 | Greenish Blue 482 nm | 0.23 0.13 | C | C | C |
| Example 14 | 250 | Greenish Blue 486 nm | 0.79 | C | C | C |
| Example 15 | 500 1000 | Blue 480 nm | 0.94 0.48 | C | C | C |
| Example 16 | 500 | Blue 480 nm | 0.42 | C | C | C |
| Example 17 | 300 | Greenish Blue 488 nm | 0.52 | C | C | C |
| Example 18 | 60 | Green 501 nm | 0.04 | C | C | C |

COMPARATIVE EXAMPLE 1

ITO was provided on a 25 mm×75 mm×1.1 mm glass substrate in a 100 nm thick film formed by the vapor deposition method to obtain a transparent supporting substrate (manufactured by HOYA Co., Ltd.).

Said transparent supporting substrate was attached to the substrate holder of a commercially available vapor deposition system (manufactured by ULVAC Co., Ltd.), 200 mg of TPDA was placed in an electrically-heated boat made of molybdenum, and 200 mg of the compound (DPVSB) (Tg=23.1° C.) represented by the formula [XIV] was placed in another boat made of molybdenum.

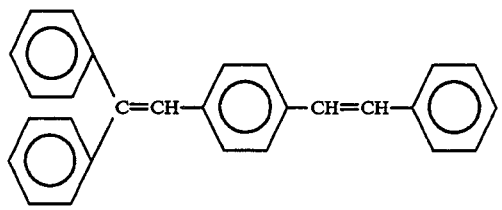

[XIV]

The pressure in the vacuum chamber was decreased to $1 \times 10^{-4}$ Pa.

After that, said boat containing TPDA was heated to 215° to 220° C., and TPDA was vapor-deposited on the transparent supporting substrate at a deposition rate of 0.1 to 0.3 nm/sec, to obtain a hole injection layer of 70 nm in thickness. In this deposition process, the substrate was at room temperature.

Without taking the substrate out of the vacuum chamber, DPVSB from another boat was laminate-deposited in thickness of 80 nm on the hole injection layer, to form the emitting layer. The deposition was performed with the boat temperature of 210° C. or so, at a deposition rate of 0.2 to 0.4 nm/sec, and the substrate was at room temperature.

The substrate was taken out of the vacuum chamber, and a stainless steel mask was placed on said emitting layer, which was then attached to the substrate holder again.

In the electrically-heated boat made of molybdenum, 1 g of magnesium ribbon was placed, and 500 mg of indium was placed in another electrically-heated boat made of molybdenum. Then the pressure in the vacuum chamber was decreased to $2 \times 10^{-4}$ Pa, and subsequently indium began to be deposited at the deposition rate of 0.03 to 0.08 nm/sec, and simultaneously magnesium in another boat began to be deposited at a deposition rate of 1.7 to 2.8 nm/sec. The temperatures of the boats each containing indium and magnesium were 800° C. and 500° C., respectively.

Under the above conditions, a mixed metal electrode of magnesium and indium was laminate-deposited in thickness of 150 nm as the opposite electrode on the emitting layer to form the element. When said element is formed, the emitting layer did not get opaque visually.

Upon applying a DC voltage of 10 V to the resulting element with the ITO electrode as the anode and the mixed metal electrode of magnesium and indium as the cathode, a current of approximately 25 mA/cm$^2$ passed and the emitting light was Blue in chromaticity coordinates. The peak wavelength determined by spectrometry was 482 nm, the brightness was 3 cd/m$^2$.

In said element, crystallization began to be carried out while said element was formed. Further, after the formation of the element, the surface of thin film got opaque due to progress of crystallization. When one night elapsed, emitting light could not be obtained due to the deterioration of EL element. The thin film forming property (1) was (B) rank. The thin film maintaining property (2) was (A) rank. Further, Tg was 23.1° C. and heat resistant thin film property (3) was (B) rank.

INDUSTRIAL AVAILABILITY

As described above, in the organic EL device of the present invention, the light emitting efficiency and the wavelength of the emission do not lower the ability of the desired compound, yet it is possible to increase the molecular weight (dimerize) by combining the compounds with a divalent group to break the conjugation as the method to improve the thin film property.

Accordingly, the organic EL device of the present invention can be used extensively as the starting material for various displaying.

Further, the styryl compound of the present invention is a novel compound having a structure wherein two structural units having EL luminescence are combined interposing a divalent group which breaks conjugation, and has a sufficient EL luminescent property and is excellent in thin film forming property, thin film retaining property, and heat resistant thin film property.

Consequently, the styryl compound of the present invention is expected to be used as the luminescent material for EL device, and as various luminescent material including fluorescent material.

The process of the present invention has a practical availability as the process for efficiently producing the above-mentioned styryl compound.

We claim:

1. In an organic electroluminescence device, which comprises a light emitting layer, the improvement comprising said light emitting layer comprising a dimerized styryl compound of the formula (a):

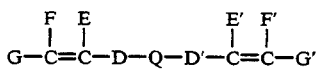

wherein D and D' are the same or different from each other and are each an arylene group having 6 to 20 carbon atoms or a divalent aromatic heterocyclic group having 3 to 20 carbon atoms, which are unsubstituted or are mono-substituted or poly-substituted with substituents (a'), E, E', F, F', G and G' are the same or different from each other and are each a hydrogen atom, or an aryl group having 6 to 20 carbon atoms, a cyclohexyl group, an alkyl group having 1 to 10 carbon atoms, an aralkyl group having 7 to 20 carbon atoms, an alkoxyl group having 1 to 10 carbon atoms, which are unsubstituted or are mono-substituted or poly-substituted with substituents (a'), or a monovalent aromatic heterocyclic group having 3 to 20 carbon atoms which is unsubstituted or mono-substituted or poly-substituted with substituents (a'), with the proviso that F and G are not both hydrogen atoms, and F' and G' are not both hydrogen atoms;

the substituents (a') are an alkyl group having 1 to 6 carbon atoms, an alkoxy group having 1 to 6 carbon atoms, an acyl group having 1 to 6 carbon atoms, an aralkyl group having 7 to 8 carbon atoms, an aryloxy group having 6 to 20 carbon atoms, an alkoxy-carbonyl group having 2 to 7 carbon atoms, an aryloxy-carbonyl group having 7 to 21 carbon atoms, an acyloxy group having 1 to 6 carbon atoms, an acylamino group having 1 to 6 carbon atoms, halogen atoms, a carboxyl group, an amino-carbonyl group, a hydroxyl group, a cyano group, a nitro group, or an amino group;

E and D, or E'and D' may combine with each other to form a saturated or unsaturated five-membered or six-membered ring, F and G, or F' and G' may combine with each other to form a saturated or unsaturated five-membered or six-membered ring; and Q is a divalent group to break the conjunction.

2. In an organic electroluminescence device, which comprises a light emitting layer, the improvement comprising said light emitting layer comprising a dimerized styryl compound of the formula (b):

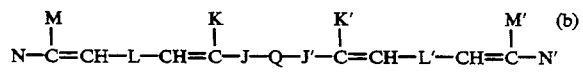

wherein J, J', L and L' are the same or different from each other and are each an arylene group having 6 to 20 carbon atoms or a divalent aromatic heterocyclic group having 3 to 20 carbon atoms, which are unsubstituted or mono-substituted or poly-substituted with substituents (a');

K, K', M, M', N and N' are the same or different from each other and are each a hydrogen atom, or an aryl group having 6 to 20 carbon atoms, a cyclohexyl group, an alkyl group having 1 to 10 carbon atoms, an aralkyl group having 7 to 20 carbon atoms, an alkoxyl group having 1 to 10 carbon atoms or a monovalent aromatic heterocyclic group having 3 to 20 carbon atoms, which are unsubstituted or mono-substituted or poly-substituted with substituents (a'), with the proviso that M and N are not both hydrogen atoms, and M' and N' are not both hydrogen atoms;

the substituents (a') are an alkyl group having 1 to 6 carbon atoms, an alkoxyl group having 1 to 6 carbon atoms, an acyl group having 1 to 6 carbon atoms, an aralkyl group having 7 to 8 carbon atoms, an aryloxy group having 6 to 20 carbon atoms, an alkoxy-carbonyl group having 2 to 7 carbon atoms, an aryloxy-carbonyl group having 7 to 21 carbon atoms, an acyloxy group having 1 to 6 carbon atoms, an acylamino group having 1 to 6 carbon atoms, a halogen atom, a carboxyl group, an amino-carbonyl group, a hydroxyl group, a cyano group, a nitro group, or an amino group;

K and J, or K' and J' may combine with each other to form a saturated or unsaturated five-membered or six-membered ring; M and N, or M' and N' may combine with each other to form a saturated or unsaturated five-membered or six-membered ring; and Q is a divalent group to break the conjunction.

3. The organic electroluminescence device according to claim 1, which further comprises a pair of electrodes and wherein the emitting layer is sandwiched between the pair of electrodes.

4. In an organic electroluminescence device which comprises an emitting layer, the improvement which comprises said emitting layer comprising an oligomer compound containing a styryl compound of the formula (c):

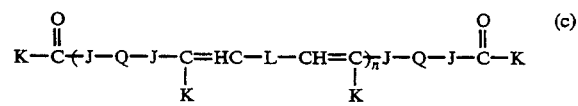

wherein J and L are the same or different from each other and are each an arylene group having 6 to 20 carbon atoms or a divalent aromatic heterocyclic group having 3 to 20 carbon atoms, which are unsubstituted or mono-substituted or poly-substituted with substituents (a'), K is a hydrogen atom or an aryl group having 6 to 20 carbon atoms, an alkyl group having 1 to 10 carbon atoms, an aralkyl group having 7 to 20 carbon atoms, an alkoxyl group having 1 to 10 carbon atoms or a monovalent aromatic heterocyclic group having 3 to 20carbon atoms, which are unsubstituted or mono-substituted or poly-substituted with substituents (a'), the substituents (a') are an alkyl group having 1 to 6 carbon atoms, an alkoxyl group having 1 to 6 carbon atoms, an acyl group having 1 to6 carbon atoms, an aralkyl group having 7 to 8 carbon atoms, an aryloxy group having 6 to 20 carbon atoms, an alkoxy-carbonyl group having 2 to 7 carbon atoms, an aryloxy-carbonyl group having 7 to 21 carbon atoms, an acyloxy group having 1 to 6 carbon atoms, an acylamino group having 1 to 6 carbon atoms, a halogen atom, a carboxyl group, an amino-carbonyl group, a hydroxyl group, a cyano group, a nitro group, or an amino group; Q is a divalent group to break the conjugation; and n is 1 to 5.

5. A dimerized styryl compound of the formula (a):

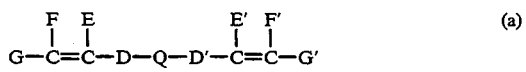

wherein
- D and D' are the same or different from each other and are each an arylene group having 6 to 20 carbon atoms or a divalent aromatic heterocyclic group having 3 to 20 carbon atoms, which are unsubstituted or are mono-substituted or poly-substituted with substituents (a'),
- E, E', G and G' are the same or different from each other and are each a hydrogen atom, or an aryl group having 6 to 20 carbon atoms, a cyclohexyl group, an alkyl group having 1 to 10 carbon atoms, an aralkyl group having 7 to 20 carbon atoms, an alkoxyl group having 1 to 10 carbon atoms or a monovalent aromatic heterocyclic group having 3 to 20 carbon atoms, which are unsubstituted or mono-substituted or poly-substituted with substituent (a');
- F and F' are the same or different from each other and are each an aryl group having 6 to 20 carbon atoms, cyclohexyl group, an aralkyl group having 7 to 20 carbon atoms, an alkoxyl group having 1 to 10 carbon atoms or a monovalent aromatic heterocyclic group having 3 to 20 carbon atoms, which are unsubstituted or mono-substituted or poly-substituted with substituents (a');
- the substituents (a') are an alkyl group having 1 to 6 carbon atoms, an alkoxyl group; having 1 to 6 carbon atoms, an acyl group having 1 to 6 carbon atoms, an aralkyl group having 7 to 8 carbon atoms, an aryloxy group having 6 to 20 carbon atoms, an alkoxy-carbonyl group having 2 to 7 carbon atoms, an aryloxy-carbonyl group having 7 to 21 carbon atoms, an acyloxy group having 1 to 6 carbon atoms, an acylamino group having 1 to 6 carbon atoms, a halogen atom, a carboxyl group, an amino-carbonyl group, a hydroxyl group, a cyano group, a nitro group, or an amino group;
- E and D, or E' and D' may combine with each other to form a saturated or unsaturated five-membered or six-membered ring, F and G, or F' and G' may combine with each other to form a saturated or unsaturated five-membered or six-membered ring; and
- Q is a divalent group to break the conjunction.

6. A dimerized styryl compound of the formula (b):

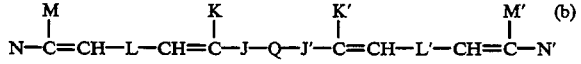

wherein J, J', L and L' are the same or different from each other and are each an arylene group having 6 to 20 carbon atoms or a divalent aromatic heterocyclic group having 3 to 20 carbon atoms, which are unsubstituted or mono-substituted or poly-substituted with substituents (a');
K, K', M, M', N and N' are the same or different from each other and are each a hydrogen atom, or an aryl group having 6 to 20 carbon atoms, a cyclohexyl group, an alkyl group having 1 to 10 carbon atoms, or a monovalent aromatic heterocyclic group having 3 to 20 carbon atoms, which are unsubstituted or mono-substituted or poly-substituted with substituents (a'), with the proviso M and N are not both hydrogen atoms, and M' and N' are not both hydrogen atoms;
the substituents (a') are an alkyl group having 1 to 6 carbon atoms, an alkoxyl group having 1 to 6 carbon atoms, an acyl group having 1 to 6 carbon atoms, an aralkyl group having 7 to 8 carbon atoms, an aryloxy group having 6 to 20 carbon atoms, an alkoxy-carbonyl group having 2 to 7 carbon atoms, an aryloxy-carbonyl group having 7 to 21 carbon atoms, an acyloxy group having 1 to 6 carbon atoms, an acylamino group having 1 to 6 carbon atoms, a halogen atom, a carboxyl group, an amino-carbonyl group, a hydroxyl group, a cyano group, a nitro group, or an amino group;
K and J, or K' and J' may combine with each other to form a saturated or unsaturated five-membered or six-membered ring; M and N, or M' and N' may combine with each other to form a saturated or unsaturated five-membered or six-membered ring; and
Q is a divalent group to break the conjunction.

7. The dimerized compound according to claim 5 which has the formula (d):

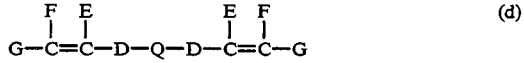

wherein D is an arylene group having 6 to 20 carbon atoms or a divalent aromatic heterocyclic group having 3 to 20 carbon atoms, which are unsubstituted or mono-substituted or poly-substituted by substituents (a'),
E and G are the same or different from each other and are each a hydrogen atom, or an aryl group having 6 to 20 carbon atoms, a cyclohexyl group, an alkyl group having 1 to 10 carbon atoms, an aralkyl group having 7 to 20 carbon atoms, an alkoxyl group having 1 to 10 carbon atoms or a monovalent aromatic group, which are unsubstituted, mono-substituted or poly-substituted by substituents (a'),
F is an aryl group having 6 to 20 carbon atoms, a cyclohexyl group, an aralkyl group having 7 to 20 carbon atoms, an alkoxyl group having 1 to 10 carbon atoms or a monovalent aromatic heterocyclic group having 3 to 20 carbon atoms, which are unsubstituted or mono-substituted or poly-substituted with substituents (a');
the substituents (a') are an alkyl group having 1 to 6 carbon atoms, an alkoxyl group having 1 to 6 carbon atoms, an acyl group having 1 to 6 carbon atoms, an aralkyl group having 7 to 8 carbon atoms, an aryloxy group having 6 to 20 carbon atoms, an alkoxy-carbonyl group having 2 to 7 carbon atoms, an aryloxy-carbonyl group having 7 to 21 carbon atoms, an acyloxy group having 1 to 6 carbon atoms, an acylamino group having 1 to 6 carbon atoms, a halogen atom, a carboxyl group, an amino-carbonyl group, a hydroxyl group, a cyano group, a nitro group, or an amino group;
Q is a divalent group to break the conjugation.

8. The dimerized compound according to claim 6 which has the formula (e):

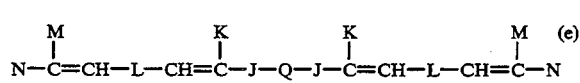

wherein J and L are the same or different from each other and are an arylene group having 6 to 20 carbon atoms or a divalent aromatic heterocyclic group having 3 to 20 carbon atoms, which are unsubstituted or mono-substituted or poly-substituted with substituents (a'), K is a hydrogen atom, or an aryl group having 6 to 20 carbon atoms, an alkyl group having 1 to 10 carbon atoms, an aralkyl group having 7 to 20 carbon atoms, an alkoxyl group having 1 to 10 carbon atoms or a monovalent aromatic heterocyclic group having 3 to 20 carbon atoms, which are unsubstituted or mono-substituted or poly-substituted with substituents (a'), M and N are the same or different from each other and are each a hydrogen atom, or an aryl group having 6 to 20 carbon atoms, a cyclohexyl group, an alkyl group having 1 to 10 carbon atoms, an aralkyl group having 7 to 20 carbon atoms, an alkoxyl group having 1 to 10 carbon atoms or a monovalent aromatic heterocyclic group having 3 to 20 carbon atoms, which are unsubstituted or mono-substituted by substituents (a') or poly-substituted by substituents (a'), the substituents (a') are an alkyl group having 1 to 6 carbon atoms, an alkoxyl group having 1 to 6 carbon atoms, an acyl group having 1 to 6 carbon atoms, an aralkyl group having 7 to 8 carbon atoms, an aryloxy group having 6 to 20 carbon atoms, an alkoxy-carbonyl group having 2 to 7 carbon atoms, an aryloxy-carbonyl group having 7 to 21 carbon atoms, an acyloxy group having 1 to 6 carbon atoms, an acylamino group having 1 to 6 carbon atoms, a halogen atom, a carboxyl group, an amino-carbonyl group, a hydroxyl group, a cyano group, a nitro group, or an amino group; and Q is a divalent group to break the conjugation.

9. An oligomer compound of the formula (c):

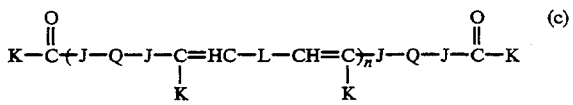

wherein J and L are the same or different and each other and are an arylene group having 6 to 20 carbon atoms or a divalent aromatic heterocyclic group having 3 to 20 carbon atoms, which are unsubstituted or mono-substituted or poly-substituted with substituents (a'), K is a hydrogen atom, or an aryl group having 6 to 20 carbon atoms, an alkyl group having 1 to 10 carbon atoms, an aralkyl group having 7 to 20 carbon atoms, an alkoxyl group having 1 to 10 carbon atoms, or a monovalent aromatic heterocyclic group having 3 to 20 carbon atoms which are unsubstituted or mono-substituted or poly-substituted with substituents (a'), M and N are the same or different from each other and are each a hydrogen atom, or an aryl group having 6 to 20 carbon atoms, a cyclohexyl group, an alkyl group having 1 to 10 carbon atoms, an aralkyl group having 7 to 20 carbon atoms, an alkoxyl group having 1 to 10 carbon atoms or a monovalent aromatic heterocyclic group having 3 to 20 carbon atoms, which are unsubstituted or mono-substituted by substituents (a') or poly-substituted by substituents (a'), the substituents (a') are an alkyl group having 1 to 6 carbon atoms, an alkoxyl group having 1 to 6 carbon atoms, an acyl group having 1 to 6 carbon atoms, an aralkyl group having 7 to 8 carbon atoms, an aryloxy group having 6 to 20 carbon atoms, an alkoxy-carbonyl group having 2 to 7 carbon atoms, an aryloxy-carbonyl group having 7 to 21 carbon atoms, an acyloxy group having 1 to 6 carbon atoms, an acylamino group having 1 to 6 carbon atoms, a halogen atom, a carboxyl group an amino-carbonyl group, a hydroxyl group, a cyano group, a nitro group, or an amino group; and Q is a divalent group to break the conjugation and wherein n is 1 to 5.

10. In an organic electroluminescence device which comprises a light emitting layer, the improvement comprising said light emitting layer comprising the dimerized styryl compound of the formula (d) according to claim 7.

11. In an organic electroluminescence device which comprises a light emitting layer, the improvement comprising said light emitting layer comprising the dimerized styryl compound of the formula (e) according to claim 8.

12. The organic electroluminescence device according to claim 2, which further comprises a pair of electrodes and wherein the emitting layer is sandwiched between the pair of electrodes.

13. The organic electroluminescence device according to claim 1, which further comprises a cathode, an anode and one of a hole injection transportation layer or an electron injection layer.

14. The organic electroluminescence device according to claim 2, which further comprises a cathode, an anode and one of a hole injection transportation layer or an electron injection layer.

15. The organic electroluminescence device according to claim 14, wherein the device is a laminate which contains in the following order: the cathode, the hole injection transportation layer, the emitting layer and the anode.

16. The organic electroluminescence device according to claim 14, wherein the device is a laminate which contains in the following order: the cathode, the hole injection transportation layer, the emitting layer, the electron injecting layer and the anode.

17. The organic electroluminescence device according to claim 14, wherein the device is a laminate which contains in the following order: the cathode, the emitting layer, the electron injection layer and the anode.

18. The organic electroluminescence device according to claim 1, wherein the mono-substituents are selected from the group consisting of an alkyl group having 1 to 6 carbon atoms, an aryloxy group having 6 to 20 carbon atoms, an amino group and a phenyl group, which are unsubstituted or substituted by a substituent (a') and the poly-substituents are selected from the group consisting of an alkyl group having 1 to 6 carbon atoms, an alkoxyl group having 1 to 10 carbon atoms, an aryloxy group having 6 to 20 carbon atoms, an amino group and a phenyl group, which are unsubstituted or substituted by a substituent (a').

19. The organic electroluminescence device according to claim 2, wherein the mono-substituents are selected from the group consisting of an alkyl group having 1 to 6 carbon atoms, an aryloxy group having 6 to 20 carbon atoms, an amino group and a phenyl group, which are unsubstituted or substituted by a substituent (a') and the poly-substituents are selected from the group consisting of an alkyl group having 1 to 6 carbon atoms, an alkoxyl group having 1 to 10 carbon atoms, an aryloxy group having 6 to 20 carbon atoms, an amino group and a phenyl group, which are unsubstituted or substituted by a substituent (a').

20. The organic electroluminescence device according to claim 1, wherein Q is selected from the group consisting of

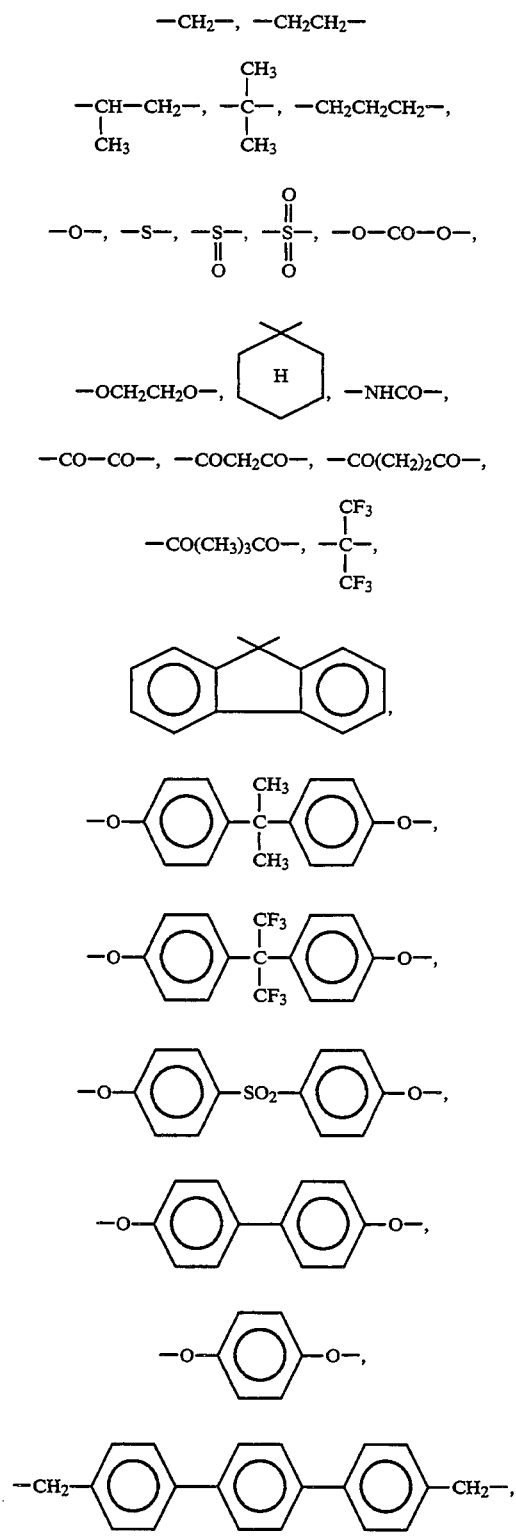

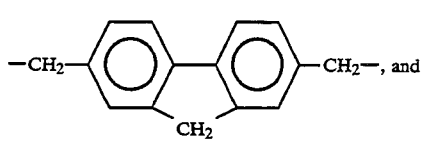

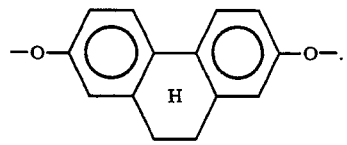

21. The organic electroluminescence device according to claim 2, wherein Q is selected from the group consisting of

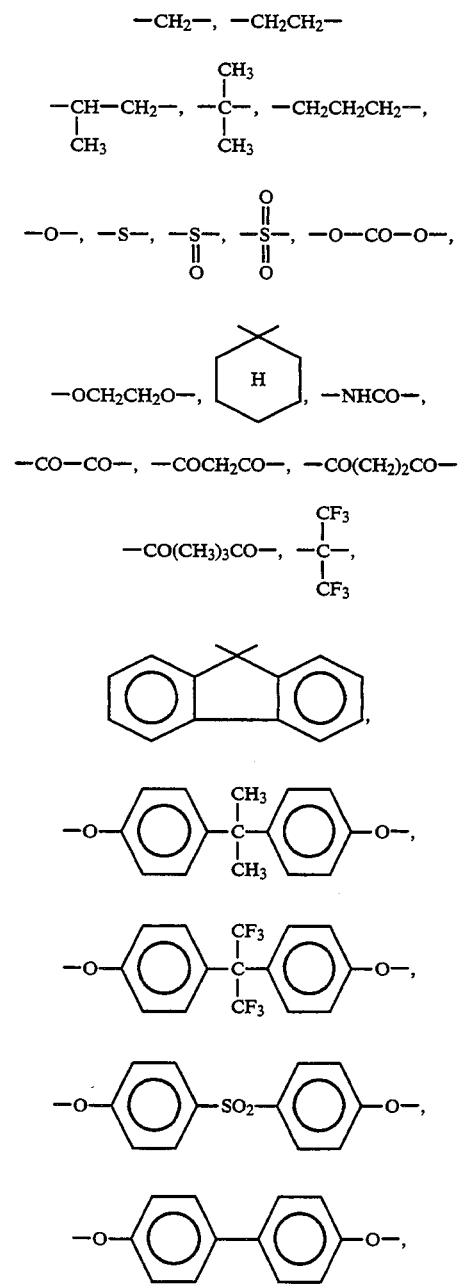

-continued

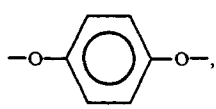

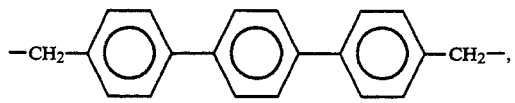

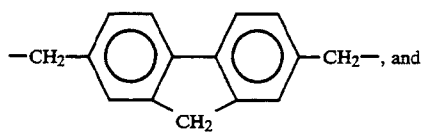

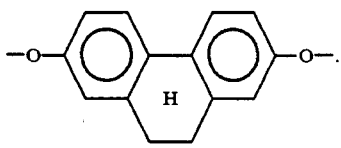

22. The organic electroluminescence device according to claim 20, wherein E, E, F, F' G and G' are the same or different from each other and each are a hydrogen atom, a phenyl group, a naphthyl group, an anthryl group, a biphenyl group, a terphenyl group, a pyrenyl group, a perylene group, a methyl group, an ethyl group, an isopropyl group, a t-butyl group, a benzyl group, a phenethyl group, a methoxyl group, an ethoxyl group, a propoxyl group, a butoxyl group, a furyl group, a thienyl group, a pyrrolyl group, a quinolyl group, a carbazolyl group, an N-alkylcarbazolyl group, a formyl group, an acetyl group, a propionyl group, a butylyl group, a phenoxy group, a tolyloxy group, a methoxycarbonyl group, an ethoxycarbonyl group, a propoxycarbonyl group, a butoxycarbonyl group, a phenoxycarbonyl group, a tolyloxycarbonyl group, a xylyloxycarbonyl group, an acetyloxy group, a propionyloxy group, a butylyloxy group, an acetylamino group, a propionylamino group, a butylamino group, a halogen atom, a carboxyl group, an anilinocarbonyl group, a carbamoyl group, a dimethylaminocarbonyl group or a triazole group and D and D' are the same or different from each other and are a phenylene group, a biphenylene group, a naphthylene group, a terphenylene group, an antharacenediyl group, a pyrenediyl group, a perylenediyl group, a thienylene group, a pyrrolylene group, a pyridylene group, a quinolylene group, a carbazolylene group and a N-alkylcarbazolylene group.

23. The organic electroluminescence device according to claim 21, wherein K, M and N, and K', M' and N' are the same or different from each other and are each a hydrogen atom, a phenyl group, a naphthyl group, an anthryl group, a biphenyl group, a terphenyl group, a pyrenyl group, a perylenyl group, a cyclohexyl group, a methyl group, an ethyl group, an isopropyl group, a t-butyl group, a methoxyl group, an ethoxyl group, a propoxyl group, a butoxyl group, a benzyl group, a phenethyl group, a furyl group, a thienyl group, a, pyrrolyl group, a pyridyl group, a quinolyl group, a carbazolyl group, an N-alkylcarbazolyl group, a formyl group, an acetyl group, la propionyl group, a butylyl group, a phenoxyl group, a tolyloxy group, a methoxycarbonyl group, an ethoxycarbonyl group, a propoxycarbonyl group, a butoxycarbonyl group, a phenoxycarbonyl group, a tolyloxycarbonyl group, a xylyloxycarbonyl group, an acetyloxy group, a propionyloxy group, a butylyloxy group, an acetylamino group, a propionylamino group, a butylylamino group, a halogen atom, a carboxyl group, an anilinocarbonyl group, a carbamoyl group, a dimethylaminocarbonyl group, a triazole group or a tolyl group; J and J', and L and L' are the same or different from each other and are each a phenylene group, a biphenylene group, a naphthylene group, a thienylene group, a pyrrolylene group, a pyridylene group, a quinolylene group or a carbazolylene group.

24. The organic electroluminescence device according to claim 4, wherein the oligomer compound containing a styryl compound is selected from the group consisting of

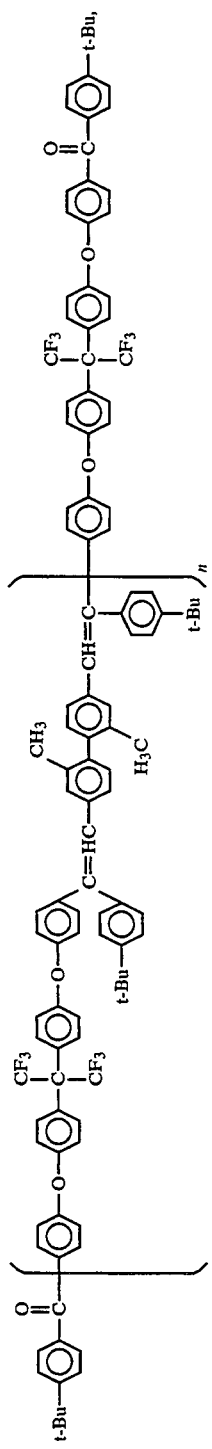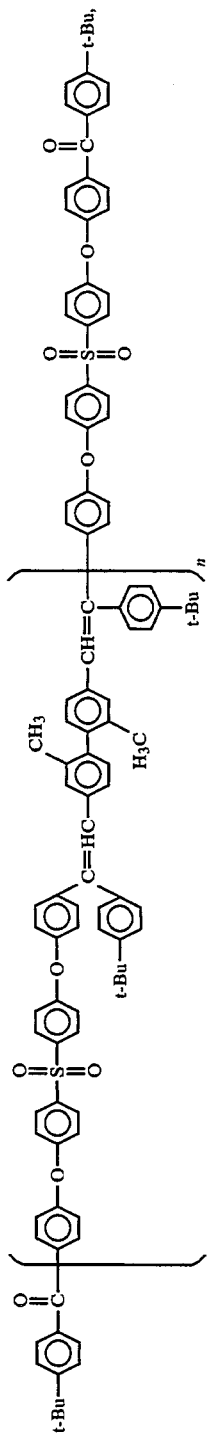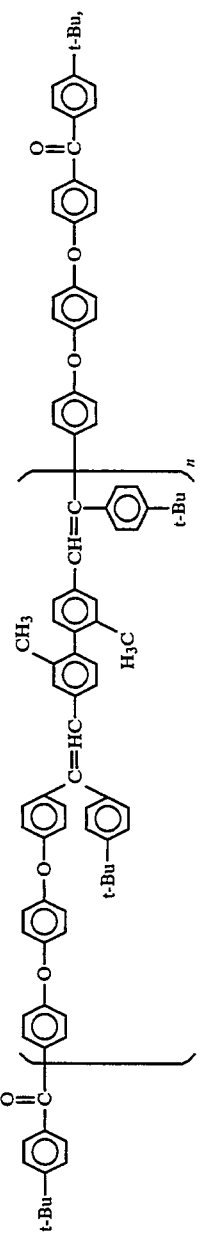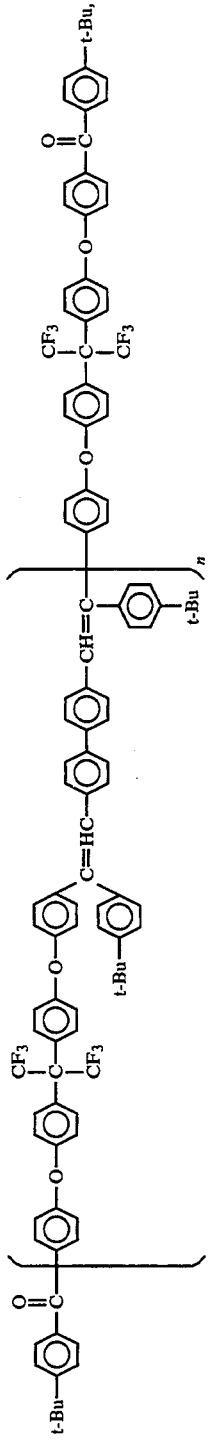

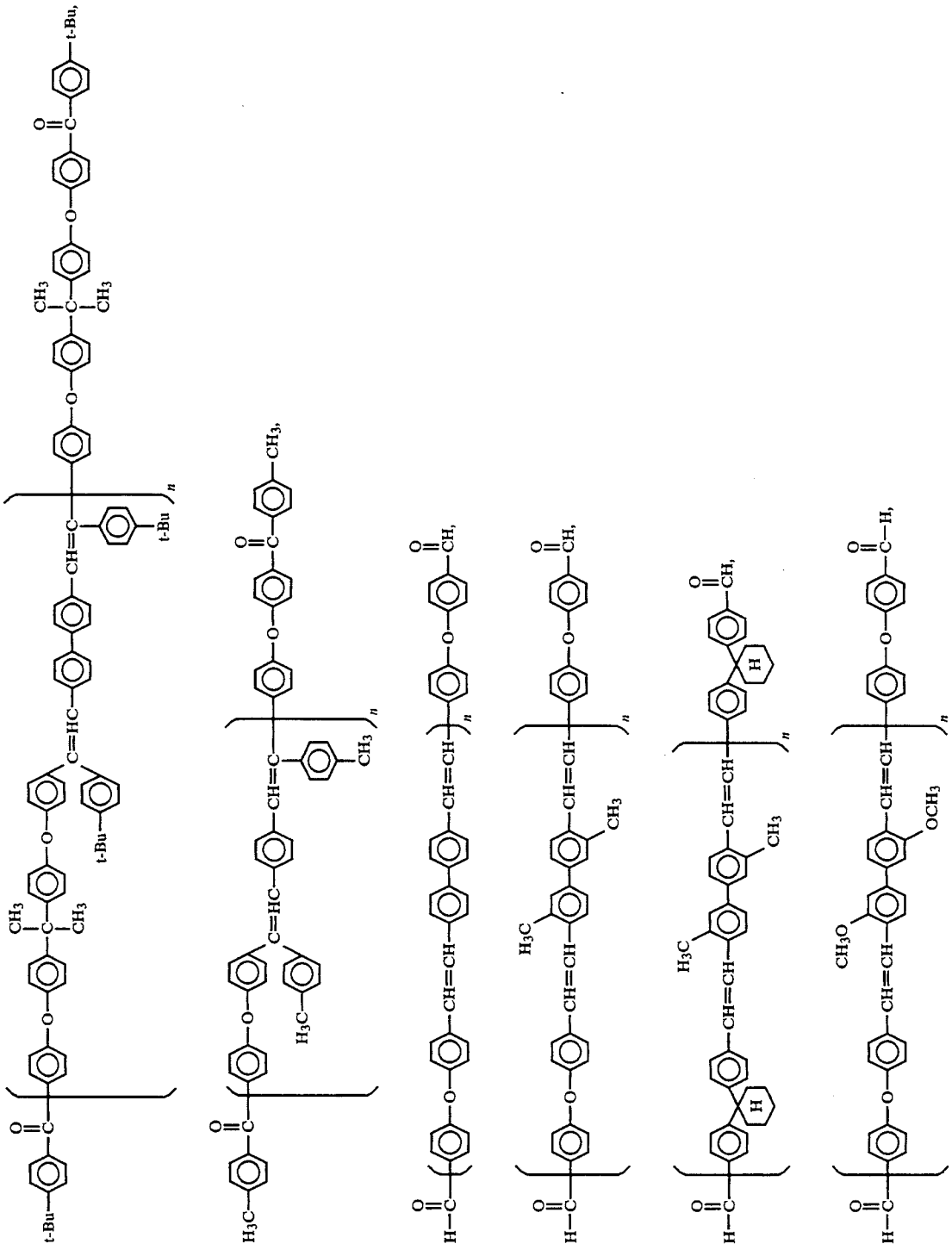

-continued
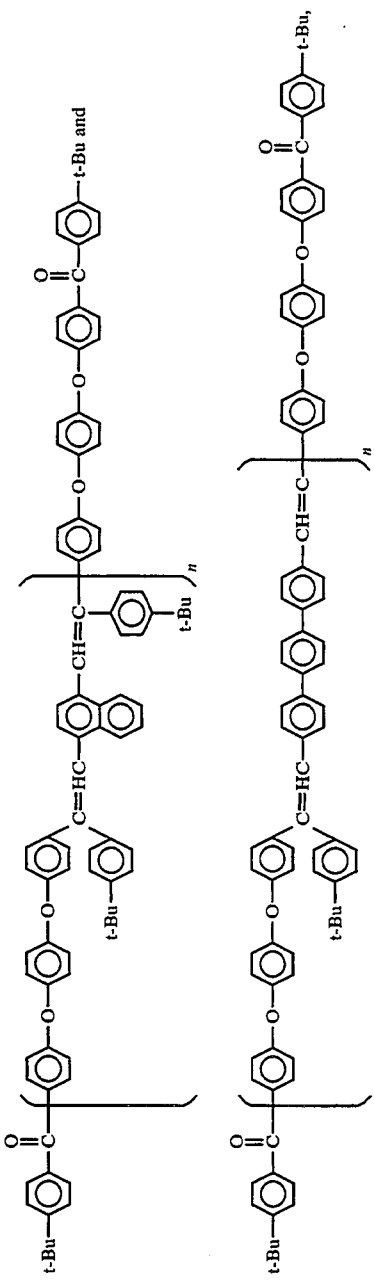

wherein t-Bu is tertiarybutyl,

25. An organic electroluminescence device comprising a light emitting layer disposed between a pair of electrodes, the light emitting layer comprising a dimerized styryl compound selected from the group consisting of (1) 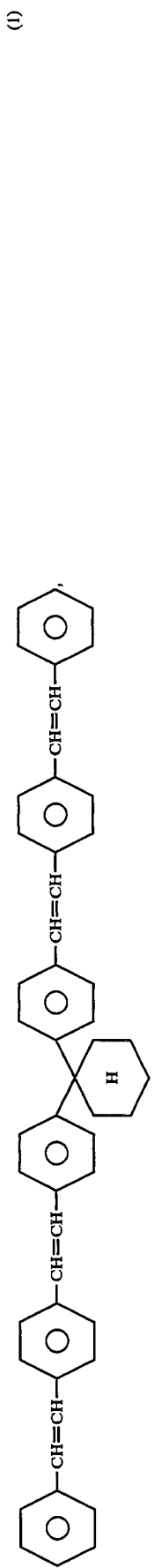
(2) 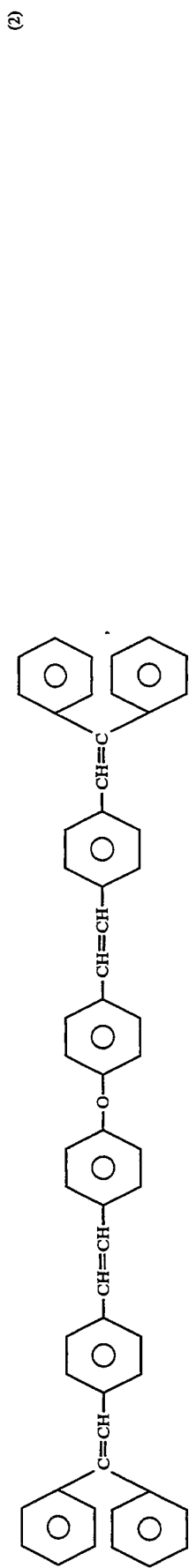
(3) 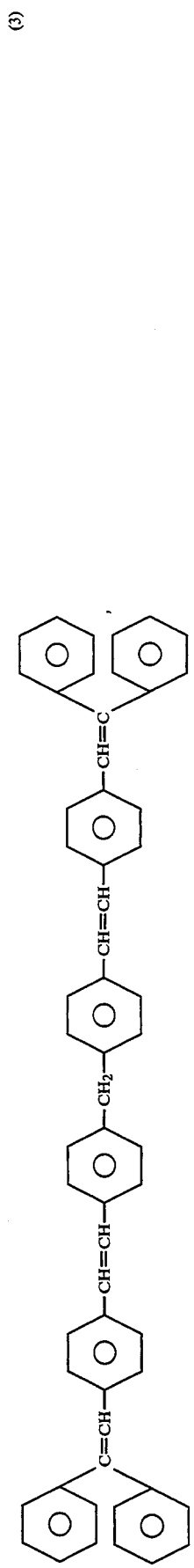
(4) 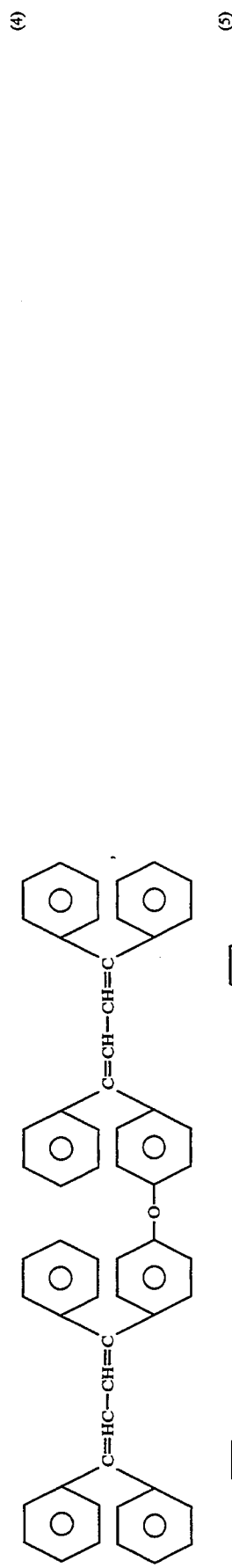
(5) 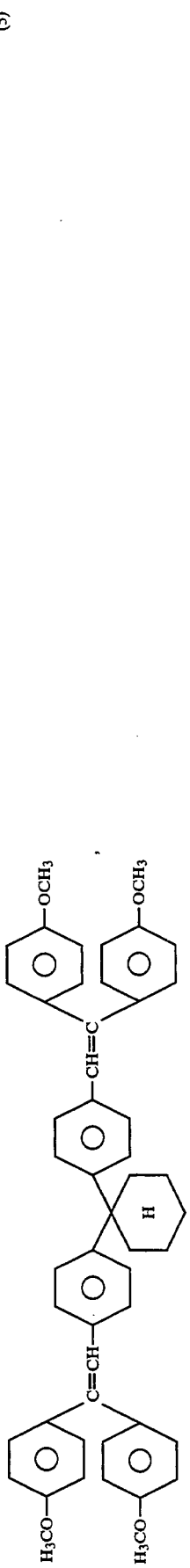

-continued
(6)
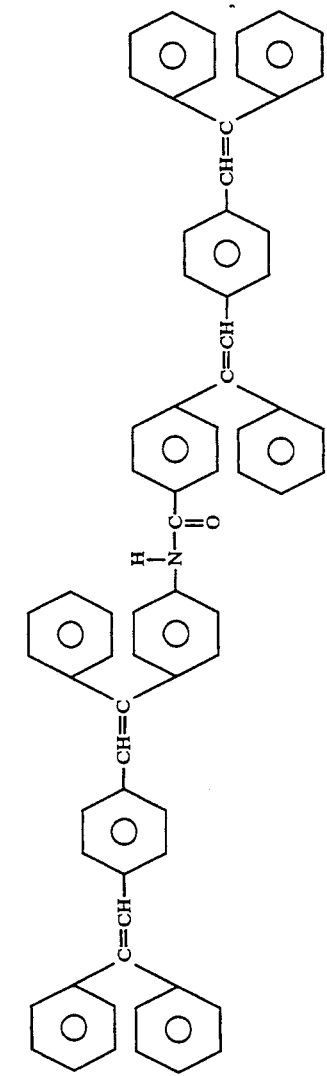
(7)
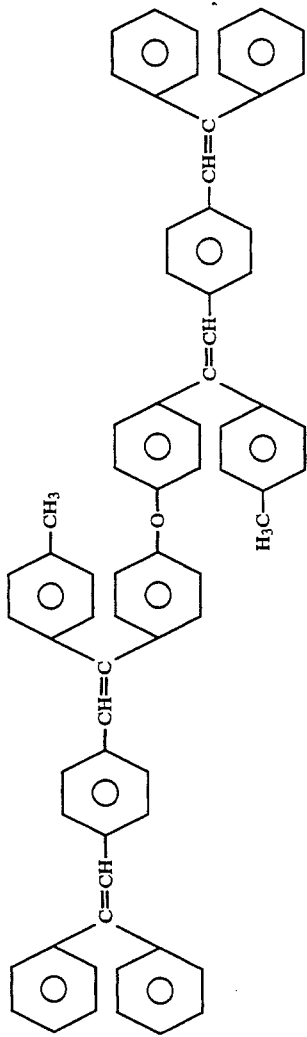
(8)
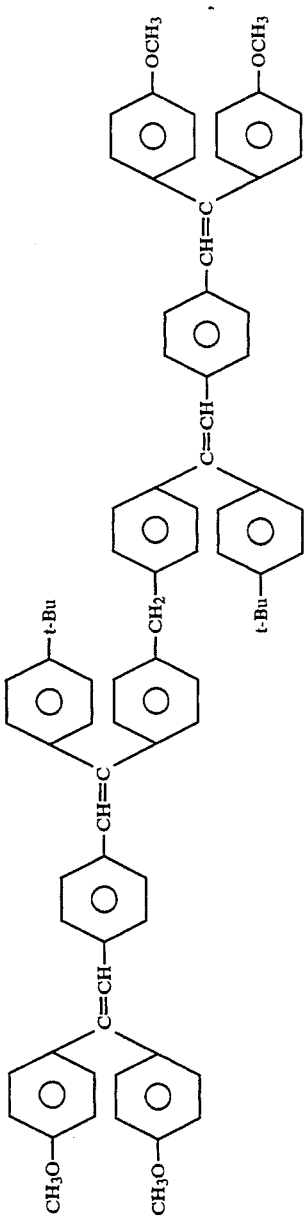

-continued
(9)
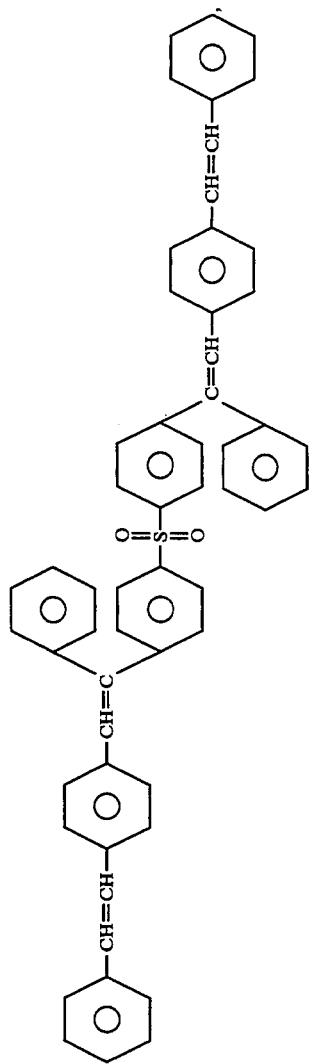
(10)
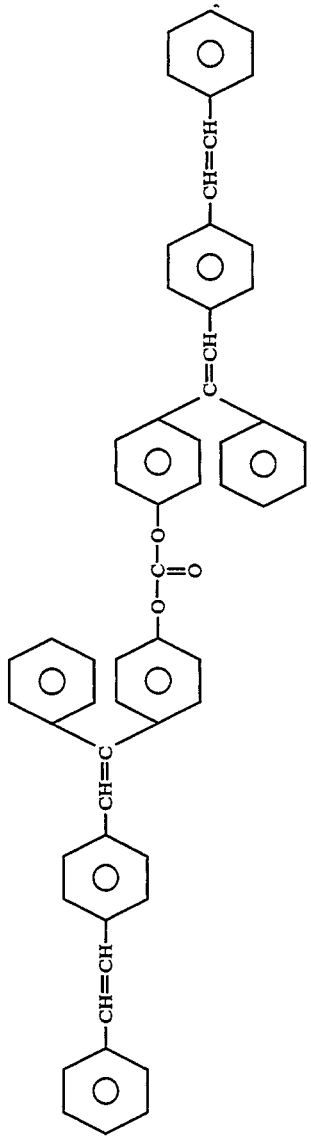
(11)
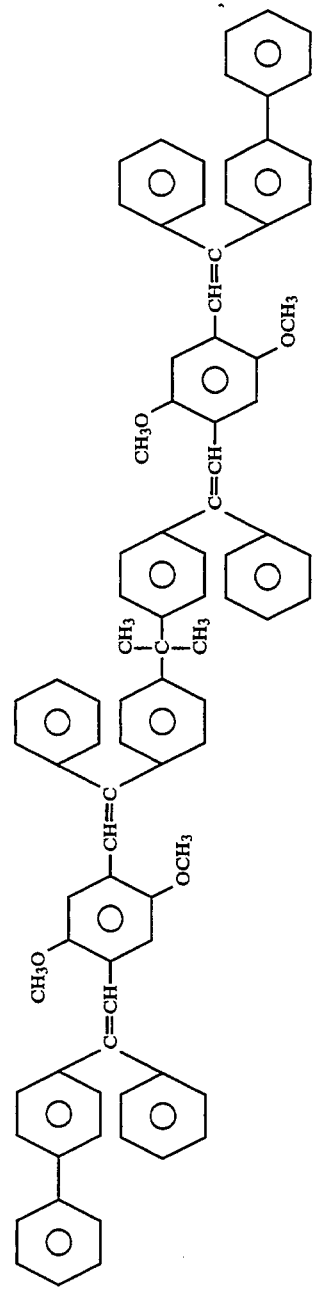

(12) 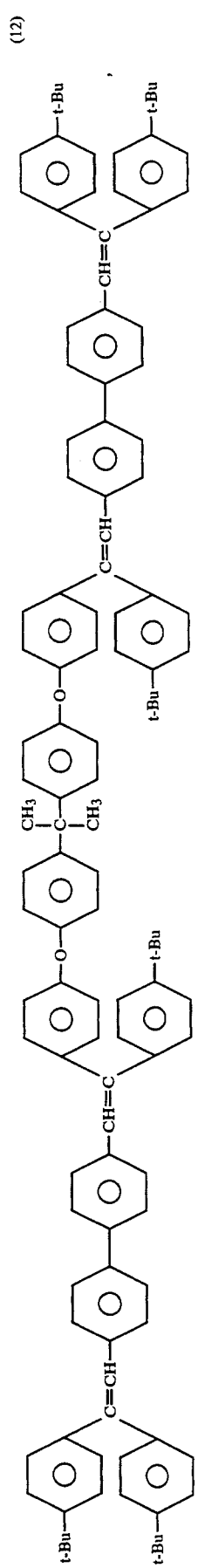
(13) 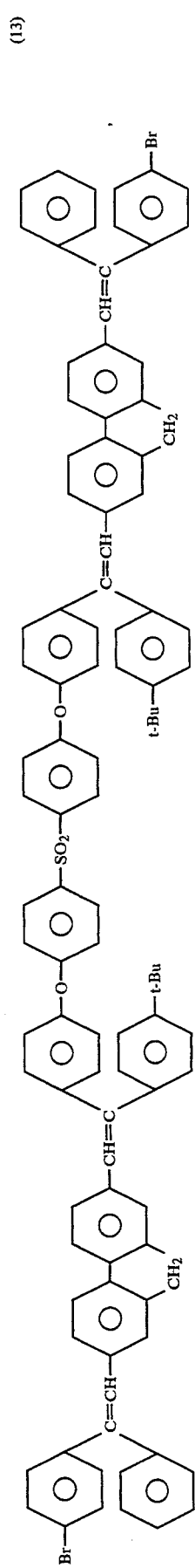
(14) 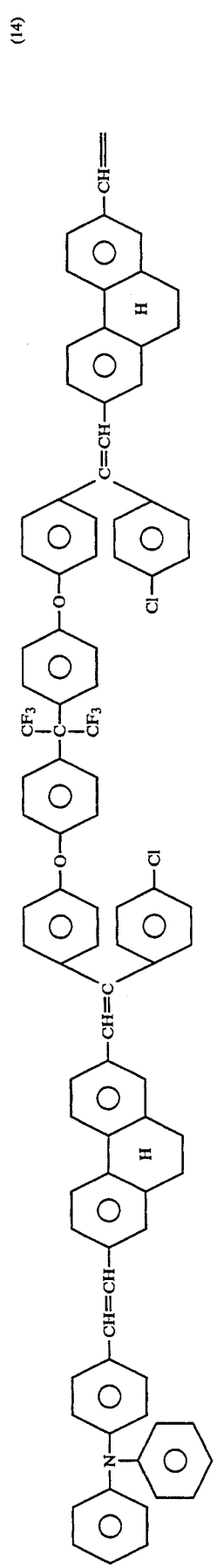
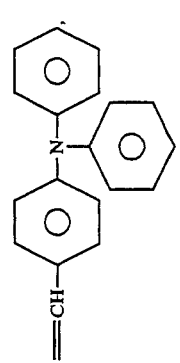

(15)
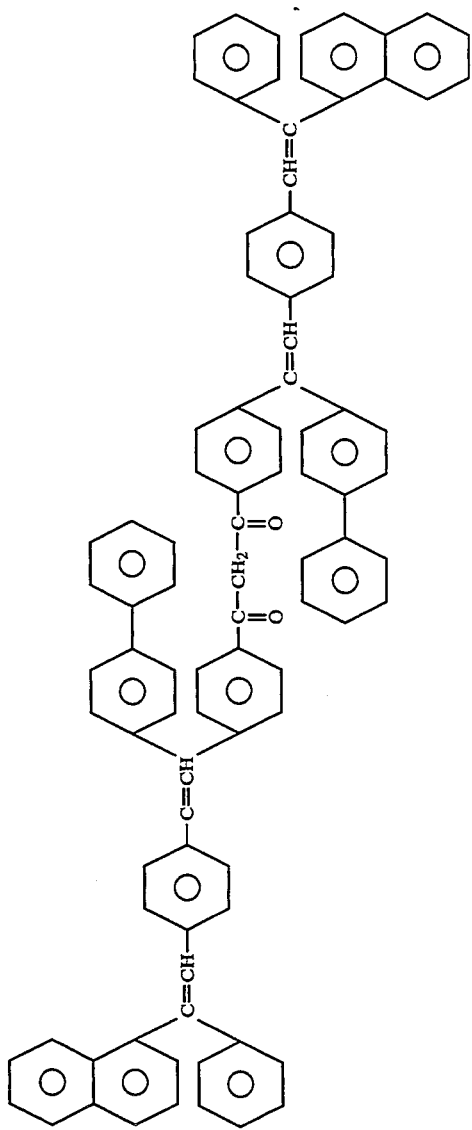
(16)
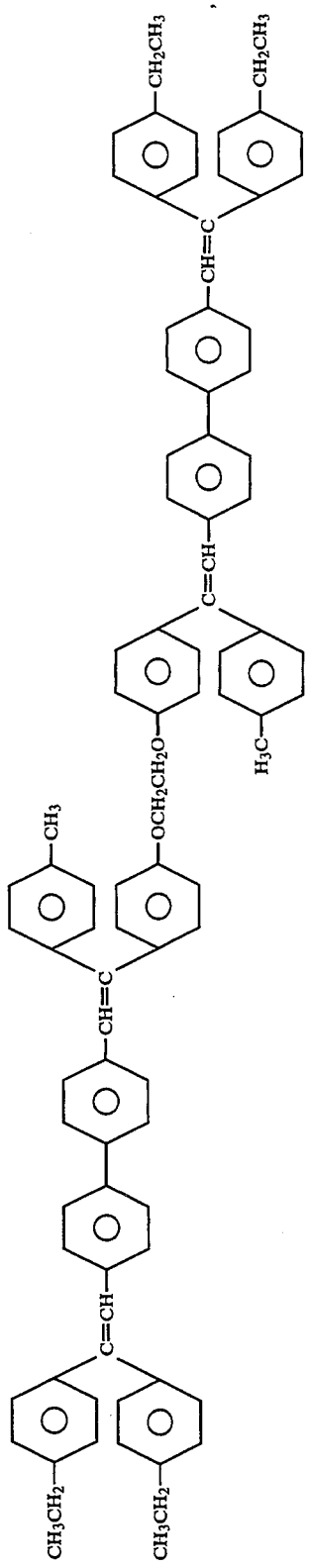
(17)
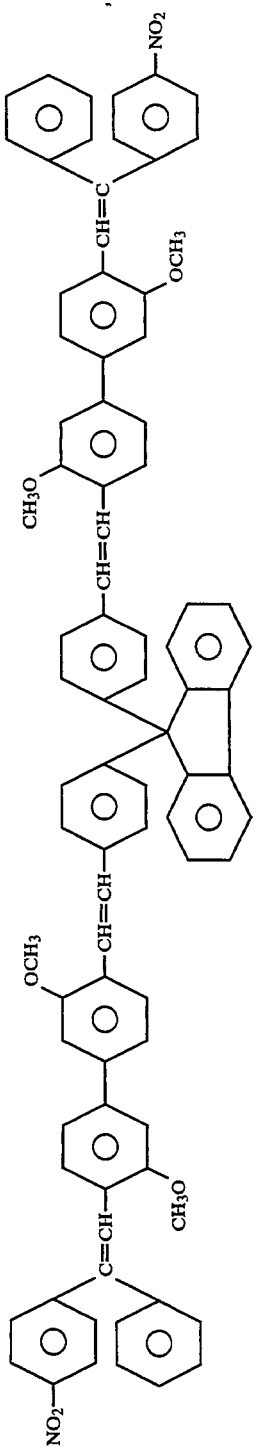

-continued
(18)
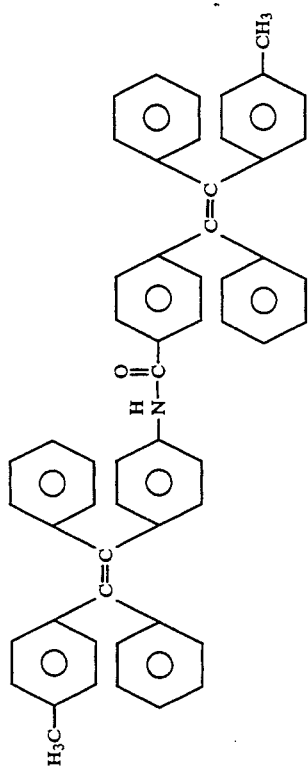
(19)
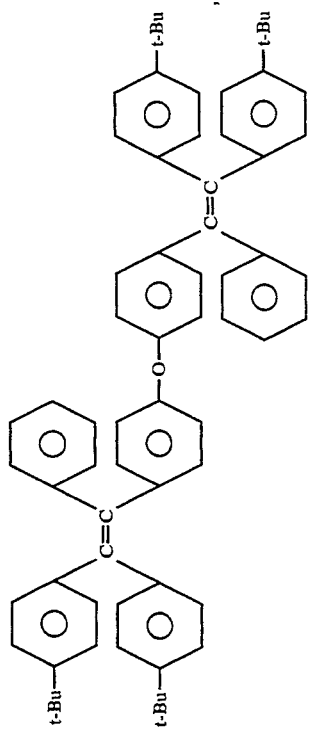
(20)
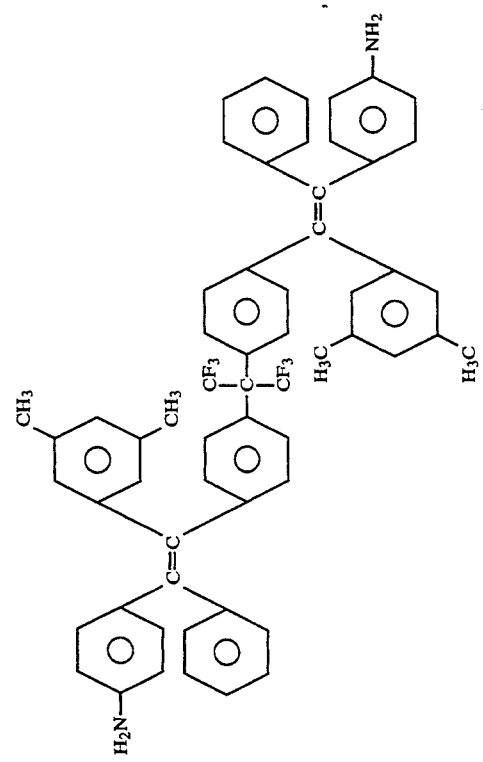

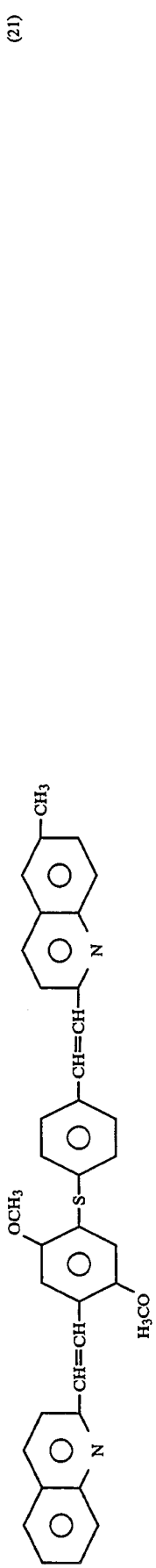

-continued
(26) 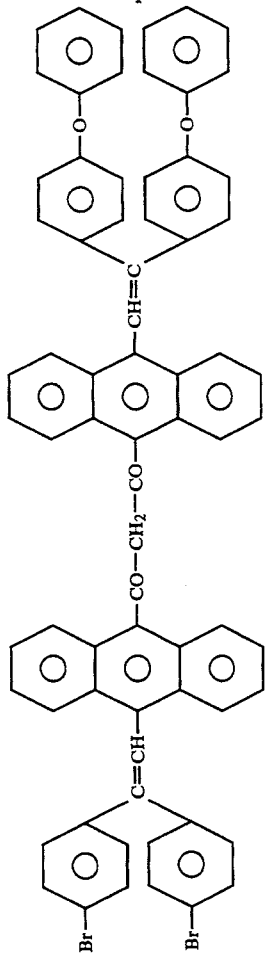
(27) 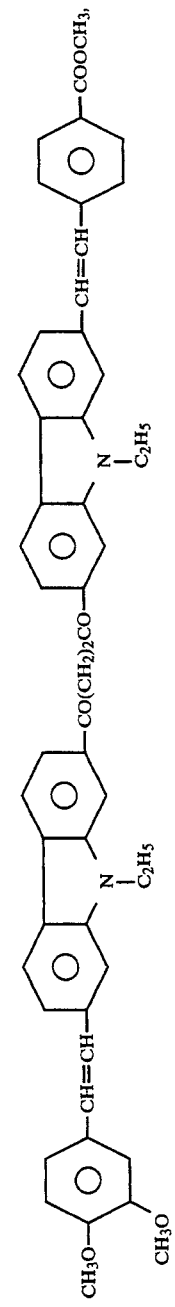
(28) 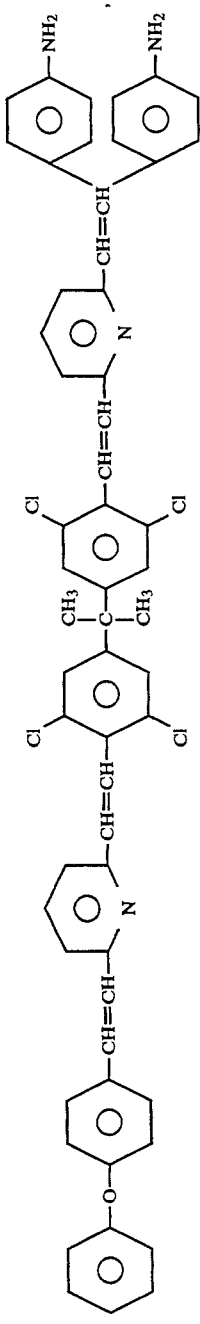
(29) 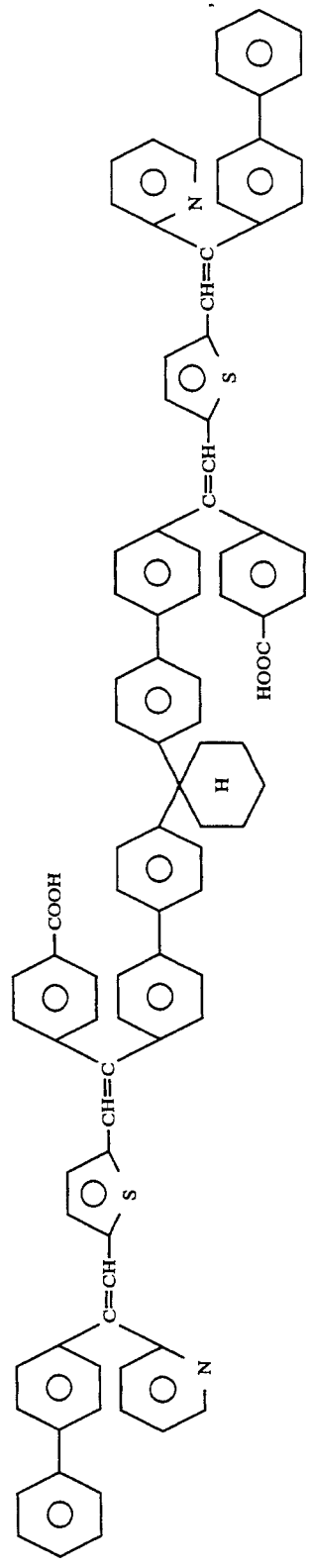

(30) (31) (32) (33)
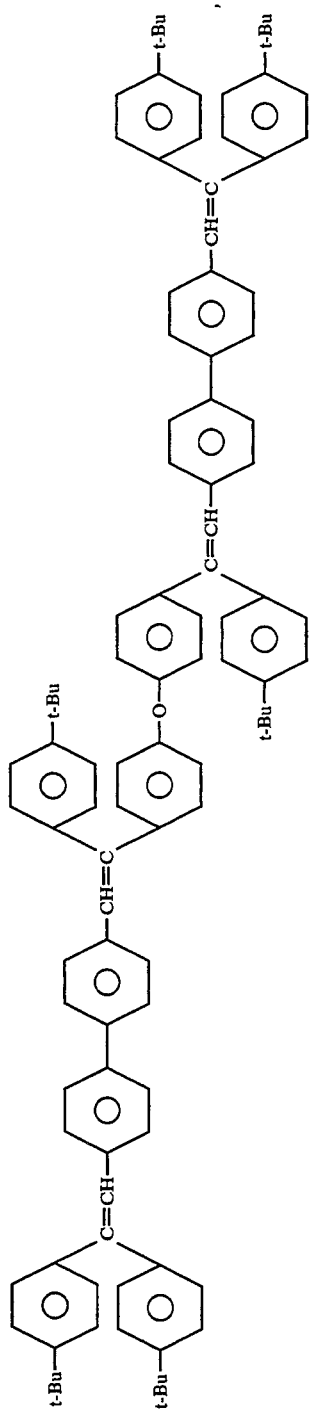
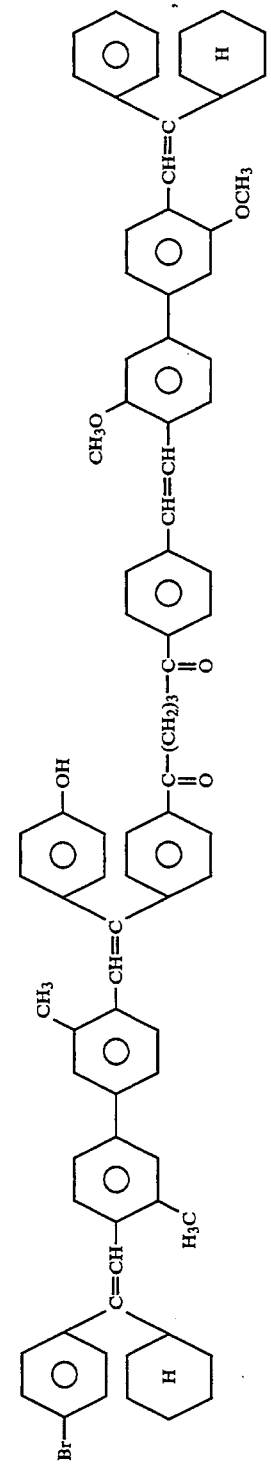
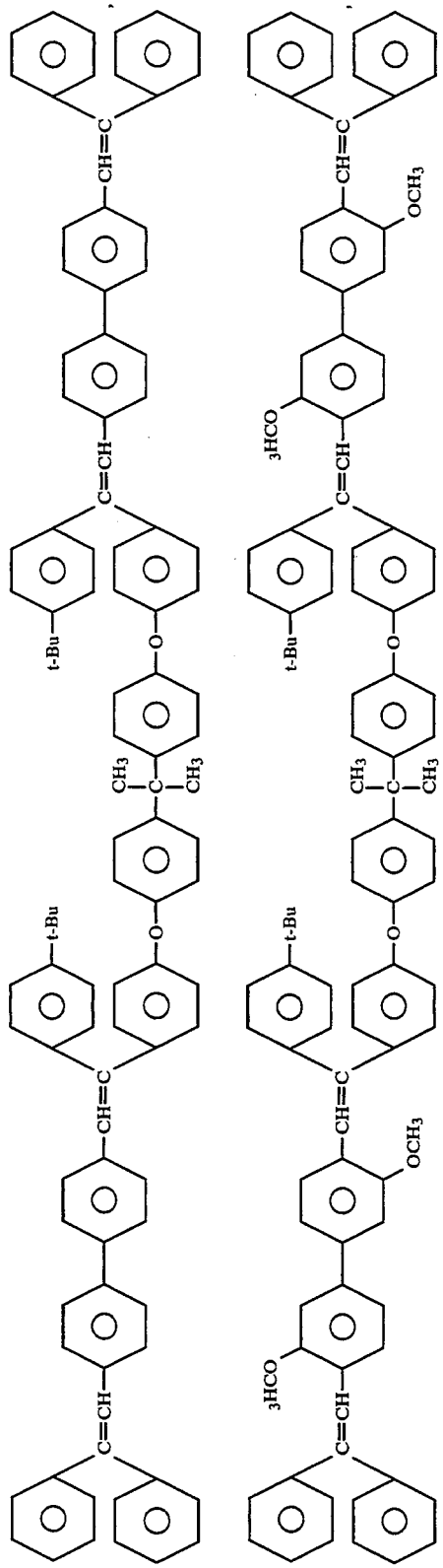
(t-Bu; tertiarybutyl)

-continued
(34) 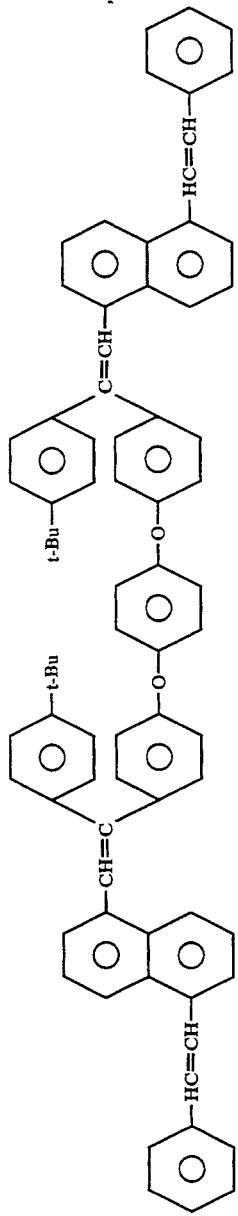
(35) 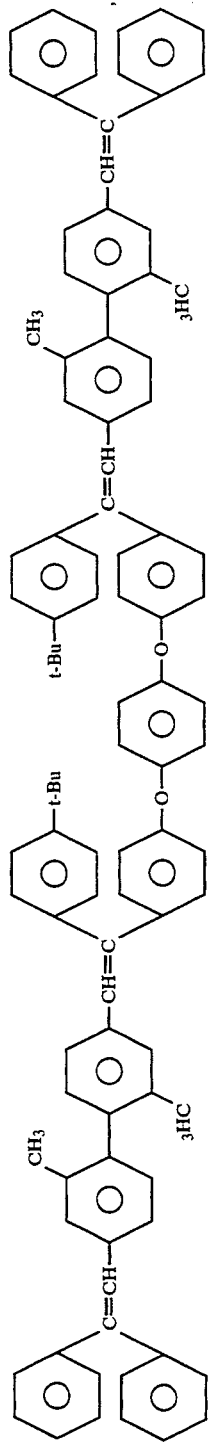
(36) 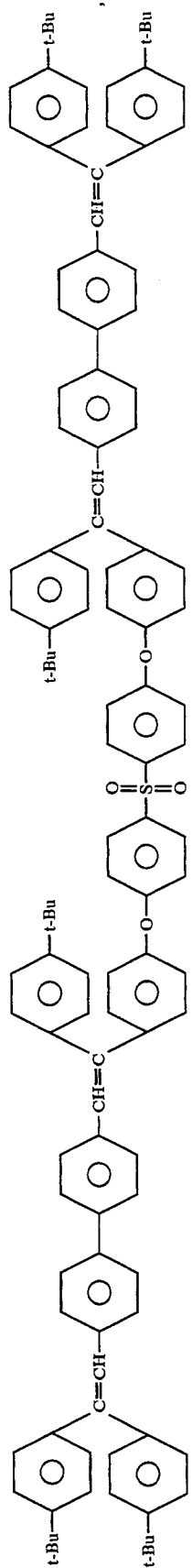
(37) 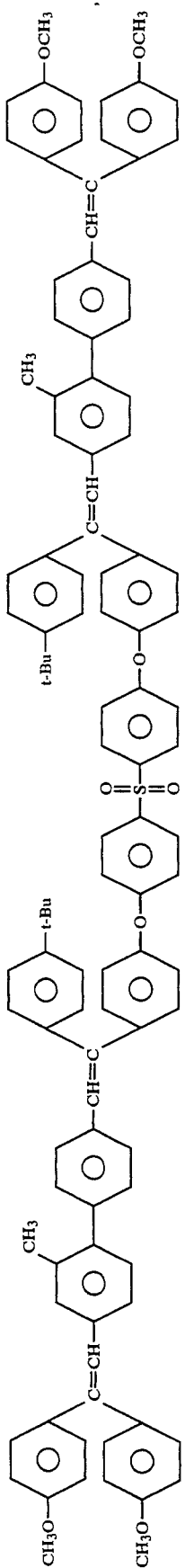

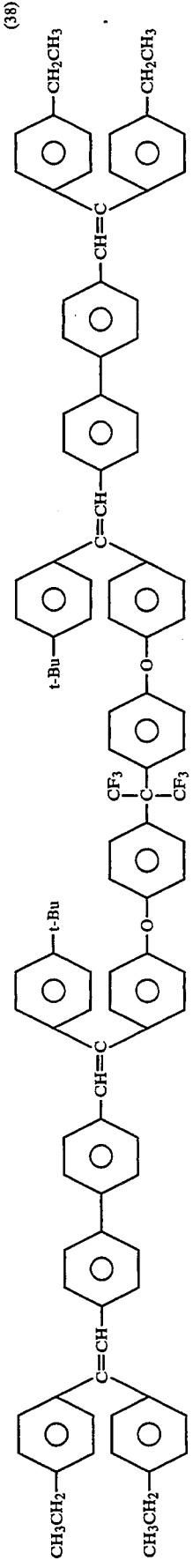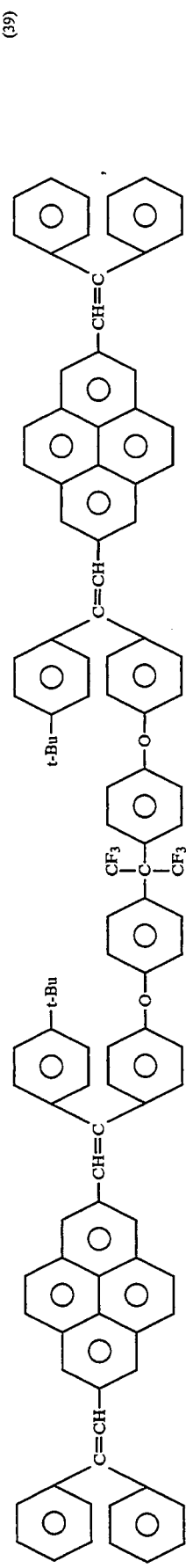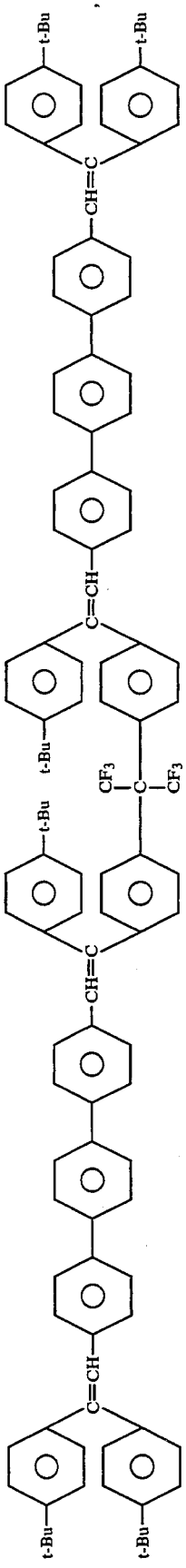

(41) (42) (43) (44)
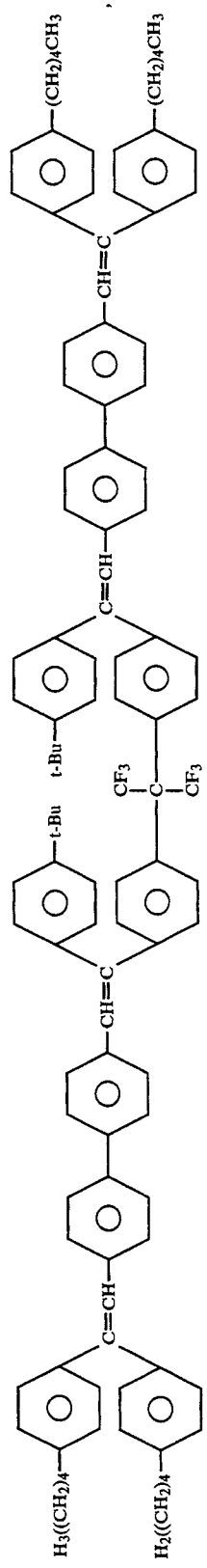
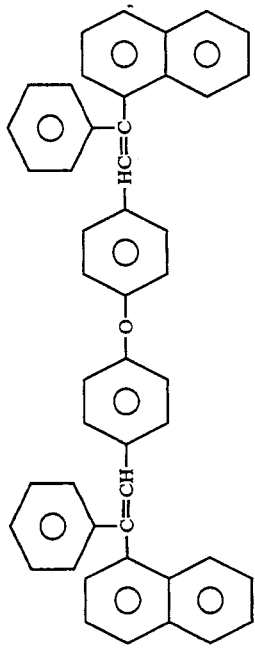
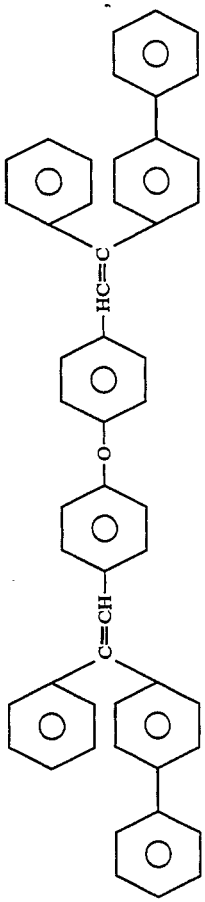
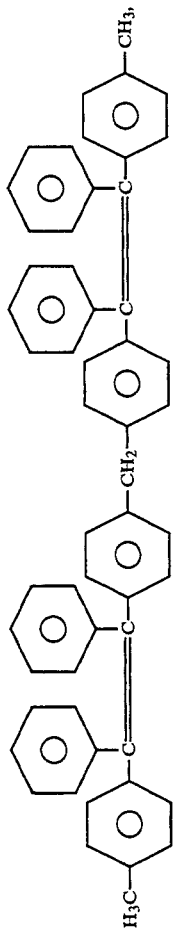

-continued
(45) 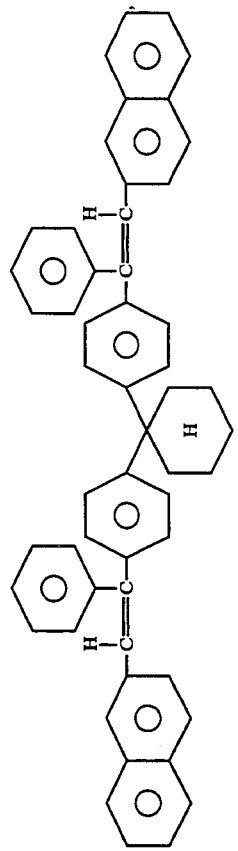
(46) 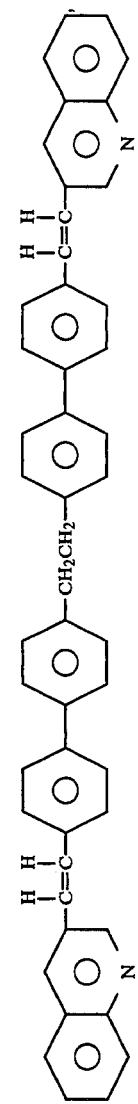
(47) 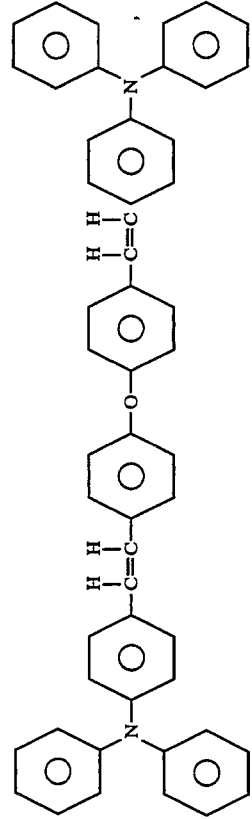
(48) 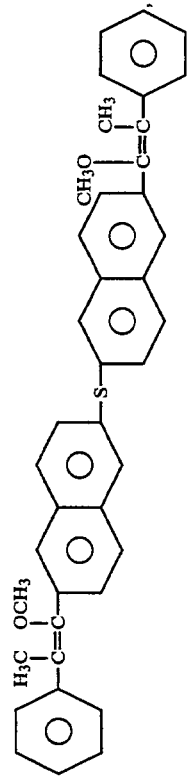
(49) 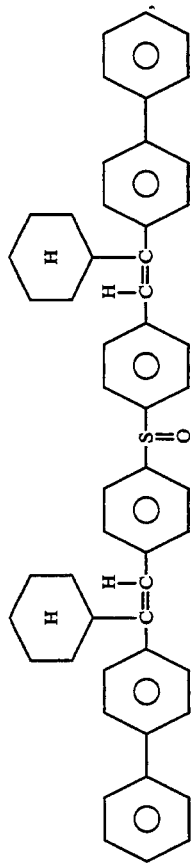

-continued
(50) 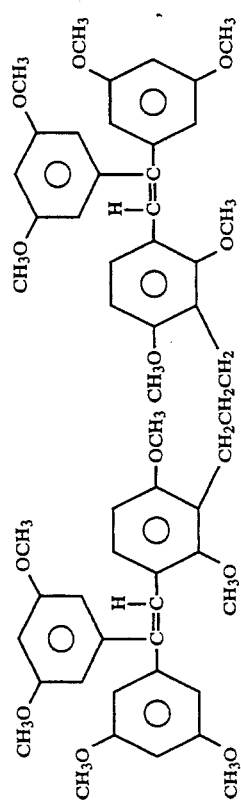 (51) 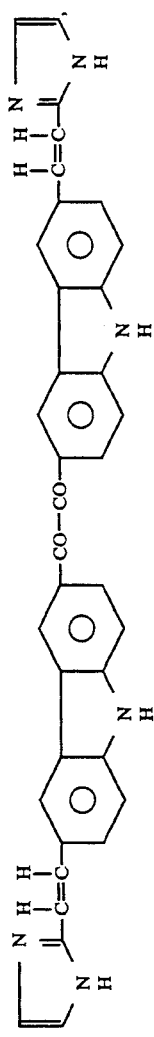 (52) 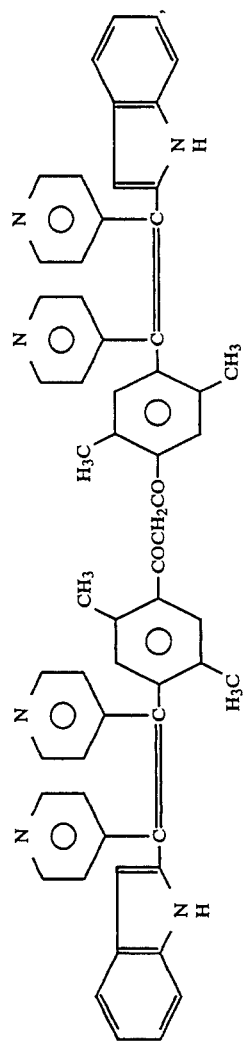 (53) 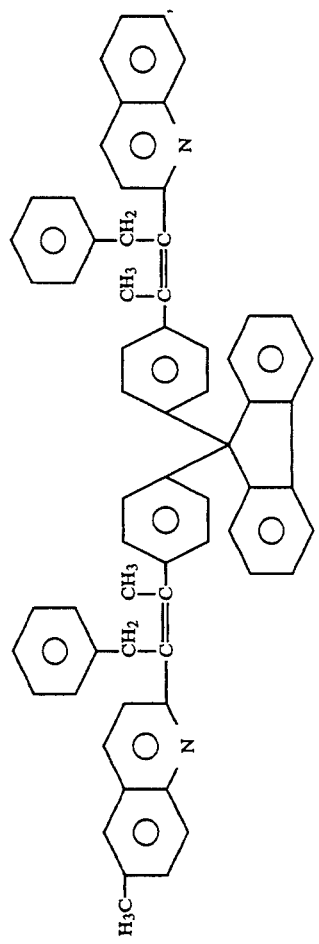

-continued
(54) 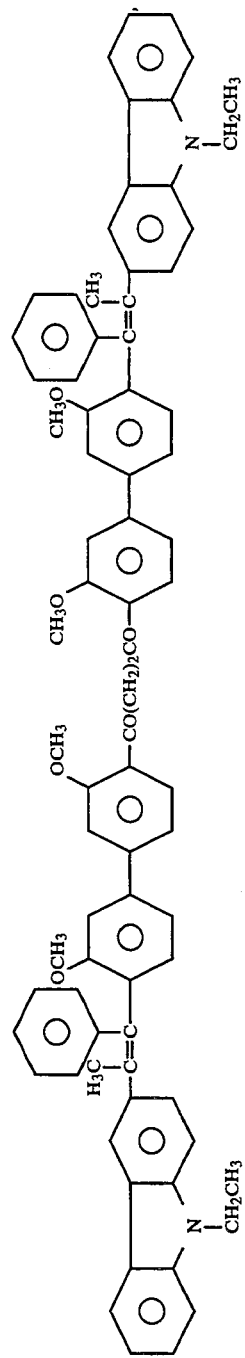 (55) 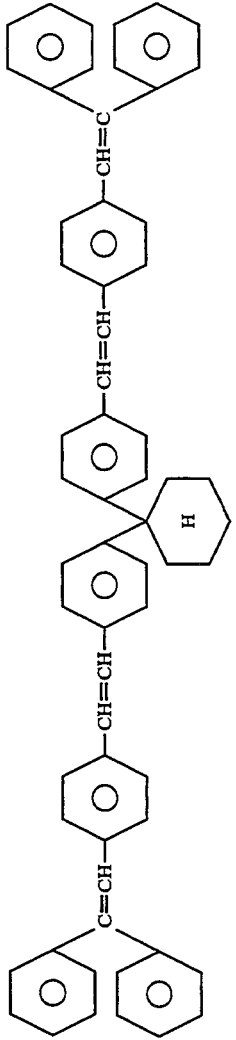 (56) 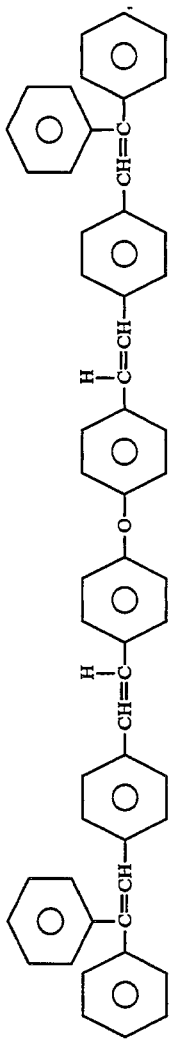 (57) 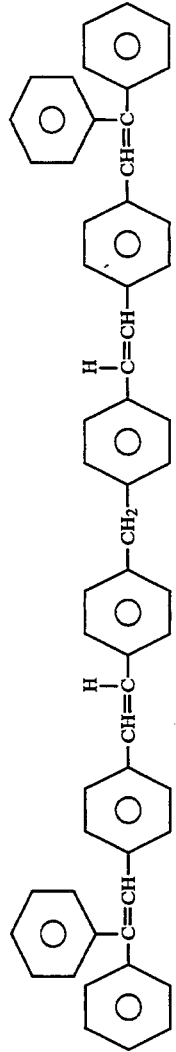 (58) 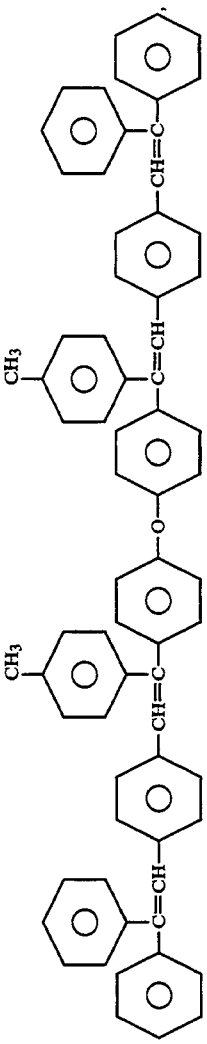

(59) 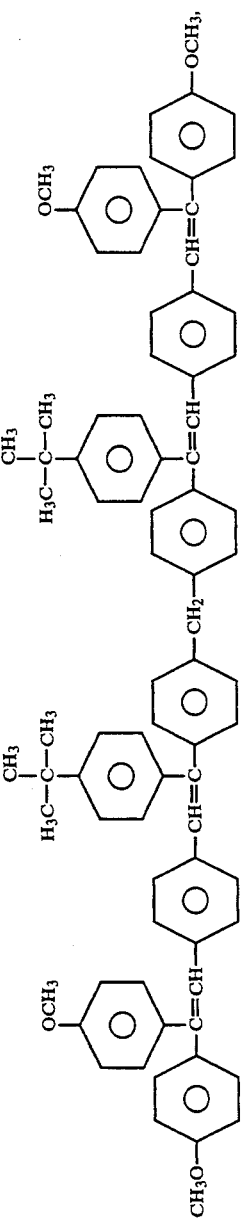
(60) 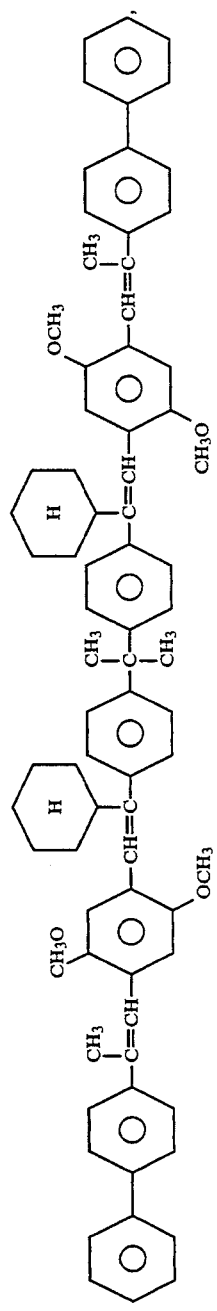
(61) 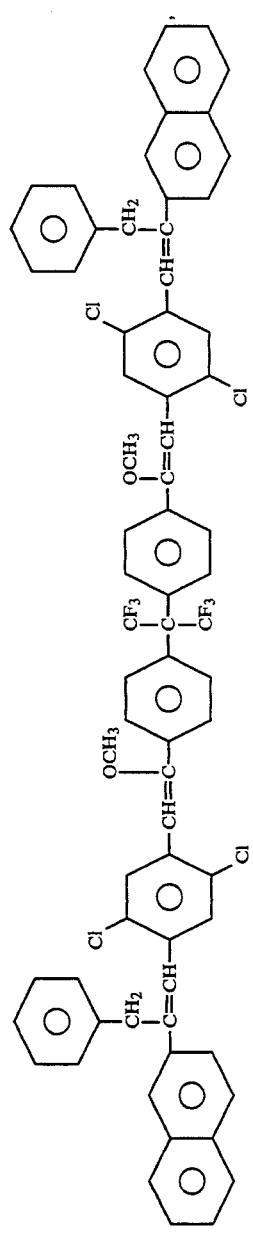
(62) 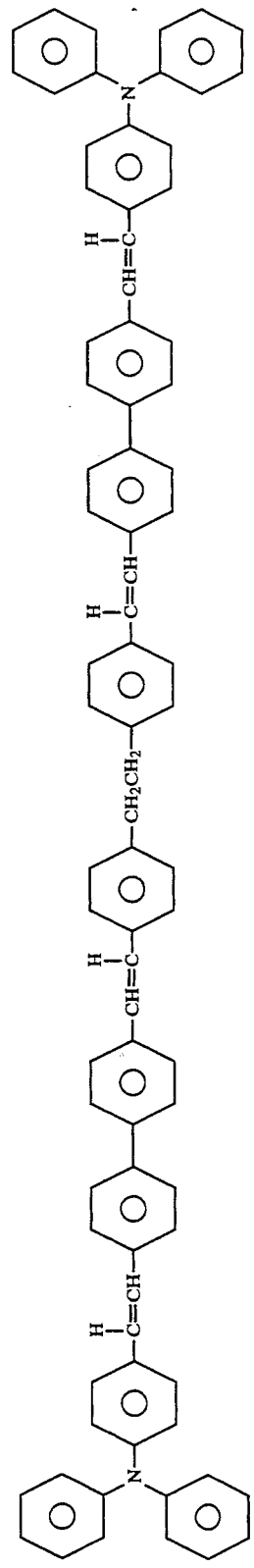

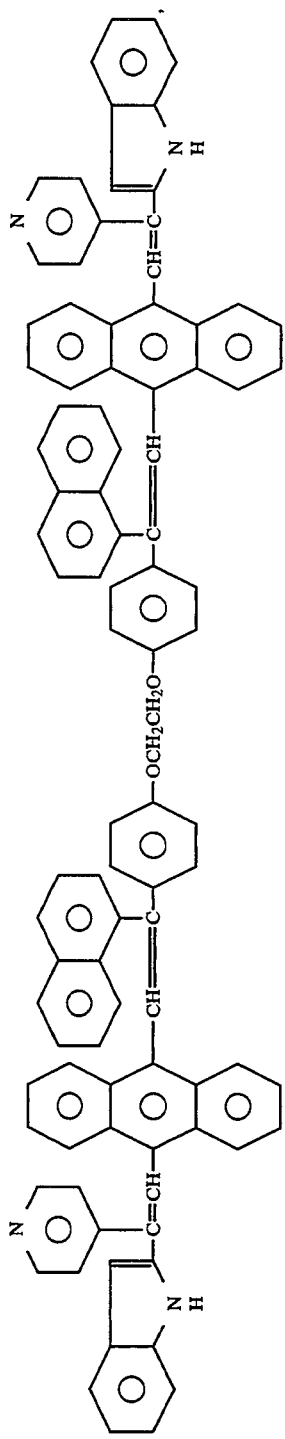
(63)
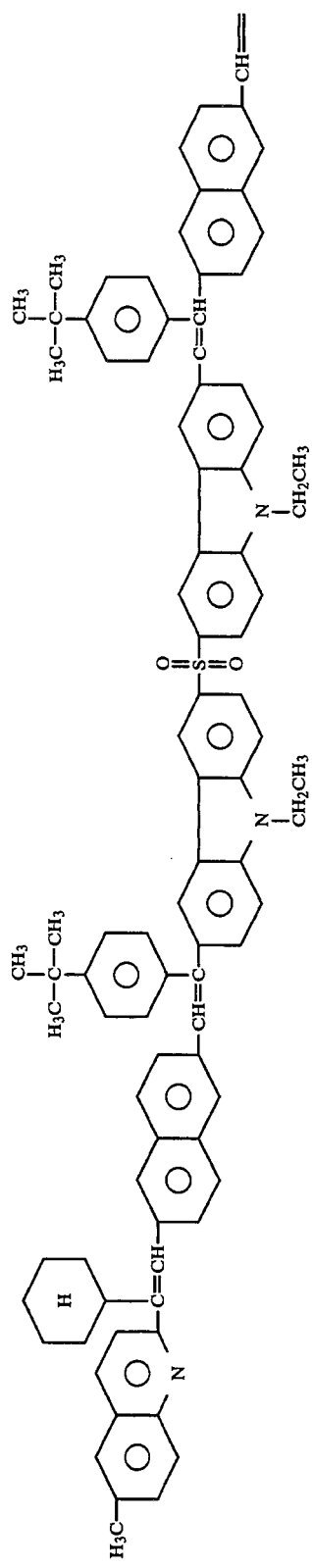
(64)
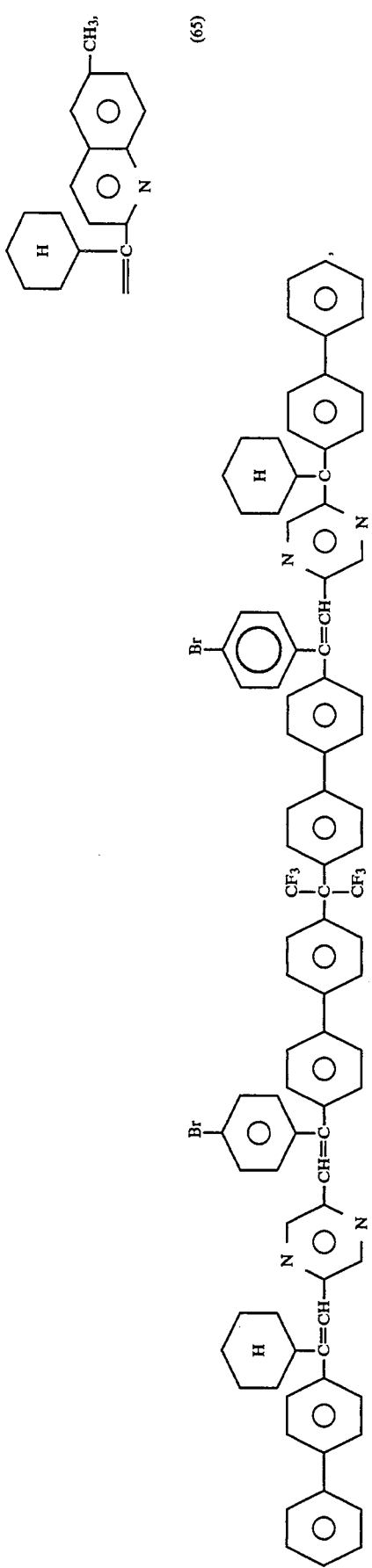
(65)

(66)
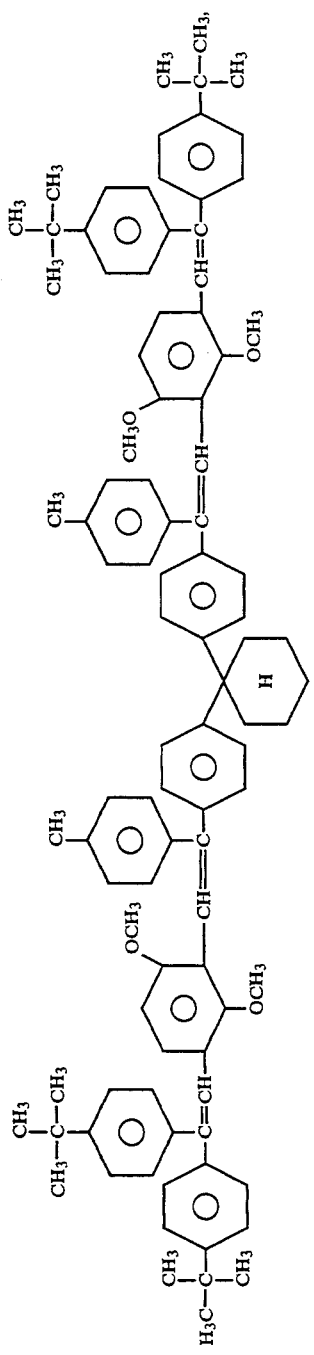
(67)
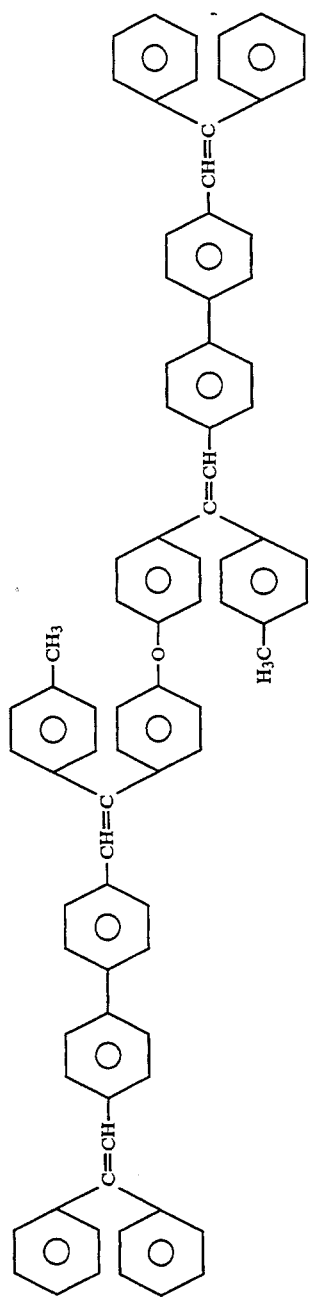
(68)
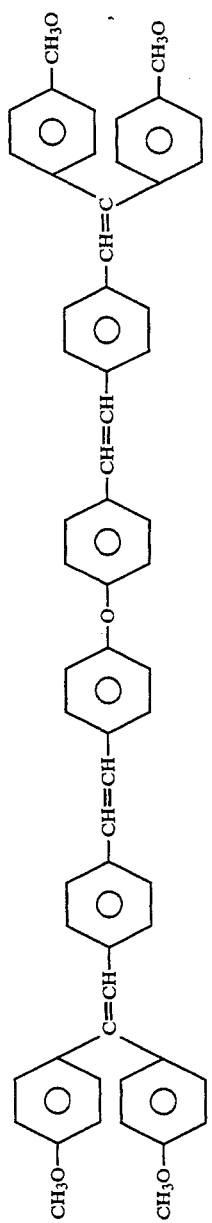

(69) (70) (71) (72)
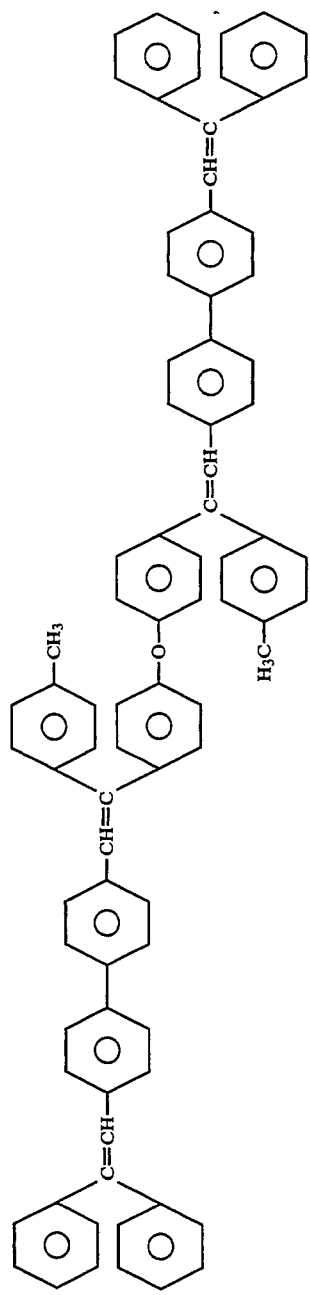
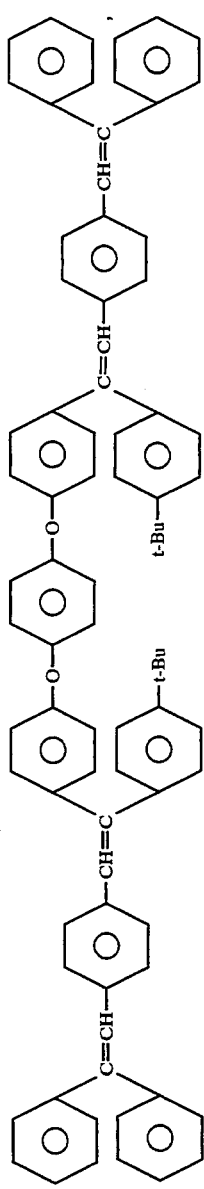
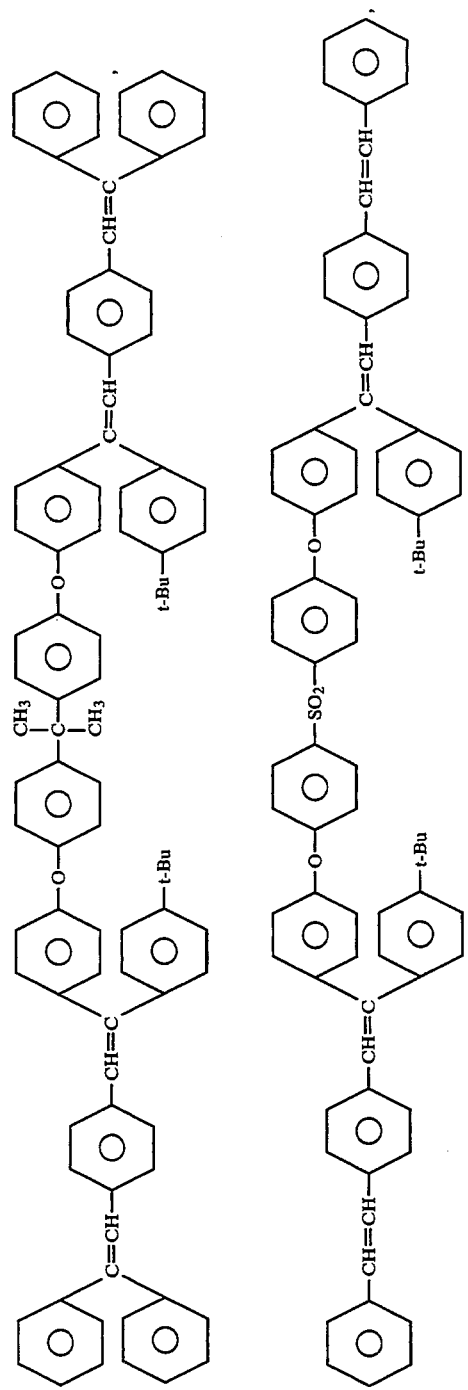

-continued
(73) 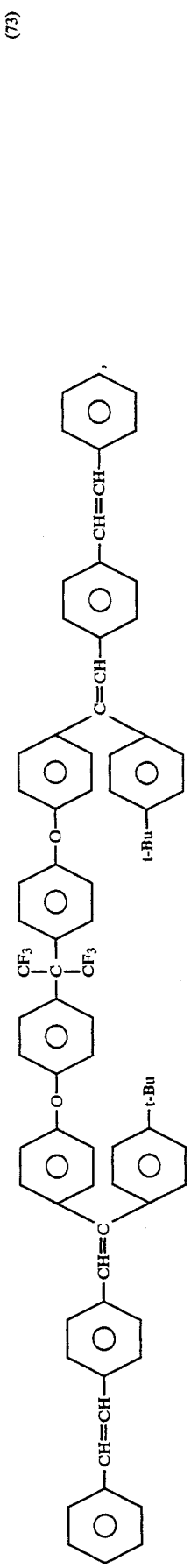 (74) 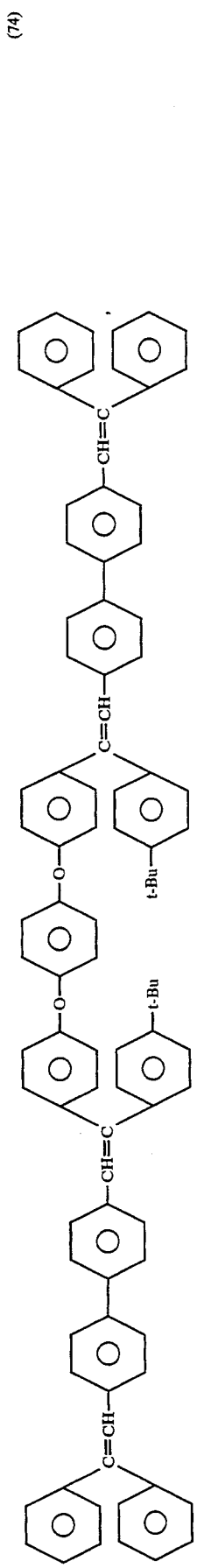 (75) 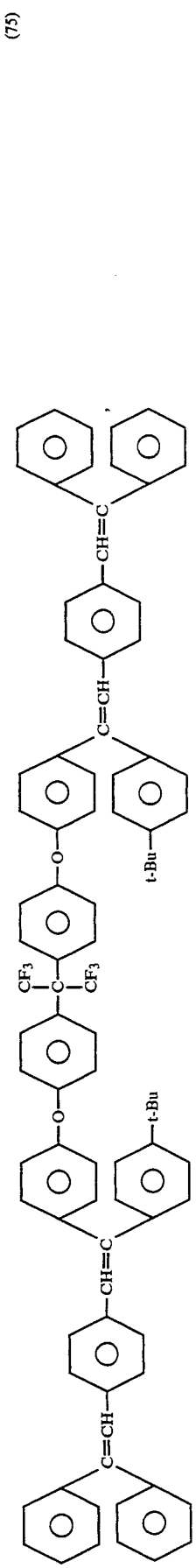 (76) 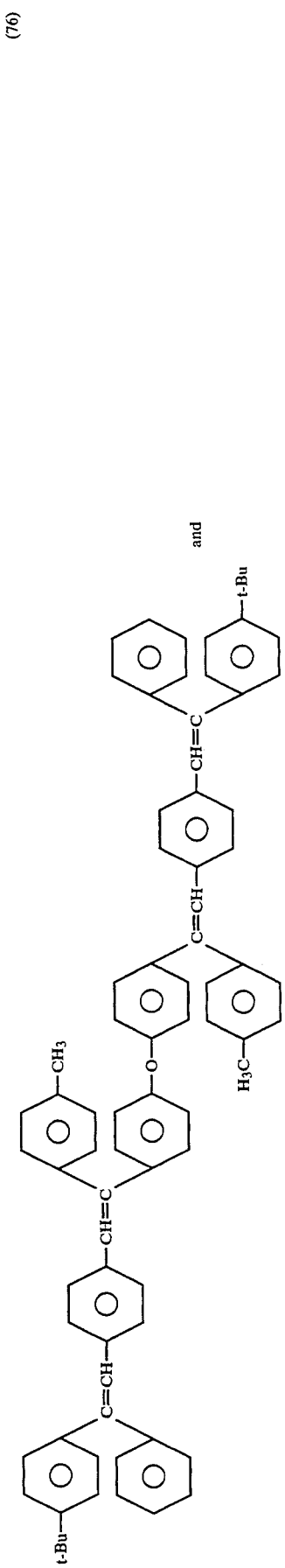

(77)
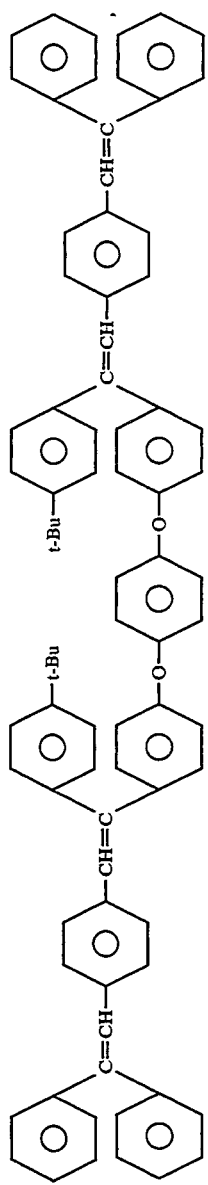

wherein t-Bu is tertiarybutyl.

26. The organic electroluminescence device according to claim 13, wherein the device is a laminate which contains in the following order: the cathode, the hole injection transportation layer, the emitting layer and the anode.

27. The electroluminescence device according to claim 13, wherein the device is a laminate which contains in the following order: the cathode, the hole injection transportation layer, the emitting layer, the electron injecting layer and the anode.

28. The organic electroluminescence device according to claim 13, wherein the device is a laminate which contains in the following order: the cathode, the emitting layer, the electron injection layer and the anode.

* * * * *